United States Patent
Lane et al.

(10) Patent No.: US 9,366,682 B2
(45) Date of Patent: Jun. 14, 2016

(54) USE OF STATHMIN AS A BIOMARKER OF DRUG RESPONSE TO FURAZANOBENZIMIDAZOLES

(75) Inventors: Heidi Alexandra Lane, Therwil (CH); Felix Bachmann, Basel (CH)

(73) Assignee: BASILEA PHARMACEUTICA AG, Basel (CH)

( * ) Notice: Subject to any disclaimer, the term of this patent is extended or adjusted under 35 U.S.C. 154(b) by 0 days.

(21) Appl. No.: 13/979,955

(22) PCT Filed: Jan. 19, 2012

(86) PCT No.: PCT/EP2012/050819
§ 371 (c)(1),
(2), (4) Date: Sep. 16, 2013

(87) PCT Pub. No.: WO2012/098208
PCT Pub. Date: Jul. 26, 2012

(65) Prior Publication Data
US 2013/0345263 A1    Dec. 26, 2013

(30) Foreign Application Priority Data
Jan. 21, 2011 (EP) .................................. 11151674

(51) Int. Cl.
| | | |
|---|---|---|
| A61K 31/415 | (2006.01) | |
| A61K 31/41 | (2006.01) | |
| G01N 33/68 | (2006.01) | |
| A61K 31/4245 | (2006.01) | |
| G01N 33/50 | (2006.01) | |
| C07D 413/04 | (2006.01) | |
| C07D 413/14 | (2006.01) | |
| A61K 31/4184 | (2006.01) | |

(52) U.S. Cl.
CPC ........ *G01N 33/6893* (2013.01); *A61K 31/4245* (2013.01); *C07D 413/04* (2013.01); *C07D 413/14* (2013.01); *G01N 33/5011* (2013.01); *G01N 33/5026* (2013.01); *A61K 31/4184* (2013.01); *G01N 2800/44* (2013.01); *G01N 2800/52* (2013.01)

(58) Field of Classification Search
CPC .................... A61K 31/4184; A61K 31/4245
USPC ................................................ 514/394, 364
See application file for complete search history.

(56) References Cited

U.S. PATENT DOCUMENTS

RE42,890 E * 11/2011 Eberle et al. .................... 548/125
8,802,858 B2 * 8/2014 Pohlmann et al. ......... 546/269.4

FOREIGN PATENT DOCUMENTS

| CN | 101140240 | 3/2008 |
| WO | 0244424 | 6/2002 |
| WO | 2004/103994 A1 | 12/2004 |
| WO | 2005/120520 A2 | 12/2005 |
| WO | 2006063135 | 6/2006 |
| WO | 2006076100 | 7/2006 |

OTHER PUBLICATIONS

Duran, George E., et al., "In Vitro activity of the novel tubulin active agent BAL27862 in MDR1(+) and MDR1(−) human breast and ovarian cancer variants selected for resistance to taxanes", Abstract article; AACR 101st Annual Meeting; Apr. 20, 2010.

Esteve, Marie-Anne et al., "BAL27862: A unique microtubule-targeted drug that suppresses microtubule dynamics, severs microtubules, and overcomes Bc1-2- and tubulin subtype-related drug resistance", Abstract article; AACR 101st Annual Meeting; Apr. 19, 2010.

Jiang, Hong et al., "Proteins induced by telomere dysfunction and DNA damage represent biomarkers of human aging and disease", PNAS, Aug. 12, 2008, vol. 105; No. 32; pp. 11299-11304.

Balachandran, Raghavan et al., "Altered levels and regulation of stathmin in paclitaxel-resistant ovarian cancer cells", Oncogene (2003) 22, pp. 8924-8930.

Orr, George A., et al., "Mechanism of Taxol resistance related to microtubules", Oncogene (2003) 22, pp. 7280-7295.

Rosell, Rafael et al., "Transcripts in pretreatment biopsies from a three-arm randomized trial in metastatic non-small-cell lung cancer", Oncogene (2003) 22, pp. 3548-3553.

Perez, Edith A., "Microtubule inhibitors: Differentiating tubulin-inhibiting agents based on mechanisms of action, clinical activity, and resistance", Mol Cancer Ther 2009;8(8); pp. 2086-2095.

Mistry, Sucharita J. et al., "Therapeutic interactions between stathmin inhibition and chemotherapeutic agents in prostate cancer", Mol Cancer Ther 2006;5(12); pp. 3248-3257.

Alli, Elizabeth, et al., "Effect of Stathmin on the Sensitivity to Antimicrotubule Drugs in Human Breast Cancer", Cancer Research 62, Dec. 1, 2002; pp. 6864-6869.

Nishio, Kazuto, M.D., et al., "Oncoprotein 18 Overexpression Increases the Sensitivity to Vindesine in the Human Lung Carcinoma Cells", 2001 Amer. Cancer Society, pp. 1494-1499.

McGrogan, Barbara T., et al., "Taxanes, microtubules and chemoresistant breast cancer", Biochimica et Biophysica Acta 1785, 2008, pp. 96-132.

Rosell, Rafael et al., "Molecular markers and targeted therapy with novel agents: prospects in the treatment of non-small cell lung cancer", Lung Cancer 38 (2002) Suppl 4, pp. 43-49.

(Continued)

*Primary Examiner* — Kevin E Weddington

(57) ABSTRACT

Use of stathmin as a biomarker for predicting the response, such as resistance, to a compound, wherein the compound is a furazanobenzimidazole compound of general formula (I).

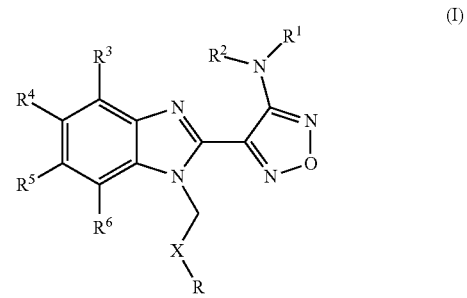

97 Claims, 16 Drawing Sheets

(56) References Cited

OTHER PUBLICATIONS

Carr et al., "FoxM1 Mediates Resistance to Herceptin and Paclitaxel," Cancer Res 2010;70:5054-5063.
Liu et al., "Expression of Stathmin, a Developmentally Controlled Cytoskeleton-Regulating Molecule, in Demyelinating Disorders," The Journal of Neuroscience, Jan. 19, 2005 • 25(3):737-747.
The International Search Report and Written Opinion, mailed on May 22, 2012, in the related PCT Appl. No. PCT/EP2012/050819.
Kavallaris et al., "Microtubules and resistance to tubulin-binding agents," Nat Rev Cancer. Mar. 2010; 10(3):194-204.
The English translation of the Japanese Office Action dated Oct. 20, 2015 in the related Japanese application No. 2013-549813.

* cited by examiner

Fig. 12A stathmin isoform a [Homo sapiens] (Sequence ID No. 1)

```
  1 massdiqvke lekrasgqaf elilsprske svpefplspp kkkdlsleei qkkleaaeer
 61 rksheaevlk qlaekrehek evlqkaieen nnfskmaeek lthkmeanke nreaqmaakl
121 erlrekdkhi eevrknkesk dpadetead
```

Fig. 12B stathmin isoform b [Homo sapiens] (Sequence ID No. 2)

```
  1 massdiqvke lekrasgqaf elilsprske svpefplspp kkkdlsleei qkkleaaeer
 61 rksheaevlk qlaekrehek evlqkaieen nnfskmaeek lthkmeanke nreaqmaakl
121 erlrekmyfw thgpgahpaq isaeqsclhs vpalcpalgl qsalitwsdl shhh
```

Figure 13

Homo sapiens stathmin, transcript variant 3 (SEQ. ID. No. 3)

```
   1 gctctcggcc aatgcggagc cccgcgcgga ggtcacgtgc ctctgtttgg cgcttttgtg
  61 cgcgcccggg tctgttggtg ctcagagtgt ggtcaggcgg ctcggactga gcaggacttt
 121 ccttatccca gttgattgtg cagaatacac tgcctgtcgc ttgtcttcta ttcaccatgg
 181 cttcttctga tatccaggtg aaagaactgg agaagcgtgc ctcaggccag gcttttgagc
 241 tgattctcag ccctcggtca aagaatctg ttccagaatt cccccttttcc cctccaaaga
 301 agaaggatct ttccctggag gaaattcaga agaaattaga agctgcagaa gaaagacgca
 361 agtcccatga agctgaggtc ttgaagcagc tggctgagaa acgagagcac gagaaagaag
 421 tgcttcagaa ggcaatagaa gagaacaaca acttcagtaa aatggcagaa gagaaactga
 481 cccacaaaat ggaagctaat aaagagaacc gagaggcaca aatggctgcc aaactggaac
 541 gtttgcgaga gaaggataag cacattgaag aagtgcggaa gaacaaagaa tccaaagacc
 601 ctgctgacga gactgaagct gactaatttg ttctgagaac tgactttctc cccatcccct
 661 tcctaaatat ccaaagactg tactggccag tgtcattta ttttttccct cctgacaaat
 721 attttagaag ctaatgtagg actgtatagg tagatccaga tccagactgt aagatgttgt
 781 tttagggct aaaggggaga aactgaaagt gttttactct ttttctaaag tgttggtctt
 841 tctaatgtag ctatttttct tgttgcatct tttctacttc agtacacttg gtgtactggg
 901 ttaatggcta gtactgtatt ggctctgtga aaacatattt gtgaaaagag tatgtagtgg
 961 cttcttttga actgttagat gctgaatatc tgttcacttt tcaatcccaa ttctgtccca
1021 atcttaccag atgctactgg acttgaatgg ttaataaaac tgcacagtgc tgttggtggc
1081 agtgacttct tttgagttag gttaataaat caagccatag agcccctcct ggttgatact
1141 tgttccagat ggggcctttg gggctggtag aaatacccaa cgcacaaatg accgcacgtt
1201 ctctgccccg tttcttgccc cagtgtggtt tgcattgtct ccttccacaa tgactgcttt
1261 gtttggatgc ctcagcccag gtcagctgtt actttctttc agatgtttat ttgcaaacaa
1321 ccatttttttg ttctgtgtcc cttttaaaag gcagattaaa agcacaagcg tgtttctaga
1381 gaacagttga gagagaatct caagattcta cttggtggtt tgcttgctct acgttacagg
1441 tggggcatgt cctcatcctt tcctgccata aaagctatga cacgagaatc agaatattaa
1501 taaaacttta tgtactgctg tagcaaaaaa aaaaaaaaa aa
```

Figure 14

Homo sapiens stathmin, transcript variant 2, (SEQ. ID. NO. 4)

```
   1 agggcactg ctctgtccga gtgctgccct tggggcgagg cgggcatgtg gctctacaag
  61 gtggagtcca ggcggccaaa gtttggaaag gactttcctt atcccagttg attgtgcaga
 121 atacactgcc tgtcgcttgt cttctattca ccatggcttc ttctgatatc caggtgaaag
 181 aactggagaa gcgtgcctca ggccaggctt ttgagctgat tctcagcect cggtcaaaag
 241 aatctgttcc agaattcccc ctttcccctc caaagaagaa ggatctttcc ctggaggaaa
 301 ttcagaagaa attagaagct gcagaagaaa gacgcaagtc ccatgaagct gaggtcttga
 361 agcagctggc tgagaaacga gagcacgaga agaagtgct tcagaaggca atagaagaga
 421 acaacaactt cagtaaaatg gcagaagaga aactgaccca caaatggaa gctaataaag
 481 agaaccgaga ggcacaaatg gctgccaaac tggaacgttt gcgagagaag gataagcaca
 541 ttgaagaagt gcggaagaac aaagaatcca aagaccctgc tgacgagact gaagctgact
 601 aatttgttct gagaactgac tttctcccca tccccttcct aaatatccaa agactgtact
 661 ggccagtgtc attttatttt ttccctcctg acaaatattt tagaagctaa tgtaggactg
 721 tataggtaga tccagatcca gactgtaaga tgttgtttta ggggctaaag gggagaaact
 781 gaaagtgttt tactcttttt ctaaagtgtt ggtctttcta atgtagctat ttttcttgtt
 841 gcatcttttc tacttcagta cacttggtgt actgggttaa tggctagtac tgtattggct
 901 ctgtgaaaac atatttgtga aaagagtatg tagtggcttc ttttgaactg ttagatgctg
 961 aatatctgtt cacttttcaa tcccaattct gtcccaatct taccagatgc tactggactt
1021 gaatggttaa taaaactgca cagtgctgtt ggtggcagtg acttcttttg agttaggtta
1081 ataaatcaag ccatagagcc cctcctggtt gatacttgtt ccagatgggg cctttggggc
1141 tggtagaaat acccaacgca caaatgaccg cacgttctct gccccgtttc ttgccccagt
1201 gtggtttgca ttgtctcctt ccacaatgac tgctttgttt ggatgcctca gcccaggtca
1261 gctgttactt tctttcagat gtttatttgc aaacaaccat tttttgttct gtgtcccttt
1321 taaaaggcag attaaaagca caagcgtgtt tctagagaac agttgagaga gaatctcaag
1381 attctacttg gtggtttgct tgctctacgt tacaggtggg gcatgtcctc atcctttcct
1441 gccataaaag ctatgacacg agaatcagaa tattaataaa actttatgta ctgctgtagc
1501 aaaaaaaaaa aaaaaaaa
```

Figure 15

Homo sapiens stathmin, transcript variant 1, (SEQ. ID. No. 5)

```
   1 atcaccgggc gtccgctccg gggtgccgtc gaggagacaa taggggggcgt gggccctcgt
  61 ttacctccct ccctccctcc cttccctgcg ggccccgccg ggttccccat tgtctgaagg
 121 gacgggcgg  tgccccaggg accagcggct ttaggaccaa actgcgggca gccagggccg
 181 cgaccctccc tgcgaccgtc ccctggcgac cgcagctggt gattgagggg cggcgctccc
 241 gggccccacg agggttcttc tgtcttcgcg gccggacgcg cggacagcgt gggtggcggc
 301 aggactttcc ttatcccagt tgattgtgca gaatacactg cctgtcgctt gtcttctatt
 361 caccatggct tcttctgata tccaggtgaa agaactggag aagcgtgcct caggccaggc
 421 ttttgagctg attctcagcc ctcggtcaaa agaatctgtt ccagaattcc ccctttcccc
 481 tccaagaag  aaggatcttt ccctggagga aattcagaag aaattagaag ctgcagaaga
 541 aagacgcaag tcccatgaag ctgaggtctt gaagcagctg gctgagaaac gagagcacga
 601 gaaagaagtg cttcagaagg caatagaaga gaacaacaac ttcagtaaaa tggcagaaga
 661 gaaactgacc cacaaaatgg aagctaataa agagaaccga gaggcacaaa tggctgccaa
 721 actggaacgt ttgcgagaga aggataagca cattgaagaa gtgcggaaga acaaagaatc
 781 caaagaccct gctgacgaga ctgaagctga ctaatttgtt ctgagaactg actttctccc
 841 catcccttc  ctaaatatcc aaagactgta ctggccagtg tcatttattt ttttccctcc
 901 tgacaaatat tttagaagct aatgtaggac tgtataggta gatccagatc cagactgtaa
 961 gatgttgttt tagggctaa  agggagaaa  ctgaaagtgt tttactcttt ttctaaagtg
1021 ttggtctttc taatgtagct attttttcttg ttgcatcttt tctacttcag tacacttggt
1081 gtactggggtt aatggctagt actgtattgg ctctgtgaaa acatatttgt gaaaagagta
1141 tgtagtggct tcttttgaac tgttagatgc tgaatatctg ttcacttttc aatcccaatt
1201 ctgtcccaat cttaccagat gctactggac ttgaatggtt aataaaactg cacagtgctg
1261 ttggtggcag tgacttcttt tgagttaggt taataaatca agccatagag cccctcctgg
1321 ttgatacttg ttccagatgg ggcctttggg gctggtagaa atacccaacg cacaaatgac
1381 cgcacgttct ctgccccgtt tcttgcccca gtgtggtttg cattgtctcc ttccacaatg
1441 actgctttgt ttggatgcct cagcccaggt cagctgttac tttctttcag atgtttattt
1501 gcaaacaacc attttttgtt ctgtgtccct tttaaaaggc agattaaaag cacaagcgtg
1561 tttctagaga acagttgaga gagaatctca agattctact tggtggtttg cttgctctac
1621 gttacaggtg gggcatgtcc tcatccttc  ctgccataaa agctatgaca cgagaatcag
1681 aatattaata aaactttatg tactgctgta gcaaaaaaaa aaaaaaaaa
```

Figure 16

Homo sapiens stathmin, transcript variant 4, (SEQ. ID. No. 6)

```
   1 gctctcggcc aatgcggagc cccgcgcgga ggtcacgtgc ctctgtttgg cgcttttgtg
  61 cgcgcccggg tctgttggtg ctcagagtgt ggtcaggcgg ctcggactga gcaggacttt
 121 ccttatccca gttgattgtg cagaatacac tgcctgtcgc ttgtcttcta ttcaccatgg
 181 cttcttctga tatccaggtg aaagaactgg agaagcgtgc ctcaggccag gcttttgagc
 241 tgattctcag ccctcggtca aaagaatctg ttccagaatt ccccctttcc cctccaaaga
 301 agaaggatct ttccctggag gaaattcaga agaaattaga agctgcagaa gaaagacgca
 361 agtcccatga agctgaggtc ttgaagcagc tggctgagaa acgagagcac gagaaagaag
 421 tgcttcagaa ggcaatagaa gagaacaaca acttcagtaa aatggcagaa gagaaactga
 481 cccacaaaat ggaagctaat aaagagaacc gagaggcaca aatggctgcc aaactggaac
 541 gtttgcgaga gaagatgtac ttctggactc acgggcctgg ggcccaccca gcacagatct
 601 ctgctgagca atcttgtctc cactctgttc ctgccctttg cccagccctg ggcctccaat
 661 ctgcattgat tacctggtct gatctctctc accatcacta ggtacttaat aaatatttgc
 721 tgttgatgat agcaatgacc ttgagactga tgaacagtct ggccaagagg atccttgatg
 781 tggaagatag aaaaagcctt tggggtcagg cagacttgga ttctaatacc agccagttct
 841 gcttgctgtg tctgagcctc agtttactca tctgtgaaga ggaggtagca agaatgaaaa
 901 tgcctgcctt gtggtttgtt gtaaggacag acactgccaa cgtagagggc ccagcagctc
 961 acagaccagt tgctctgaga gcagaccact cttgccttga tggtagggaa ctattttttgt
1021 gcgtggcaag tgggaccttta ggaaggaagg caactgtgag gcttctgaga aggaccctac
1081 acaagggagt ttcctcccag ggcaggtgaa tggagagggt ggcagaagcc tacgggaagg
1141 ggtcacaggg atcagctaga gagtgccacc acccttcctg gggaatgcag ggcaaggtcc
1201 ctggtgggag ttttcctggg aagccaaaga agcgcccaac aaagacagaa tcaacatttg
1261 ggtacctttg gtacccagag gcagcaatgc caactacaac cacactggaa gaagaagacc
1321 ttctccgcat agattctctg atctcttcct ccttcatggc accagccctg gggaaccagc
1381 atggtgggga aataatgaag ctggaataca accacttaca gacttcacaa cctcctcctg
1441 tagataccaa agggatttta ggatcacatt ttatttctca cctgagcaag aaaagctaca
1501 ggagcatctc aagcagaggg caggagtctc cagaggagtt caagggctc tggcaagaaa
1561 aatcaagggg ctgtgttcaa gaactggctc ccttggtgat tgtattacga agcccatgtg
1621 tgctggatgc tgatgaaatt gctgccaaat gcctgtgcag ccttggcaag gcccttatt
1681 tctctgggtc tccatttctc tctctctttt tttttttttt ttttttttga ggcagagtct
1741 cactctgtcg cccaggctgg agggcagtgg cgtgatctcg gctcactgca agccccacct
1801 tctgagttca cgccattcta ctgcctcagc ctcccgagta gctgggacta caggcgccca
1861 ccaccacgcc cggcttattt tttgtatttt tagtagagac ggggtttcac cgcattagcc
1921 aagatggtct cgatcctg acctcgtgat tcacccacct cagcctccca aagtgctggg
1981 attacaggca tgagccactg cgcccggcct gggtctccgt ttctctagct gtgaaatgac
2041 tgttctaaaa gagccctgcc ggactttggc agtctgtaag aagacctgag ttcttctctc
2101 agttccaagc aggaaaattg aacataccct gagcccagag cctgcaacaa actctgggca
2161 gcctcaggaa gtcaggcagt gaagtcggaa aaatgatctc ttctgtatag ggagaaaata
2221 aaagtttaaa aatttgtaaa aaaaaaaaaa agaaaaaaaa aaaaa
```

USE OF STATHMIN AS A BIOMARKER OF DRUG RESPONSE TO FURAZANOBENZIMIDAZOLES

This application is a National Stage Application of PCT/EP2012/050819 filed Jan. 19, 2012, which claims priority from European Patent Application 11151674.6 filed on Jan. 21, 2011. The priority of both said PCT and European Patent Application are claimed.

The present invention relates to use of stathmin as a biomarker for predicting the response of a disease, such as a neoplastic or autoimmune disease, preferably cancer, to a compound of general formula I, such as 3-(4-{1-[2-(4-aminophenyl)-2-oxo-ethyl]-1H-benzoimidazol-2-yl}-furazan-3-ylamino)-propionitrile (BAL27862). In other aspects it relates to methods and kits, as well as methods of treatment involving the use of the biomarker.

Microtubules are one of the components of the cell cytoskeleton and are composed of heterodimers of alpha and beta tubulin. Agents that target microtubules are among the most effective cytotoxic chemotherapeutic agents having a broad spectrum of activity. Microtubule destabilising agents (e.g. the vinca-alkaloids such as vincristine, vinblastine and vinorelbine) are used for example in the treatment of several types of hematologic malignancies, such as lymphoblastic leukaemia and lymphoma, as well as solid tumours, such as lung cancer. Microtubule stabilising agents (e.g. the taxanes such as paclitaxel, docetaxel) are used for example in the treatment of solid tumours, including breast, lung and prostate cancer.

However resistance to these known microtubule targeting agents can occur. The resistance can either be inherent or can be acquired after exposure to these agents. Such resistance therefore impacts patient survival rates, as well as choices of treatment regimes. Several potential mechanisms of resistance have been identified, and include defects in the microtubule targets, such as elevated levels of beta-tubulin subtype III and acquired mutations in beta-tubulin subtype I that are known to reduce taxane binding. Furthermore, defects in other cell proteins have been suggested to be associated with resistance to certain microtubule targeting agents, such as overexpression of p-glycoprotein (P-gp, also known as multidrug resistance protein 1 or MDR1). Such factors may then be used as biomarkers of resistance to these conventional microtubule targeting agents.

A relatively recently discovered class of microtubule destabilising agents are compounds encompassed by the formula given below:

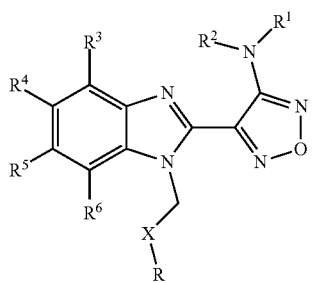

(I)

wherein
R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y, wherein Y stands for oxygen or nitrogen substituted by hydroxy or lower alkoxy;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable salts thereof;
or wherein
R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;
and wherein pyridinyl is optionally substituted by lower alkoxy, amino or halogen;
X represents oxygen;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable salts thereof;
and wherein the prefix lower denotes a radical having up to and including a maximum of 7, especially up to and including a maximum of 4 carbon atoms.

These compounds are disclosed in WO2004/103994 A1, which is incorporated by cross-reference herein. These compounds have been shown to arrest tumour cell proliferation and induce apoptosis.

The synthesis of compounds of formula I is described in WO2004/103994 A1, in general on pages 29-35, and specifically on pages 39-55, which are incorporated herein by cross-reference. They may be prepared as disclosed or by an analogous method to the processes described therein.

One compound falling within this class, known as BAL27862, and shown in WO2004/103994 A1 as example 58, and specifically incorporated by reference herein, has the structure and chemical name given below:

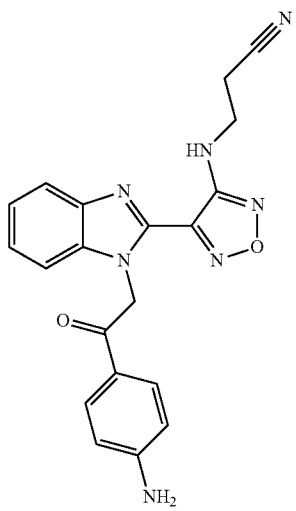 [SMILES: N#CCCNc1nonc1-c1nc2ccccc2n1CC(=O)c1ccc(N)cc1]

Chemical name: 3-(4-{1-[2-(4-Amino-phenyl)-2-oxo-ethyl]-1H-benzoimidazol-2-yl}-furazan-3-ylamino)-propionitrile Or herein as Compound A Further compounds exemplified in WO2004/103994 A1 as examples 50 and 79 respectively, and also specifically incorporated by cross-reference herein, have the structures and chemical names given below:

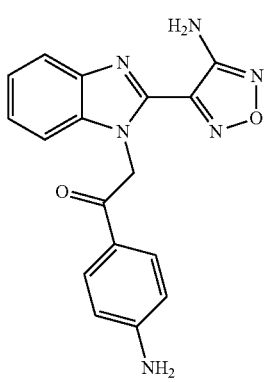 [SMILES: Nc1ccc(C(=O)Cn2c(-c3nonc3N)nc3ccccc32)cc1]

Chemical name: 2-[2-(4-Amino-furazan-3-yl)-benzoimidazol-1-yl]-1-(4-amino-phenyl)-ethanone Or herein as Compound B and

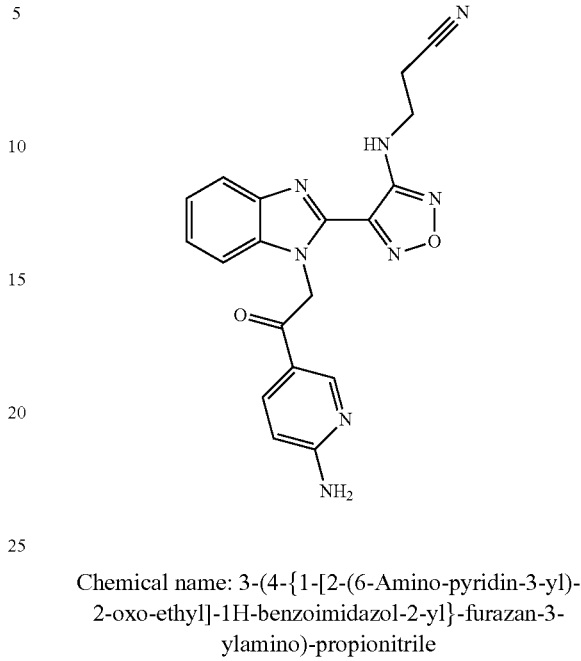

Chemical name: 3-(4-{1-[2-(6-Amino-pyridin-3-yl)-2-oxo-ethyl]-1H-benzoimidazol-2-yl}-furazan-3-ylamino)-propionitrile or herein as Compound C.

BAL27862 has activity across a broad panel of experimental, solid tumour xenograft models. Moreover, activity is retained even against tumour models which are selected for resistance to conventional microtubule targeting agents (including the vinca-alkaloid microtubule destabilisers and the microtubule stabilisers paclitaxel and epothilone B). BAL27862 activity is not affected by over-expression of the P-gp pump in any models tested in vitro, nor in human mammary tumour xenografts. Additionally, BAL27862 retained its activity despite elevated levels of beta-tubulin subtype III and mutations in tubulin subtype I.

Hence, BAL27862 activity is not affected by a number of factors that confer resistance to conventional microtubule targeting agents.

Moreover, it is known that compounds of general formula I have a different effect on the phenotype of cells compared to other microtubule targeting agents, including other microtubule destabilisers. Treatment with a compound of general formula I induces a consistent microtubule phenotype in tumour cell lines derived from a variety of organs, for example lung, cervix and breast, as seen in FIG. 1. Staining the microtubules in these cells with an anti-alpha-tubulin antibody shows that rather than the mitotic spindle fibres of untreated cells, only dot-like structures are visible in the treated cells. This same effect is also shown using Compounds C and B in FIGS. 2A and 2B respectively on the lung cancer cell line A549. It is however very distinct from that observed with the conventional microtubule targeting agents vinblastine, colchicine, paclitaxel and nocodazole as seen in FIGS. 3B, 3C, 3D and 4, respectively. The microtubules were stained with an anti-alpha-tubulin antibody and the cells viewed at a 1000× magnification (FIGS. 3, 4). For the cells treated with BAL27862, multiple dot-like structures are visible, whereas, in stark contrast, the other conventional drugs produce filamentous microtubule structures, or dense microtubule aggregate structures. These differences at the phenotypic level, at compound doses considered optimal in terms of antiproliferative effect, indicate a difference in the mode of action at the molecular level.

Furthermore, it is known that BAL27862 elicits a dominant microtubule phenotype in the presence of the other microtubule targeting agents. Treatment with vinblastine, colchicine, paclitaxel or nocodazole alone induced the microtubule phenotypes characteristic of these agents (FIG. 5A, 5D, 5G, 6C-6F respectively). However, combination treatment with BAL27862 for the last 4 hours resulted in disruption of these phenotypes; despite the continued presence of vinblastine, colchicine, paclitaxel or nocodazole (FIG. 5B, 5E, 5H, 6G-6J respectively). In contrast, treating first with BAL27862 and subsequently for 4 hours in combination with vinblastine, colchicine, paclitaxel or nocodazole had no impact on generation of the phenotype consistent with BAL27862 treatment (FIG. 5C, 5F, 5I, 6K-6N respectively).

These data all demonstrate that BAL27862 affects microtubule biology in a different manner than conventional microtubule targeting agents.

Thus, from information about conventional microtubule targeting agents, predictions cannot be made concerning if, or how, particular genes are involved in the action of compounds of general formula I.

An object of the present invention is to identify factors which are associated with response to compounds of formula I or pharmaceutically acceptable derivatives thereof, for example to identify factors associated with resistance to compounds of general formula I, in particular BAL27862 or pharmaceutically acceptable derivatives thereof, as defined below.

It has surprisingly been found that stathmin may be used as a biomarker of response to treatment with a compound of general formula I or pharmaceutically acceptable derivatives thereof, as defined below.

In one preferred embodiment of the invention, relatively high stathmin levels in a tumour sample are associated with inherent resistance to BAL27862.

Human stathmin has been assigned Human Gene Nomenclature Committee Identification number HGNC ID: 6510 and Entrez Gene ID 3925. The name stathmin was proposed by Sobel et al., after studies on the protein in rat brains, the name coming from the Greek "stathmos" meaning relay. (Sobel A, Boutterin M C, Beretta L, Chneiweiss H, Doye V, Peyro-Saint-Paul H., J Biol Chem. 1989 Mar. 5; 264(7):3765-72. "Intracellular substrates for extracellular signaling. Characterization of a ubiquitous, neuron-enriched phosphoprotein (stathmin).")

Stathmin is also known as stathmin 1; STMN1; oncoprotein 18; OP18; prosolin; metablastin; leukemia-associated phosphoprotein p18; LAP18; Lag; PP17; phosphoprotein 19; PP19; PR22; C1orf215; FLJ32206; MGC138869; MGC138870 and SMN. For simplicity, the term stathmin shall be used herein to encompass all the previously mentioned synonyms and refers to this entity on both the nucleic acid (e.g. mRNA, cDNA, DNA) and protein levels (including isoforms and post-translationally modified forms of the expressed protein) as appropriate.

In humans the stathmin gene is located on chromosome 1. Protein sequences coding for stathmin isoform a and isoform b are available via National Center for Biotechnology Information (NCBI) accession number NP_005554 and NP_001138926, respectively. These isoforms are also shown here in SEQ ID number 1 (NP_005554.1) and SEQ ID number 2 (NP_001138926.1). Multiple mRNA transcript variants are known for stathmin isoform a.

One aspect of the present invention relates to use of stathmin as a biomarker for predicting the response to a compound, wherein the compound is a compound of general formula I,

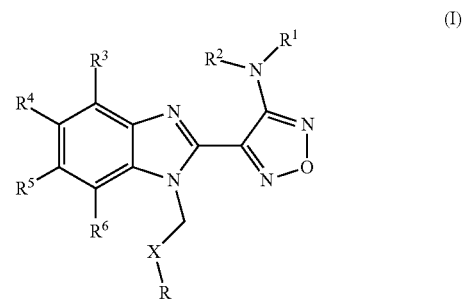

(I)

wherein
R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C═Y, wherein Y stands for oxygen or nitrogen substituted by hydroxy or lower alkoxy;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable derivatives thereof,
or wherein
R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;
and wherein pyridinyl is optionally substituted by lower alkoxy, amino or halogen;
X represents oxygen;
$R^1$ represents hydrogen, lower alkylcarbonyl, hydroxy-lower alkyl or cyano-lower alkyl;
$R^2$, $R^3$ and $R^6$ represent hydrogen;

$R^4$ and $R^5$, independently of each other, represent hydrogen, lower alkyl or lower alkoxy;
or $R^4$ and $R^5$ together represent methylenedioxy;
and pharmaceutically acceptable derivatives thereof;
and wherein the prefix lower denotes a radical having up to and including a maximum of 7, especially up to and including a maximum of 4 carbon atoms.

Preferably the response may be of a disease in a subject. Also preferably the response may be to treatment, i.e. to treatment with the compound of general formula I or pharmaceutically acceptable derivatives thereof.

The biomarker stathmin is measured ex vivo in a sample or samples taken from the human or animal body, preferably taken from the human body.

In a preferred embodiment, the invention relates to use of stathmin as a biomarker for predicting the resistance of a disease in a subject to a compound of general formula I or pharmaceutically acceptable derivatives thereof as defined above.

Preferably the pharmaceutically acceptable derivative is selected from the group consisting of a salt, solvate, pro-drug, salt of a pro-drug, polymorph and isomer of a compound of general formula I. Pro-drugs are preferably ester and amides of naturally occurring amino acids, small peptides or pegylated hydroxy acids. More preferably, the pro-drug is an amide formed from an amino group present within the R group of the compound of general formula I and the carboxy group of glycine, alanine or lysine.

Particularly preferably the compound is

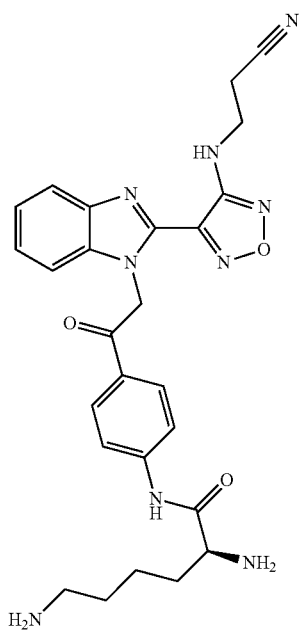 [SMILES: N#CCCNc1nonc1-c1nc2ccccc2n1CC(=O)c1ccc(NC(=O)[C@@H](N)CCCCN)cc1]

or a pharmaceutically acceptable salt thereof, preferably a hydrochloride salt thereof, most preferably a dihydrochloride salt thereof.

Another aspect of the present invention relates to a method for predicting the response of a disease in a subject to a compound of general formula I or pharmaceutically acceptable derivatives thereof as defined above, comprising the steps of:
a) measuring a level of stathmin in a sample pre-obtained from the subject to obtain a value or values representing this level; and
b) comparing the value or values from step a) to a standard value or set of standard values.

Further preferably the response which is predicted is resistance.

The measuring of a level or levels of stathmin is performed ex-vivo in a sample or samples pre-obtained from the subject. Pre-obtained refers to the fact that the sample is obtained before it is subjected to any method involving measuring the level of the biomarker, and pre-obtained is not to be understood as in relation to treatment.

In a preferred embodiment, a higher level of stathmin in the sample from the subject relative to a standard value or set of standard values predicts resistance.

Also preferably, the disease is a neoplastic or autoimmune disease. More preferably the disease is cancer. Especially preferably the cancer is selected from the group consisting of breast cancer, prostate cancer, cervical cancer, gastric cancer, ovarian cancer, colorectal cancer (i.e including colon cancer and rectal cancer), pancreatic cancer, liver cancer, brain cancer, neuroendocrine cancer, lung cancer, kidney cancer, hematological malignancies, melanoma and sarcomas. More especially preferably the cancer is selected from the group consisting of breast cancer, cervical cancer, gastric cancer, lung cancer and melanoma. Particularly preferably the cancer is selected from the group consisting of gastric cancer, lung cancer and melanoma.

In a further aspect, the invention relates to a method of treating a neoplastic or autoimmune disease, preferably cancer, in a subject in need thereof, comprising measuring a level of stathmin in a sample from the subject to obtain a value or values representing this level, and treating the subject with a compound of general formula I or a pharmaceutically acceptable derivative thereof as defined above, if the level of stathmin in said sample is not higher than a standard value or set of standard values.

In yet a further aspect, the invention relates to stathmin for use in the treatment of a neoplastic or autoimmune disease, preferably cancer, comprising measuring a level of stathmin in a sample from a subject to obtain a value or values representing this level, and treating the subject with a compound of general formula I or a pharmaceutically acceptable derivative thereof as defined above, if the level of stathmin is not higher than a standard value or set of standard values.

The measuring of a level of stathmin is performed ex-vivo in a sample pre-obtained from the subject.

The invention also relates in another aspect to a method of treating a neoplastic or autoimmune disease, preferably cancer, by first decreasing a level of stathmin in a subject that has a sample with a higher level of stathmin compared to a standard level or set of standard levels then treating the subject with a compound of general formula I or a pharmaceutically acceptable derivative thereof as defined above.

In yet another aspect the invention relates to a kit for predicting the response to a compound of general formula I or a pharmaceutically acceptable derivative thereof, as defined above, comprising reagents necessary for measuring the level of stathmin in a sample. More preferably the kit also comprises a comparator module which comprises a standard value or set of standard values to which the level of stathmin in the sample is compared.

Furthermore preferably the kit comprises a compound of general formula I or a pharmaceutically acceptable derivative thereof as defined above. In an especially preferred embodiment the kit comprises a compound of the following formula or a pharmaceutically acceptable salt thereof

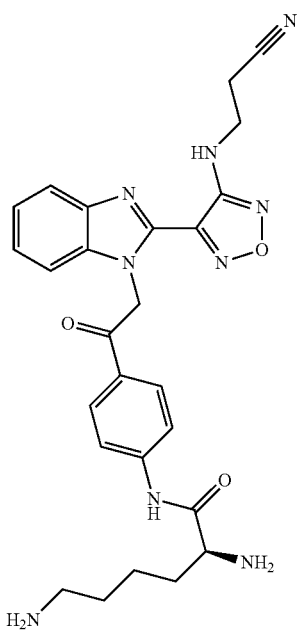

Chemical name: S-2,6-Diamino-hexanoic acid [4-(2-{2-[4-(2-cyano-ethylamino)-furazan-3-yl]-benzoimidazol-1-yl}-acetyl)-phenyl]-amide In a particularly preferred embodiment the pharmaceutically acceptable salt is a dihydrochloride salt.

Another further aspect of the invention relates to a device for predicting the response to a compound of general formula I or a pharmaceutically acceptable derivative thereof as defined above, comprising reagents necessary for measuring the level of stathmin in a sample and a comparator module which comprises a standard value or set of standard values to which the level of stathmin in the sample is compared.

In a preferred embodiment, the reagents in the kit or device comprise a capture reagent comprising a detector for stathmin, and a detector reagent. Especially preferably the capture reagent is an antibody. Also preferably, the disease is predicted to be resistant to treatment with said compound when stathmin is higher relative to a standard value or set of standard values. In a preferred embodiment, the comparator module is included in instructions for use of the kit. In another preferred embodiment the comparator module is in the form of a display device.

Embodiments of the present invention will now be described by way of example with reference to the accompanying figures. The invention however is not to be understood as limited to these embodiments.

BRIEF DESCRIPTION OF THE FIGURES

FIGS. 1A and 1B: A549 NSCLC cells;
FIGS. 1C and 1D: HeLa cervical cancer cells;
FIGS. 1E and 1F: SKBR3 breast cancer cells
Vehicle control treatment:
FIGS. 1A, 1C & 1E,
BAL27862 treatment:
FIGS. 1B, 1D & 1F.

FIG. 2A: treatment with 20 nM compound C
FIG. 2B: treatment with 80 nM compound B

FIG. 5A: 24 hours vinblastine treatment;
FIG. 5B: 24 hours vinblastine treatment with the final 4 hours including BAL27862;
FIG. 5C: 24 hours BAL27862 treatment with the final 4 hours including vinblastine.
FIG. 5D: 24 hours colchicine treatment;
FIG. 5E: 24 hours colchicine treatment with the final 4 hours including BAL27862;
FIG. 5F: 24 hours BAL27862 treatment with the final 4 hours including colchicine.
FIG. 5G: 24 hours paclitaxel treatment;
FIG. 5H: 24 hours paclitaxel treatment with the final 4 hours including BAL27862;
FIG. 5I: 24 hours BAL27862 treatment with the final 4 hours including paclitaxel.

FIG. 6A: 24 hours control treatment;
FIG. 6B: 24 hours of 25 nM BAL27862 treatment;
FIG. 6C: 24 hours of 50 nM nocodazole treatment
FIG. 6D: 24 hours of 100 nM nocodazole treatment
FIG. 6E: 24 hours of 150 nM nocodazole treatment
FIG. 6F: 24 hours of 200 nM nocodazole treatment
FIG. 6G: 24 hours of 50 nM nocodazole treatment with the final 4 hours including 25 nM BAL27862;

FIG. 6H: 24 hours of 100 nM nocodazole treatment with the final 4 hours including 25 nM BAL27862;

FIG. 6I: 24 hours of 150 nM nocodazole treatment with the final 4 hours including 25 nM BAL27862;

FIG. 6J: 24 hours of 200 nM nocodazole treatment with the final 4 hours including 25 nM BAL27862;

FIG. 6K: 24 hours of 25 nM BAL27862 treatment with the final 4 hours including 50 nM nocodazole;

FIG. 6L: 24 hours of 25 nM BAL27862 treatment with the final 4 hours including 100 nM nocodazole;

FIG. 6M: 24 hours of 25 nM BAL27862 treatment with the final 4 hours including 150 nM nocodazole;

FIG. 6N: 24 hours of 25 nM BAL27862 treatment with the final 4 hours including 200 nM nocodazole.

FIG. 11A: Samples were prepared from HeLa, H460 and A549 cell lines, and quantitative RT-PCR was performed on these to measure RNA levels. The HeLa results were set at 100%, and the graph shows the RNA expression levels in the H460 and A549 samples relative to the HeLa values. FIG. 11B: Whole cell protein extracts were prepared from the same passages of the HeLa, H460 and A549 cell lines and then analysed by immunoblotting for stathmin protein expression. Actin levels act as a loading control.

FIG. 12A: shows the protein sequence of stathmin isoform a [*Homo sapiens*] (Sequence ID No. 1).

FIG. 12B: shows the protein sequence of stathmin isoform b [*Homo sapiens*] (Sequence ID No. 2).

FIG. 13: shows the nucleic acid sequence of *Homo sapiens* stathmin, transcript variant 3 (SEQ. ID. No. 3).

FIG. 14: shows the nucleic acid sequence of *Homo sapiens* stathmin, transcript variant 2, (SEQ. ID. NO. 4).

FIG. 15: shows the nucleic acid sequence of *Homo sapiens* stathmin, transcript variant 1, (SEQ. ID. No. 5).

FIG. 16: shows the nucleic acid sequence of *Homo sapiens* stathmin 1 (STMN1), transcript variant 4, (SEQ. ID. No. 6).

DETAILED DESCRIPTION

Compounds of Formula I

Figure 1:
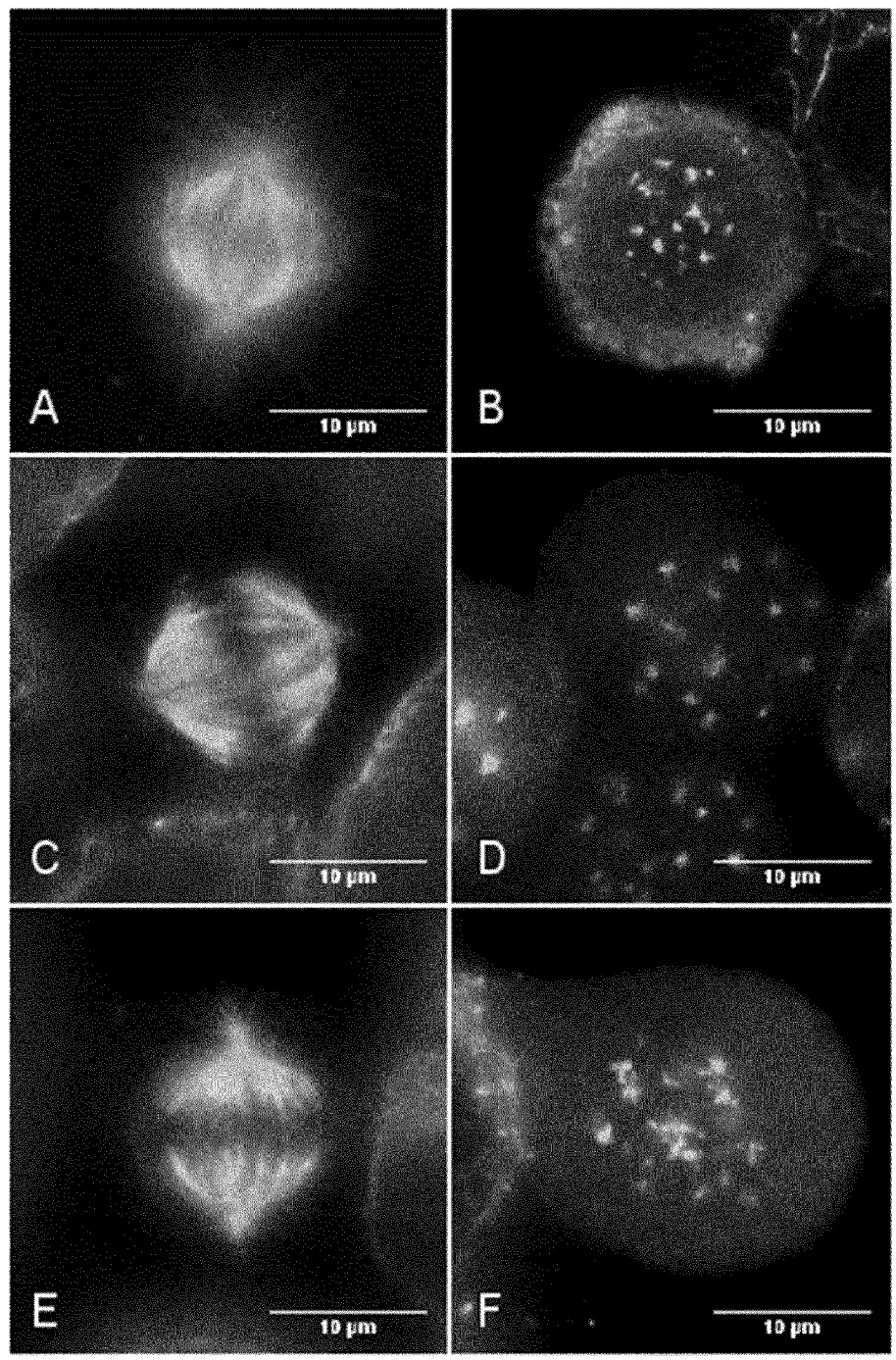
FIG. 1: Shows the treatment of human tumour cell lines from different histotypes with 50 nM BAL27862. The microtubules of mitotic or G2/M arrested cells were stained after 24 hours treatment with 50 nM BAL27862 or vehicle control.

The compounds according to the invention are represented by general formula I:

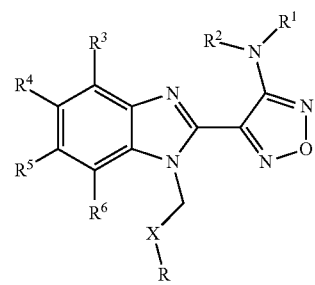

wherein

R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof, or wherein

R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof;

and wherein the prefix lower denotes a radical having up to and including a maximum of 7, especially up to and including a maximum of 4 carbon atoms.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, alkylcarbonyl, cyclohexylcarbonyl, arylcarbonyl, aryl-lower alkylcarbonyl, or heteroarylcarbonyl. Lower acyl is preferably lower alkylcarbonyl, in particular propionyl or acetyl.

Preferably, the compound of general formula I according to the invention is defined as wherein $R^1$ is selected from the group consisting of hydrogen, acetyl, $CH_2CH_2CN$ and $CH_2CH_2CH_2OH$.

In one preferred embodiment, the compound of general formula I according to the invention is selected from the group consisting of:
4-(1-Phenacyl-1H-benzimidazol-2-yl)-furazan-3-ylamine,
4-[1-(4-Bromophenacyl)-1H-benzimidazol-2-yl]-furazan-3-ylamine oxime,
N-{4-[1-(4-Chlorophenacyl)-1H-benzimidazol-2-yl]-furazan-3-yl}-acetamide,
4-[1-(4-Chlorophenacyl)-1H-benzimidazol-2-yl]-furazan-3-yl-N-(2-cyanoethyl)-amine,
4-[1-(4-Chlorophenacyl)-1H-benzimidazol-2-yl]-furazan-3-yl-N-(3-hydroxypropyl)-amine,
4-[1-(3-Amino-4-chlorophenacyl)-1H-benzimidazol-2-yl]-furazan-3-ylamine,
4-[1-(3-Methoxy-4-methoxymethoxy-phenacyl)-1H-benzimidazol-2-yl]-furazan-3-ylamine,
and pharmaceutically acceptable derivatives thereof.

In another preferred embodiment, the compound of general formula I according to the invention is:

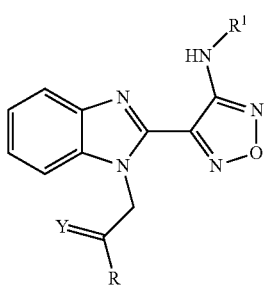

wherein
R, Y and $R^1$ are defined as follows:

| R | Y | $R^1$ |
|---|---|---|
| 4-Cl-C6H4 | O | H |
| C6H5 | NOH | H |
| C6H5 | NOMe | H |
| 4-MeO-C6H4 | O | H |
| 4-MeO-C6H4 | NOH | H |
| 4-Cl-C6H4 | NOH | H |
| 4-Cl-C6H4 | NOMe | H |
| 3-MeO-C6H4 | O | H |
| 3-MeO-C6H4 | NOH | H |
| 3-MeO-C6H4 | NOMe | H |
| 4-Ph-C6H4 | O | H |
| 4-Ph-C6H4 | NOH | H |
| 4-Ph-C6H4 | NOMe | H |
| 4-Br-C6H4 | O | H |

-continued

| R | Y | R¹ |
|---|---|---|
| 4-Br-C₆H₄- | NOMe | H |
| 2,4-Cl₂-C₆H₃- | O | H |
| 2-Cl-C₆H₄- | O | H |
| 2-Cl-C₆H₄- | NOH | H |
| 2-Cl-C₆H₄- | NOMe | H |
| 3-Cl-C₆H₄- | O | H |
| 3-Cl-C₆H₄- | NOH | H |
| 3-Cl-C₆H₄- | NOMe | H |
| 4-MeO-C₆H₄- | NOMe | H |
| 4-Et₂N-C₆H₄- | O | H |
| C₆H₅- | O | Ac |
| 4-F₃C-C₆H₄- | O | H |
| 4-Me-C₆H₄- | O | H |

-continued

| R | Y | R¹ |
|---|---|---|
| 3,4-methylenedioxy-C₆H₃- | O | H |
| 4-Br-C₆H₄- | O | CH₂CH₂CN |
| 4-MeO-C₆H₄- | O | CH₂CH₂CN |
| 4-O₂N-C₆H₄- | O | H |
| 4-H₂N-C₆H₄- | O | H |
| 3,4-Me₂-C₆H₃- | O | CH₂CH₂CH₂OH |
| 3,4-Me₂-C₆H₃- | O | H |
| 3,4-Me₂-C₆H₃- | O | CH₂CH₂CN |
| 4-Et-C₆H₄- | O | H |
| 4-Et-C₆H₄- | O | CH₂CH₂CN |
| 4-O₂N-C₆H₄- | O | CH₂CH₂CN |
| 4-H₂N-C₆H₄- | O | CH₂CH₂CN |
| 2-pyridyl | O | H |

-continued

| R | Y | R¹ |
|---|---|---|
|  | O | H |
| 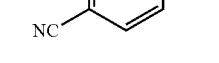 | O | H |
| 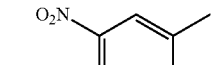 | O | H |
| 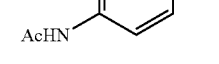 | O | H |
| 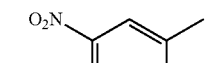 | O | H |
| 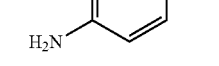 | O | H |
| 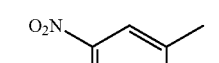 | O | H |
| 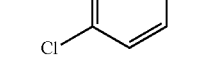 | O | CH$_2$CH$_2$CN |
| 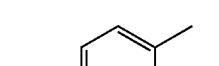 | O | H |
| 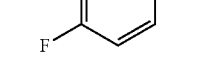 | O | H |
| 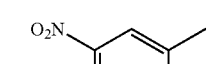 | O | H |
| 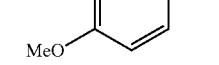 | O | H |
| 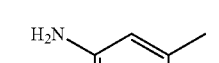 | O | H |

-continued

| R | Y | R¹ |
|---|---|---|
| 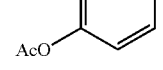 | O | H |
| 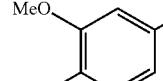 | O | H |
|  | O | H |
|  | O | H |
|  | O | CH$_2$CH$_2$CN |
| 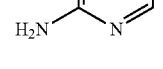 | O | H |
| 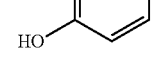 | O | H |
| 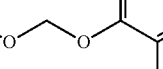 | O | CH$_2$CH$_2$CN | or pharmaceutically acceptable derivatives thereof.

In yet another preferred embodiment, the compound of general formula I according to the invention is selected from the group consisting of:

4-(1-Phenoxymethyl-1H-benzimidazol-2-yl)-furazan-3-ylamine,

4-[1-(4-Fluorophenoxymethyl)-1H-benzimidazol-2-yl]-furazan-3-ylamine,

4-[1-(3,4-Dimethylphenoxymethyl)-1H-benzimidazol-2-yl]-furazan-3-yl-N-(2-cyanoethyl)-amine, and compounds represented by the formula:

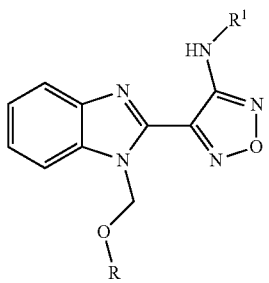

wherein R and R¹ are as defined below

| R | R¹ |
|---|---|
| 4-Cl-C₆H₄ | H |
| 4-Br-C₆H₄ | H |
| 4-MeO-C₆H₄ | H |
| 4-F₃C-C₆H₄ | H |
| 3,4-diCl-C₆H₃ | H |
| 4-Cl-C₆H₄ | CH₂CH₂CN |
| 4-Br-C₆H₄ | CH₂CH₂CN |
| C₆H₅ | CH₂CH₂CN |
| 4-OHC-C₆H₄ | H |
| 4-HOCH₂-C₆H₄ | H |
| 4-O₂N-C₆H₄ | H |
| 4-H₂N-C₆H₄ | H |
| 4-H₂N-C₆H₄ | H |
| 2,4-diMe-C₆H₃ | H |
| 3,5-di(CF₃)-C₆H₃ | H |
| 3-F₃C-C₆H₄ | H |
| 4-Me-C₆H₄ | CH₂CH₂CN |
| 2,4-diMe-C₆H₃ | CH₂CH₂CH₂OH |
| 6-Cl-pyridin-3-yl | H |
| 6-H₂N-pyridin-3-yl | H | or pharmaceutically acceptable derivatives thereof.

In still yet another preferred embodiment the compound of general formula I according to the invention is:

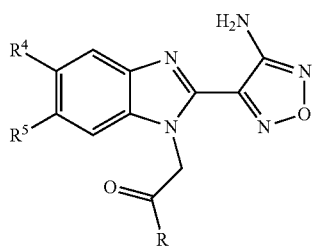

wherein R, $R^4$ and $R^5$ are as defined below

| R | $R^4$ | $R^5$ |
|---|---|---|
| phenyl | Me | Me |
| 4-Br-phenyl | Me | Me |
| 4-Cl-phenyl | Me | Me |
| 4-MeO-phenyl | Me | Me |
| 4-Ph-phenyl | Me | Me |
| phenyl | OMe | OMe |
| 4-Cl-phenyl | OMe | OMe |
| 4-Br-phenyl | OMe | OMe |
| 4-MeO-phenyl | OMe | OMe |
| 4-Ph-phenyl | OMe | OMe | or pharmaceutically acceptable derivatives thereof.

More preferably, the compound according to the invention is a compound of general formula I

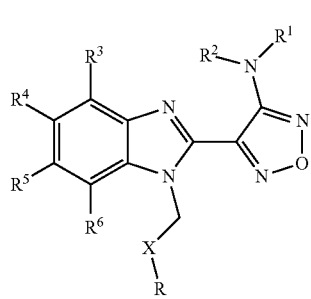

wherein

R represents phenyl or pyridinyl wherein phenyl is optionally substituted by one or two substituents independently selected from lower alkyl, lower alkoxy, amino, acetylamino, halogen and nitro; and wherein pyridinyl is optionally substituted by amino or halogen;

X represents a group C=O;

$R^1$ represents hydrogen or cyano-lower alkyl;

$R^2$, $R^3$, $R^4$, $R^5$ and $R^6$ represent hydrogen;

and pharmaceutically acceptable derivatives thereof, and wherein the prefix lower denotes a radical having up to and including a maximum of 7, especially up to and including a maximum of 4 carbon atoms.

Especially preferably, the compound according to the invention is represented by the following formula

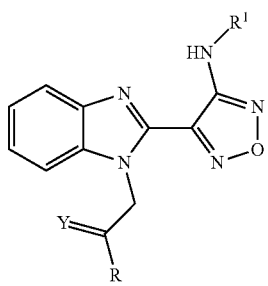

wherein R, Y and $R^1$ are defined as follows:

| R | Y | $R^1$ |
|---|---|---|
| 4-H$_2$N-phenyl | O | H |
| 4-H$_2$N-phenyl | O | CH$_2$CH$_2$CN |
| 6-H$_2$N-pyridin-3-yl | O | H |

-continued

| R | Y | R¹ |
|---|---|---|
| 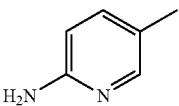 | O | CH₂CH₂CN | or pharmaceutically acceptable derivatives thereof.

More especially preferably, the compound according to the invention is represented by the following formula

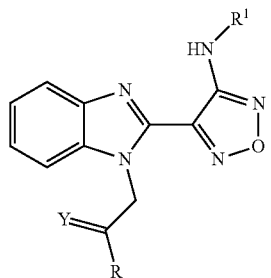

wherein R, Y and R1 are defined as follows:

| R | Y | R1 |
|---|---|---|
| 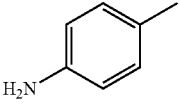 | O | CH₂CH₂CN |
| 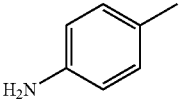 | O | H |
| 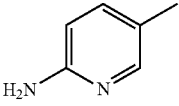 | O | CH₂CH₂CN | or pharmaceutically acceptable derivatives thereof.

Particularly preferably, the compound of general formula I according to the invention is

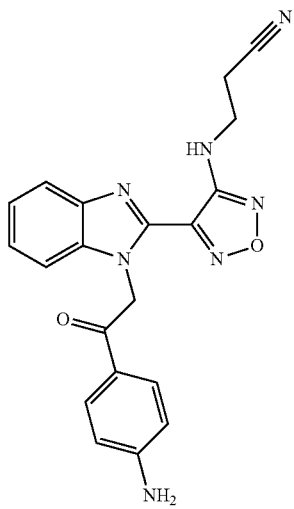

or pharmaceutically acceptable derivatives thereof.

The term derivative or derivatives in the phrase "pharmaceutically acceptable derivative" or "pharmaceutically acceptable derivatives" of compounds of general formula I relates to salts, solvates and complexes thereof and to solvates and complexes of salts thereof, as well as to pro-drugs, polymorphs, and isomers thereof (including optical, geometric and tautomeric isomers) and also salts of pro-drugs thereof. In a more preferred embodiment, it relates to salts and pro-drugs, as well as to salts of pro-drugs thereof.

Salts are preferably acid addition salts. Salts are formed, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compound according to the invention may be administered in the form of a pro-drug which is broken down in the human or animal body to give a compound of the formula I. Examples of pro-drugs include in vivo hydrolysable esters and amides of a compound of the formula I. Particular pro-drugs considered are ester and amides of naturally occurring amino acids and ester or amides of small peptides, in particular small peptides consisting of up to five, preferably two or three amino acids, as well as esters and amides of pegylated hydroxy acids, preferably hydroxy acetic acid and lactic acid. Pro-drug esters are formed from the acid function of the amino acid or the C terminal of the peptide and suitable hydroxy group(s) in the compound of formula I. Pro-drug amides are formed from the amino function of the amino acid or the N terminal of the peptide and suitable carboxy group(s) in the compound of formula I, or from the acid function of the amino acid or the C terminal of the peptide and suitable amino group(s) in the compound of formula I. Particularly preferably the pro-drug amides are formed from the amino group(s) present within the R group of formula I.

More preferably, the pro-drug is formed by the addition of glycine, alanine or lysine to the compound of formula I.

Even more preferably the compound of general formula I is in the form of a pro-drug selected from the compounds of formulae:

25
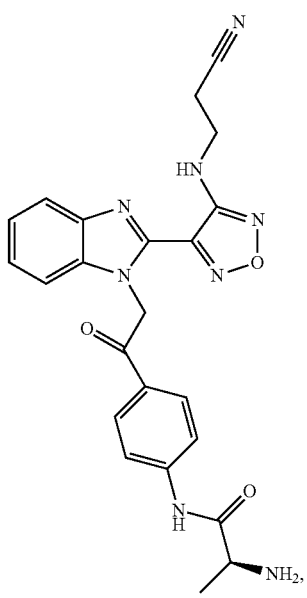
26
-continued
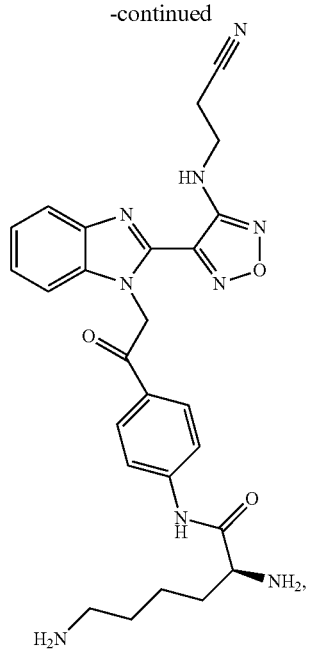
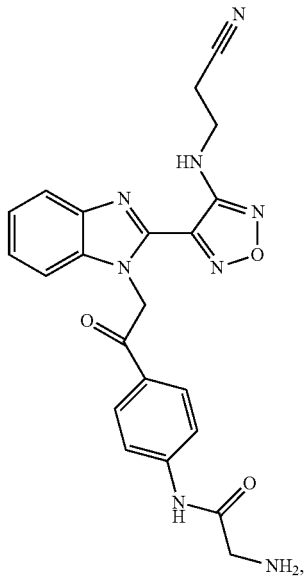
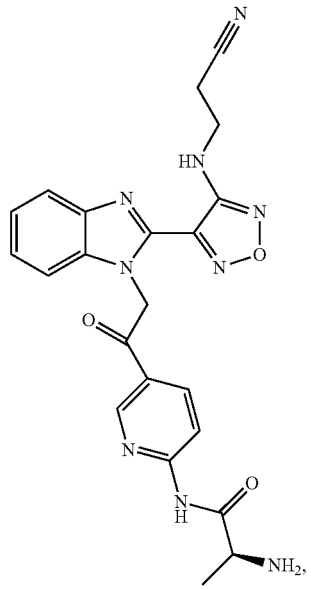

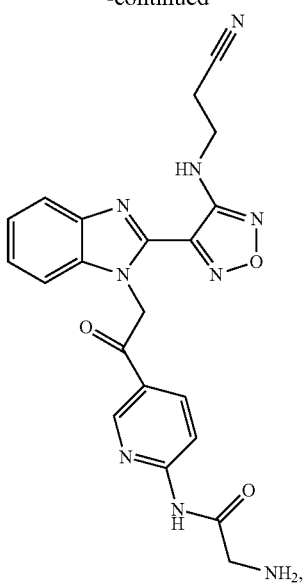
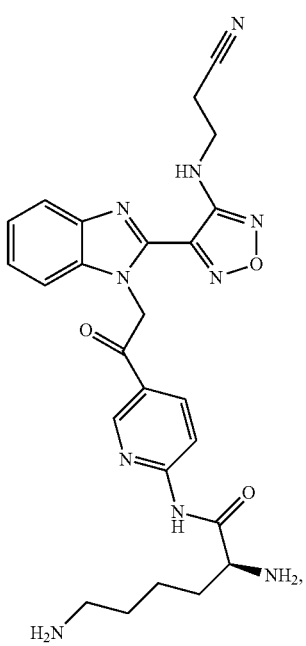
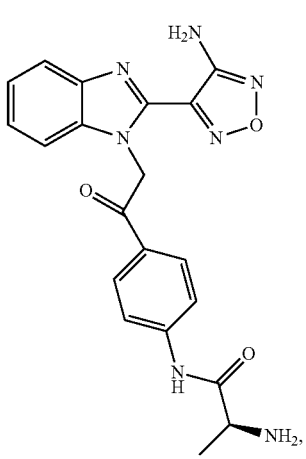
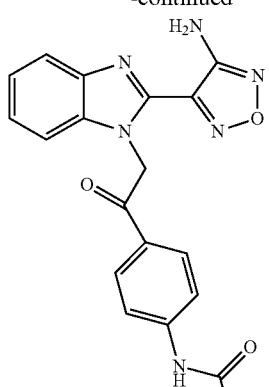
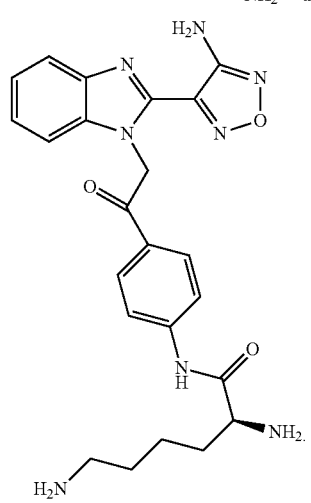
In an especially preferred embodiment the compound according to the invention is in the form of a pro-drug which has the following formula
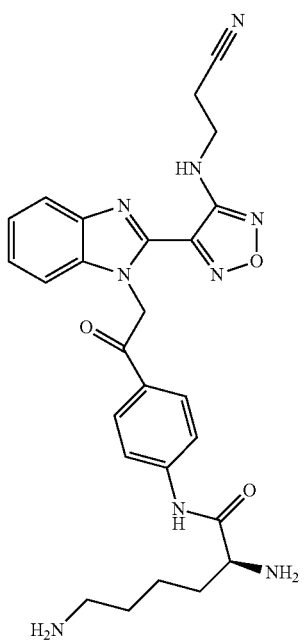 [SMILES: N#CCCNc1nonc1-c1nc2ccccc2n1CC(=O)c1ccc(NC(=O)[C@@H](N)CCCCN)cc1]

In a most especially preferred embodiment the compound according to the invention is a pharmaceutically acceptable salt, preferably a hydrochloride salt, most preferably a dihydrochloride salt, of a compound of the following formula

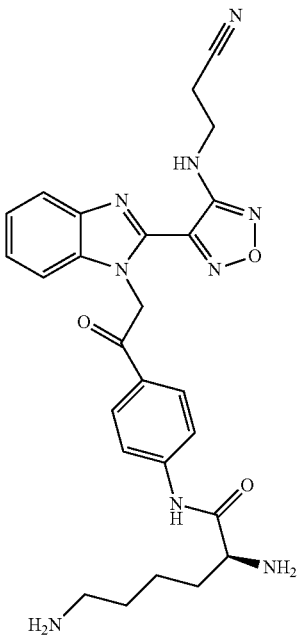 [SMILES: N#CCCNc1nonc1-c1nc2ccccc2n1CC(=O)c1ccc(NC(=O)[C@@H](N)CCCCN)cc1]

The pharmaceutically active metabolite in vivo in this case is BAL27862.

These pro-drugs may be prepared by processes that are known per se, in particular, a process, wherein a compound of formula (II)

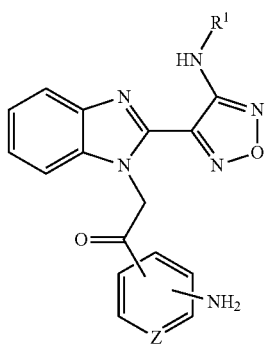

(II)

wherein $R^1$ is defined as for formula (I) and Z is CH or N, or a derivative of such a compound comprising functional groups in protected form,
or a salt thereof is
(1) acylated with an amino acid of formula (III)

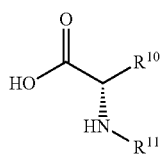

(III)

wherein
$R^{10}$ is selected from hydrogen (Gly); methyl (Ala) and protected aminobutyl (Lys) and $R^{11}$ is a suitable amino protecting group, and (2) any protecting groups in a protected derivative of the resulting compound are removed to yield a pro-drug as shown above, and, if so desired, (3) said pro-drug is converted into a salt by treatment with an acid, or a salt of a compound of formula (II) is converted into the corresponding free compound of formula (II) or into another salt, and/or a mixture of isomeric product compounds is separated into the individual isomers.

Acylation of a compound of formula (II) with an amino acid of formula (III) is performed in a manner known per se, usually in the presence of a suitable polar or dipolar aprotic solvent, with cooling or heating as required, for example in a temperature range from approximately minus 80° C. to approximately plus 150° C., more preferably from minus 30° C. to plus 120° C., especially in a range from approximately around 0° C. to the reflux temperature of the used solvent. Optionally a suitable base is added, in particular an aromatic base like pyridine or collidine or a tertiary amine base such as triethylamine or diisopropylethylamine, or an inorganic basic salt, e.g. potassium or sodium carbonate.

Acylation may be accomplished under conditions used for amide formation known per se in peptide chemistry, e.g. with activating agents for the carboxy group, such as carbodiimides like N,N'-diethyl-, N,N'-dipropyl-, N,N'-diisopropyl-, N,N'-dicyclohexylcarbodiimide and N-(3-dimethylaminoisopropyl)-N'-ethylcarbodiimide-hydrochloride (EDC), or with agents such as 1-hydroxybenzotriazole (HOBt), benzotriazol-1-yloxytris(dimethylamino)-phosphonium hexafluorophosphate (BOP), O-(7-aza-benzotriazol-1-yl)-N,N,N',N'-tetramethyl-uronium hexafluorophosphate (HATU), 2-(2-oxo-1-(2H)-pyridyl)-1,1,3,3-tetramethyluronium tetrafluoroborate (TPTU), optionally in the presence of suitable bases, catalysts or co-reagents. The carboxy group may also be activated as acyl halogenide, preferably as acyl chloride, e.g. by reaction with thionylchloride or oxalylchloride, or as symmetrical or unsymmetrical anhydride, e.g. by reaction with halogeno formates like ethyl chloroformate, optionally in the presence of suitable bases, catalysts or co-reagents.

If one or more other functional groups, for example carboxy, hydroxy or amino, are or need to be protected in a compound of formula (II) or (III), because they should not take part in the reaction, these are such protecting groups as are usually applied in the synthesis of amides like, in particular peptide compounds, cephalosporins, penicillins, nucleic acid derivatives and sugars, which are known to the skilled persons. Suitable protecting groups for amino groups are for example t-butyl carbamate, benzyl carbamate or 9-fluorenylmethyl carbamate.

The protecting groups may already be present in precursors and should protect the functional groups concerned against unwanted secondary reactions, such as alkylations, acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, G. M. Wuts "Protective Groups in Organic Synthesis", Wiley, New York, 2006.

Disease

The compounds of general formula I according to the invention have been shown to arrest cell proliferation and induce cell death, for example by apoptosis.

Deregulation of cell proliferation, or lack of appropriate cell death, has wide ranging clinical implications. A number of diseases associated with such deregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like.

Cancer is associated with abnormal cell proliferation and cell death rates. As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or reestablished in epithelial cells, in endothelial cells, in muscle cells, and in others which have lost contact with extracellular matrix.

A compound according to general formula I or pharmaceutically acceptable derivatives thereof may be used for the prophylactic or especially therapeutic treatment of the human or animal body, in particular for treating a neoplastic disease, autoimmune disease, transplantation related pathology and/or degenerative disease. Examples of such neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

The compounds of general formula I or pharmaceutically acceptable derivatives thereof may be used to treat autoimmune diseases. Examples of such autoimmune diseases include, but are not limited to, systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis/polymyositis, autoimmune hemolytic anemia, thrompocytopenic purpura, neutropenia, type I diabetes mellitus, thyroiditis (including Hashimoto's and Grave' disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopathic and secondary pulmonary fibrosis, inflammatory diseases with a possibility of autoimmune pathogensesis, such as pyoderma gangrensosum, lichen ruber, sarcoidosis (including Lofgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, HenochSchoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-vu (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells).

Particularly preferably, the disease according to the invention is a neoplastic or autoimmune disease. In an especially preferred embodiment the disease is cancer.

Examples of cancers in terms of the organs and parts of the body affected include, but are not limited to, the breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis. Preferably the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas. Especially preferably the cancer is selected from the group consisting of breast cancer, cervical cancer, gastric cancer, lung cancer and melanoma. More especially preferably the cancer is selected from the group consisting of gastric cancer, lung cancer and melanoma.

Samples

The measurement of the level of stathmin may be performed in vitro, on a sample of biological material derived from the subject. The sample may be any biological material separated from the body such as, for example, normal tissue, tumour tissue, cell lines, plasma, serum, whole blood, cerebrospinal fluid, lymph fluid, circulating tumour cells, cell lysate, tissue lysate, urine and aspirates. Preferably the sample is derived from normal tissue, tumour tissue, cell lines, circulating tumour cells, serum, plasma or whole blood. More preferably the sample is derived from tumour tissue, circulating tumour cells or serum. Even more preferably the sample is derived from tumour tissue or serum. In one particularly preferred embodiment the sample is derived from tumour tissue. For example, the level of stathmin may be measured in a fresh, frozen or formalin fixed/paraffin embedded tumour tissue sample. In another particularly preferred embodiment the sample is derived from serum.

The sample is pre-obtained from the subject before the sample is subjected to the method steps involving measuring the level of the biomarker. The methods for removal of the sample are well known in the art, and it may for example be removed from the subject by biopsy, for example by punch biopsy, core biopsy or aspiration fine needle biopsy, endoscopic biopsy, or surface biopsy. A whole blood, plasma or serum sample may be collected by venipuncture and further processed according to standard techniques. Circulating tumour cells may also be obtained from blood based on, for example, size (e.g. ISET—Isolation by Size of Epithelial Tumour cells) or immunomagnetic cell enrichment (e.g. CellSearch®, Veridex, Raritan, N.J.).

Sample Comparison

The subject according to the invention may be human or animal. Preferably the subject is human.

The biomarker stathmin is measured ex vivo in a sample or samples taken from the human or animal body, preferably taken from the human body. The sample or samples are pre-obtained from the human or animal body, preferably pre-obtained from the human body before the sample is subjected to the method steps involving measuring the level of the biomarker.

A biomarker is in general a substance that is used as an indicator of a biological response, preferably as an indicator of the susceptibility to a given treatment, which in the present application is treatment with a compound of general formula I or pharmaceutically acceptable derivatives thereof.

In a particularly preferred embodiment, higher stathmin levels in the sample relative to a standard value or set of standard values predicts resistance.

As used herein, an increase or relatively high or high or higher levels relative to a standard level or set of standard levels means the amount or concentration of the biomarker in a sample is detectably greater in the sample relative to the standard level or set of standard levels. This encompasses at least an increase of, or higher level of, about 1% relative to the standard, preferably at least an increase of about 5% relative to the standard. More preferably it is an increase of, or higher level of, at least about 10% relative to the standard. More particularly preferably it is an increase of, or higher level of, at least about 20% relative to the standard. For example, such an increase of, or higher level of, may include, but is not limited to, at least about 1%, about 10%, about 20%, about 30%, about 50%, about 70%, about 80%, about 100%, about 150% or about 200% or more relative to the standard.

Preferably, higher stathmin levels in a sample or samples
i) relative to a standard value or set of standard values from subjects with the same tumour histotype; or
ii) relative to a standard value or set of standard values from normal cells, tissue or body fluid;
are predictive of resistance.

The measuring of a level of stathmin is performed ex-vivo in a sample pre-obtained from the subject. Further preferably the response which is to be predicted is resistance.

Especially preferably, higher stathmin levels in a sample or samples relative to a standard value or set of standard values taken from subjects with the same tumour histotype are predictive of resistance.

In one preferred embodiment, for the case ii) where the measurement is compared in a sample or samples relative to a standard value or set of standard values taken from normal cells or tissue, the standard value or set of standard values may be established from a sample of normal (e.g. non-tumourous) cells, tissue or body fluid. Such data may be gathered from a population of subjects in order to develop the standard value or set of standard values.

In another preferred embodiment, for the case i) where the measurement is compared in a sample or samples relative to a standard value or set of standard values taken from samples from subjects with the same tumour histotype as the sample to which it is to be compared, the standard value or set of standard values are established from samples taken from a population of subjects with that cancer type. The samples from these standard subjects may for example be derived from the tumour tissue or from circulating tumour cells, serum, plasma or whole blood, as long as the origin of the sample is consistent between the standard and the sample to be compared. The standard value or set of standard values are established ex-vivo from pre-obtained samples which may be from cell lines, or preferably biological material taken from at least one subject and more preferably from an average of subjects (e.g., n=2 to 1000 or more). The standard value or set of standard values may then be correlated with the response data of the same cell lines, or same subjects, to treatment with a compound of general formula I or a pharmaceutically acceptable derivative thereof. From this correlation a comparator module, for example in the form of a relative scale or scoring system, optionally including cut-off or threshold values, can be established which indicates the levels of biomarker associated with a spectrum of response levels to the compound of formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. In a preferred embodiment this comparator module comprises a cut-off value or set of values which predicts resistance to treatment.

For example, if an immunohistochemical method is used to measure the level of stathmin in a sample, standard values may be in the form of a scoring system. Such a system might take into account the percentage of cells in which staining for stathmin is present. The system may also take into account the relative intensity of staining in the individual cells. The standard values or set of standard values of the level of stathmin may then be correlated with data indicating the response, especially resistance, of the subject or tissue or cell line to the therapeutic activity of a compound of formula I or a pharmaceutically acceptable derivative thereof. Such data may then form part of a comparator module.

Response is the reaction of the cell lines, or preferably of the subject, or more preferably of the disease in a subject, to the therapeutic activity of a compound of general formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. The response data may for example be monitored in terms of: objective response rates, time to disease progression, progression free survival, and overall survival.

The response of a cancerous disease may be evaluated by using criteria well known to a person in the field of cancer treatment, for example but not restricted to, Response Evaluation Criteria in Solid Tumors (RECIST) Guidelines, Source: Eisenhauer E A, Therasse P, Bogaerts J, Schwartz L H, Sargent D, Ford R, Dancey J, Arbuck S, Gwyther S, Mooney M, Rubinstein L, Shankar L, Dodd L, Kaplan R, Lacombe D, Verweij J. New response evaluation criteria in solid tumours: revised RECIST guideline (version 1.1). Eur J. Cancer. 2009; 45:228-47;

RANO Criteria for High-Grade Gliomas, Source: Wen P Y, Macdonald D R, Reardon D A, Cloughesy T F, Sorensen A G, Galanis E, Degroot J, Wick W, Gilbert M R, Lassman A B, Tsien C, Mikkelsen T, Wong E T, Chamberlain M C, Stupp R, Lamborn K R, Vogelbaum M A, van den Bent M J, Chang S M. Updated response assessment criteria for high-grade gliomas: response assessment in neuro-oncology working group. J Clin Oncol. 2010; 28(11):1963-72;

CA-125 Rustin Criteria for Ovarian Cancer Response, Source: Rustin G J, Quinn M, Thigpen T, du Bois A, Pujade-Lauraine E, Jakobsen A, Eisenhauer E, Sagae S, Greven K, Vergote I, Cervantes A, Vermorken J. Re: New guidelines to evaluate the response to treatment in solid tumors (ovarian cancer). J Natl Cancer Inst. 2004; 96(6): 487-8;

and

PSA Working Group 2 Criteria for Prostate Cancer Response, Source: Scher H I, Halabi S, Tannock I, Morris M, Sternberg C N, Carducci M A, Eisenberger M A, Higano C, Bubley G J, Dreicer R, Petrylak D, Kantoff P, Basch E, Kelly W K, Figg W D, Small E J, Beer T M, Wilding G, Martin A, Hussain M; Prostate Cancer Clinical Trials Working Group. Design and end points of clinical trials for patients with progressive prostate cancer and castrate levels of testosterone:recommendations of the Prostate Cancer Clinical Trials Working Group. J Clin Oncol. 2008; 26(7):1148-59.

Resistance is associated with there not being an observable and/or measurable reduction in, or absence of, one or more of the following: reduction in the number of abnormal cells, preferably cancerous cells or absence of the abnormal cells preferably cancerous cells; for cancerous diseases: reduction in tumour size; inhibition (i.e., slowed to some extent and preferably stopped) of further tumour growth; reduction in the levels of tumour markers such as PSA and CA-125, inhibition (i.e., slowed to some extent and preferably stopped) of cancer cell infiltration into other organs (including the spread of cancer into soft tissue and bone); inhibition (i.e., slowed to some extent and preferably stopped) of tumour metastasis; alleviation of one or more of the symptoms associated with the specific cancer; and reduced morbidity and mortality.

In a preferred embodiment resistance means there is no observable and/or measurable reduction in, or absence of, one or more of the following criteria: reduction in tumour size; inhibition of further tumour growth, inhibition of cancer cell infiltration into other organs; and inhibition of tumour metastasis.

In a more preferred embodiment resistance refers to one or more of the following criteria: no reduction in tumour size; no inhibition of further tumour growth, no inhibition of cancer cell infiltration into other organs; and no inhibition of tumour metastasis.

Measurement of the aforementioned resistance criteria is according to clinical guidelines well known to a person in the field of cancer treatment, such as those listed above for measuring the response of a cancerous disease.

Response may also be established in vitro by assessing cell proliferation and/or cell death. For example, effects on cell death or proliferation may be assessed in vitro by one or more of the following well established assays: A) Nuclear staining with Hoechst 33342 dye providing information about nuclear morphology and DNA fragmentation which are hallmarks of apoptosis. B) AnnexinV binding assay which reflects the phosphatidylserine content of the outer lipid bilayer of the plasma membrane. This event is considered an early hallmark of apoptosis. C) TUNEL assay (Terminal deoxynucleotidyl transferase mediated dUTP Nick End Labeling assay), a fluorescence method for evaluating cells undergoing apoptosis or necrosis by measuring DNA fragmentation by labeling the terminal end of nucleic acids. D) MTS proliferation assay measuring the metabolic activity of cells. Viable cells are metabolically active whereas cells with a compromised respiratory chain show a reduced activity in this test. E) Crystal violet staining assay, where effects on cell number are monitored through direct staining of cellular components. F) Proliferation assay monitoring DNA synthesis through incorporation of bromodeoxyuridine (BrdU). Inhibitory effects on growth/proliferation can be directly determined. G) YO-PRO assay which involves a membrane impermeable, fluorescent, monomeric cyanine, nucleic acid stain, which permits analysis of dying (e.g. apoptotic) cells without interfering with cell viability. Overall effects on cell number can also be analysed after cell permeabilisation. H) Propidium iodide staining for cell cycle distribution which shows alterations in distribution among the different phases of the cell cycle. Cell cycle arresting points can be determined. I) Anchorage-independent growth assays, such as colony outgrowth assays which assess the ability of single cell suspensions to grow into colonies in soft agar.

In a preferred embodiment relating to determination of resistance in vitro resistance means there is no decrease in the proliferation rate of abnormal cells and/or reduction in the number of abnormal cells. More preferably resistance means there is no decrease in the proliferation rate of cancerous cells and/or no reduction in the number of cancerous cells. The reduction in the number of abnormal, preferably cancerous, cells may occur through a variety of programmed and non-programmed cell death mechanisms. Apoptosis, caspase-independent programmed cell death and autophagic cell death are examples of programmed cell death. However the cell death criteria involved in embodiments of the invention are not to be taken as limited to any one cell death mechanism.

Stathmin

As described above, the term stathmin is used herein to encompass all the previously mentioned synonyms and isoforms and refers to this entity on both the nucleic acid and protein levels as appropriate. Nucleic acid levels refer to, for example mRNA, cDNA or DNA, and the term protein includes the translated polypeptide or protein sequence and post-translationally modified forms thereof.

Preferred examples of the protein sequence of stathmin (human stathmin) are listed in SEQ. ID No. 1 and 2 (isoform a and b respectively). However the term stathmin also encompasses homologues, mutant forms, allelic variants, isoforms, splice variants and equivalents of these sequences. The human homologues, mutant forms, allelic variants, isoforms, splice variants and equivalents of these sequences are more preferred embodiments. More preferably it encompasses sequences having at least about 75% identity, especially preferably at least about 85% identity, particularly preferably at least about 95% identity, and more particularly preferably about 99% identity, to either of the sequences represented by SEQ. ID. No. 1 or 2. In an especially preferred embodiment, stathmin is the entity on the nucleic acid or protein levels, which is represented on the protein level by SEQ ID NO. 1 or 2 or sequences having at least 95% identity with either of these sequences, preferably at least 99% identity with either of these sequences. In a particularly preferred embodiment, stathmin is the entity on the nucleic acid or protein levels, which is represented on the protein level by SEQ ID NO. 1 or sequences having at least 95% identity with this sequence, preferably at least 99% identity. In a more particularly preferred embodiment, stathmin is the entity on the nucleic acid or protein levels, which is represented on the protein level by SEQ ID NO. 1 or 2. In a still more particularly preferred embodiment, stathmin is the entity on the nucleic acid or protein levels, which is represented on the protein level by SEQ ID NO. 1.

Multiple splice variants of the human stathmin gene are known. Preferred examples of nucleic acid sequences of stathmin (human stathmin) are accessible via NCBI Reference Sequence NM_005563; NM_203399; NM_203401 and NM_001145454 and are listed in SEQ. ID. No. 3 (NM_005563.3); No. 4 (NM_203399.1); No. 5 (NM_203401.1) and No. 6 (NM_001145454.1) (FIGS. 13-16) respectively. These are *Homo sapiens* stathmin 1 (STMN1) transcripts variants 1-4. Transcript variants 1, 2 and 3 encode isoform a, while transcript variant 4 encodes isoform b.

The term stathmin also encompasses modifications, more degenerate variants of said sequences, complements of said sequences, and oligonucleotides that hybridise to one of said sequences. Such modifications include, but are not limited to, mutations, insertions, deletions, and substitutions of one or more nucleotides. More preferably it encompasses sequences having at least about 75% identity to said sequence, especially preferably at least about 85% identity, particularly preferably at least about 95% identity and more particularly preferably about 99% identity.

In yet another preferred embodiment, stathmin is the entity on the nucleic acid or protein levels, which is represented on the nucleic acid level by a sequence selected from the group consisting of SEQ ID NO. 3, 4, 5 and 6, and sequences having at least 95% identity with these sequences, preferably at least 99% identity with these sequences. More preferably, stathmin is the entity on the nucleic acid or protein levels, which is represented on the nucleic acid level by SEQ ID NO. 3, or sequences having at least 95% identity with this sequence, preferably at least 99% identity with this sequence. In a further preferred embodiment, stathmin is the entity on the nucleic acid or protein levels, which is represented on the nucleic acid level by a sequence selected from the group consisting of SEQ ID NO. 3, 4, 5 and 6.

Level of Stathmin

The level of stathmin may be assayed in the sample by technical means well known to a skilled person. It may be assayed at the transcriptional or translational level.

In one preferred embodiment the level of stathmin nucleic acid, preferably stathmin mRNA, in a sample is measured. Examples of methods of gene expression analysis known in the art which are suitable to measure the level of stathmin at the nucleic acid level include, but are not limited to, i) using a labelled probe that is capable of hybridising to mRNA; ii) using PCR involving one or more primers based on the stathmin gene sequence, for example using quantitative PCR methods using labelled probes, e.g. fluorogenic probes, such as quantitative real-time PCR; iii) micro-arrays; IV) northern blotting V) serial analysis of gene expression (SAGE), READS (restriction enzyme amplification of digested cDNAs), differential display and measuring microRNA.

In a preferred embodiment the level of stathmin at the protein level is measured. Examples of methods of protein expression analysis known in the art which are suitable to measure the level of stathmin at the protein level include, but are not limited to, i) immunohistochemistry (IHC) analysis, ii) western blotting iii) immunoprecipitation iv) enzyme linked immunosorbant assay (ELISA) v) radioimmunoassay vi) Fluorescence activated cell sorting (FACS) vii) mass spectrometry, including matrix assisted laser desorption/ionization (MALDI, e.g. MALDI-TOF) and surface enhanced laser desorption/ionization (SELDI, e.g. SELDI-TOF).

The antibodies involved in some of the above methods may be monoclonal or polyclonal antibodies, antibody fragments, and/or various types of synthetic antibodies, including chimeric antibodies. The antibody may be labelled to enable it to be detected or capable of detection following reaction with one or more further species, for example using a secondary antibody that is labelled or capable of producing a detectable result. Antibodies specific to stathmin are available commercially from Epitomics, Abcam, Cell Signaling Technology, Inc. and Santa Cruz or can be prepared via conventional antibody generation methods well known to a skilled person.

Preferred methods of protein analysis are ELISA, mass spectrometry techniques, immunohistochemistry and western blotting, more preferably ELISA, western blotting and immunohistochemistry, more particularly preferably western blotting and immunohistochemistry. In western blotting, also known as immunoblotting, labelled antibodies may be used to assess levels of protein, where the intensity of the signal from the detectable label corresponds to the amount of protein, and can be quantified for example by densitometry.

Immunohistochemistry again uses labelled antibodies to detect the presence and relative amount of the biomarker. It can be used to assess the percentage of cells for which the biomarker is present. It can also be used to assess the localisation or relative amount of the biomarker in individual cells; the latter is seen as a function of the intensity of staining.

ELISA stands for enzyme linked immunosorbant assay, since it uses an enzyme linked to an antibody or antigen for the detection of a specific protein. ELISA is typically performed as follows (although other variations in methodology exist): a solid substrate such as a 96 well plate is coated with a primary antibody, which recognises the biomarker. The bound biomarker is then recognised by a secondary antibody specific for the biomarker. This may be directly joined to an enzyme or a third anti-immunoglobulin antibody may be used which is joined to an enzyme. A substrate is added and the enzyme catalyses a reaction, yielding a specific colour. By measuring the optical density of this colour, the presence and amount of the biomarker can be determined.

Uses of Biomarker

The biomarker may be used to predict inherent resistance of the disease in a subject to the compound of general formula I or a pharmaceutically acceptable derivative thereof as defined above.

The biomarker may be used to select subjects suffering or predisposed to suffering from a disease, preferably cancer, for treatment with a compound of general formula I or a pharmaceutically acceptable derivative thereof as defined above. The levels of such a biomarker may be used to identify subjects likely to respond or to not respond to treatment with such agents. Stratification of subjects may be made in order to avoid unnecessary treatment regimes. In particular the biomarker may be used to identify subjects from whom a sample or samples do not display a higher level of stathmin, relative to a standard level or set of standard levels, whereupon such subjects may then be selected for treatment with the compound of formula I or a pharmaceutically acceptable derivative thereof as defined above.

The biomarker may also be used to assist in the determination of treatment regimes, regarding amounts and schedules of dosing. Additionally, the biomarker may be used to assist in the selection of a combination of drugs to be given to a subject, including a compound or compounds of general formula I or a pharmaceutically acceptable derivative thereof, and another chemotherapeutic (cytotoxic) agent or agents. Furthermore, the biomarker may be used to assist in the determination of therapy strategies in a subject including whether a compound of general formula I or a pharmaceutically acceptable derivative thereof is to be administered in combination with targeted therapy, endocrine therapy, radiotherapy, immunotherapy or surgical intervention, or a combination of these.

Stathmin may also be used in combination with other biomarkers to predict the response to a compound of general formula I or a pharmaceutically acceptable derivative thereof and to determine treatment regimes. It may furthermore be used in combination with chemo-sensitivity testing to predict resistance and to determine treatment regimes. Chemo-sensitivity testing involves directly applying a compound of general formula I to cells taken from the subject, for example from a subject with haematological malignancies or accessible solid tumours, for example breast, head and neck cancers or melanomas, to determine the response of the cells to the compound.

Method of Treatment

The invention also involves in some aspects a method of treatment and stathmin for use in a method of treatment, wherein the level of stathmin is first established relative to a standard level or set of standard levels and then a compound of general formula I or a pharmaceutically acceptable derivative thereof as defined above, is administered if the level of stathmin in said sample is not higher than a standard value or set of standard values. The compound of formula I or a pharmaceutically acceptable derivative thereof may be administered in a pharmaceutical composition, as is well known to a person skilled in the art. Suitable compositions and dosages are for example disclosed in WO 2004/103994 A1 pages 35-39, which are specifically incorporated by reference herein. Compositions for enteral administration, such as nasal, buccal, rectal or, especially, oral administration, and for parenteral administration, such as intravenous, intramuscular or subcutaneous administration, to warm-blooded animals, especially humans, are especially preferred. More particularly, compositions for intravenous administration are preferred.

The compositions comprise the active ingredient and a pharmaceutically acceptable carrier. An example of a composition includes, but is not limited to, the following: 5000 soft gelatin capsules, each comprising as active ingredient 0.05 g of one of the compounds of general formula (I), are prepared as follows: 250 g pulverized active ingredient is suspended in 2 liter Lauroglykol® (propylene glycol laurate, Gattefossé S. A., Saint Priest, France) and ground in a wet pulverizer to produce a particle size of about 1 to 3 µm. 0.419 g portions of the mixture are then introduced into soft gelatin capsules using a capsule-filling machine.

The invention also relates in one aspect to a method of treating a neoplastic or autoimmune disease, preferably cancer, by first decreasing the level of stathmin in a subject that has a sample with a higher level of stathmin compared to a standard level or set of standard levels, then treating the subject with a compound of general formula I or a pharmaceutically acceptable derivative as defined above. The level of stathmin may be decreased by direct or indirect chemical or genetic means. Examples of such methods are treatment with a drug that results in reduced stathmin expression, targeted delivery of viral, plasmid or peptide constructs or antibody or siRNA or antisense to downregulate the level of stathmin. For example siRNA may be used to reduce the level of stathmin expressed in a cell. The subject may then be treated with a compound of general formula I or a pharmaceutically acceptable derivative thereof.

A compound of general formula I or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents.

A compound of general formula I or a pharmaceutically acceptable derivative thereof can, besides or in addition, be administered especially for tumour therapy in combination with chemotherapy (cytotoxic therapy), targeted therapy, endocrine therapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemo-preventive therapy, for example in patients at risk.

Kit and Device

In one aspect the invention relates to a kit, and in another aspect to a device, for predicting the response, preferably of a disease in a subject, to a compound of general formula I or a pharmaceutically acceptable derivative thereof as defined above, comprising reagents necessary for measuring the level of stathmin in a sample. Preferably, the reagents comprise a capture reagent comprising a detector for stathmin and a detector reagent.

The kit and device may also preferably comprise a comparator module which comprises a standard value or set of standard values to which the level of stathmin in the sample is compared. In a preferred embodiment, the comparator module is included in instructions for use of the kit. In another preferred embodiment the comparator module is in the form of a display device, for example a strip of colour or numerically coded material which is designed to be placed next to the readout of the sample measurement to indicate resistance levels. The standard value or set of standard values may be determined as described above.

The reagents are preferably antibodies or antibody fragments which selectively bind to stathmin. These may for example be in the form of one specific primary antibody which binds to stathmin and a secondary antibody which binds to the primary antibody, and which is itself labelled for detection. The primary antibody may also be labelled for direct detection. The kits or devices may optionally also contain a wash solution(s) that selectively allows retention of the bound biomarker to the capture reagent as compared with other biomarkers after washing. Such kits can then be used in ELISA, western blotting, flow cytometry, immunohistochemical or other immunochemical methods to detect the level of the biomarker.

The reagents may also in another preferred embodiment be those that are capable of measuring the level of stathmin nucleic acids in a sample. Suitable samples are tissue or tumour samples, sections of fixed and paraffin-embedded or frozen tissue or tumour specimens, circulating tumour cells, and blood and body liquid-derived samples. Preferably, the reagents comprise a labelled probe or primers for hybridisation to stathmin nucleic acid in the sample. Suitable detection systems, either based on PCR amplification techniques or detection of labelled probes, allow quantification of stathmin nucleic acid in the sample. This can be done i) in-situ on the specimen itself, preferably in sections from paraffin-embedded or frozen specimens, ii) in extracts from tumour, tissue or blood-derived specimens, where suitable reagents selectively enrich for nucleic acids. The kits or devices enable the measurement and quantification of i) the amount of hybridized labelled probes to the specimens in-situ or ii) the amount of primer-based amplification products by methods based on specific physico-chemical properties of the probes itself or the reporters attached to the primers.

Furthermore the device may comprise imaging devices or measurement devices (for example, but not restricted to, measurement of fluorescence) which further process the measured signals and transfer them into a scale in a comparator module. More preferably the kit comprises a compound of general formula I, or a pharmaceutically acceptable derivative thereof as defined above. This compound may then be administered to the subject, in accordance with the level of the biomarker in the sample from the subject, as measured by the reagents comprised in the kit. Therefore the kit according to the invention may be used in the method of treatment according to the invention, as defined above. In an especially preferred embodiment the kit comprises a compound of the following formula or a pharmaceutically acceptable salt thereof

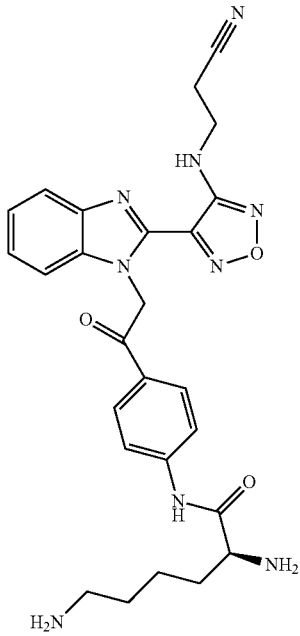 [SMILES: N#CCCNc1nonc1-c1nc2ccccc2n1CC(=O)c1ccc(NC(=O)[C@@H](N)CCCCN)cc1]

In a particularly preferred embodiment of the kit the pharmaceutically acceptable salt is a dihydrochloride salt. In another aspect the invention relates to the use of such a kit as described above.

In the present specification the words "comprise" or "comprises" or "comprising" are to be understood as to imply the inclusion of a stated item or group of items, but not the exclusion of any other item or group of items.

Experimental Methodology

Immunofluorescent Staining of Cultured Cells

A549 human non-small cell lung cancer (NSCLC, ATCC reference number CCL-185) cells, HeLa cervical cancer cells (ATCC reference number CCL-2) and SKBR3 breast carcinoma cells (ATCC reference number HTB-30) were seeded at densities of 50% on round microscope coverslips and cultured for 24 hours in RPMI-1640 containing 10% FCS (also referred to as FBS) at 37° C., 5% $CO_2$. Compounds to be tested were dissolved in DMSO. The cell culture medium was replaced with medium containing the diluted compound(s) (paclitaxel, vinblastine, colchicine and nocodazole were purchased from Sigma-Aldrich) or vehicle. After treatment for the times indicated in the Brief Description of the Figures, coverslips were washed and cells were fixed in methanol/acetone (1:1) for 5 minutes at room temperature and subsequently incubated in blocking buffer (0.5% BSA and 0.1% TX-100 in PBS) for 30 minutes at room temperature. Specimens were then incubated with anti-alpha-tubulin antibody (Sigma, 1:2000) for 1 hour at room temperature in blocking buffer. After several washing steps cells were incubated with AlexaFluor-488 goat-anti-mouse IgG (Molecular Probes, 1:3000) for 1 hour at room temperature followed by several washing steps with blocking buffer. Specimens were then mounted with ProLong Gold antifade (Molecular Probes), sealed with nail polish and examined with a Leica immunofluorescence microscope. Images were captured with a cooled CCD-camera and processed by ImageJ software.

Colony Outgrowth Assay:

Single cell suspensions of patient-derived tumour xenografts (maintained in nude mice) were prepared. For colony outgrowth assays, cells were plated in soft agar in 24-well plates according to the assay introduced by Hamburger & Salmon (Primary bioassay of human tumour stem cells, Science, 1977, 197:461-463). $2 \times 10^4$-$6 \times 10^4$ cells in 0.2 mL medium containing 0.4% agar were plated out on a bottom layer of 0.75% agar. Test compounds were applied in 0.2 mL culture medium. Every 24-well plate contained untreated controls and samples in triplicates. Cultures were incubated at 37° C. and 7.5% $CO_2$ for 5-28 days. 24 hours prior to analysis, vital colonies were stained with a solution of metabolizable tetrazolium salt (Alley M C et al, Life Sci. 1982, 31:3071-3078) and were counted with an automatic image analysis system (Omnicon 3600, Biosys GmbH).

Relative drug effects were expressed by the ratio of the mean number of colonies in the treated wells and the control wells. $IC_{70}$-values were determined by plotting compound concentrations versus relative colony counts.

Protein Extraction

Tumour extraction: tumours were extracted in ice-cold lysis buffer containing 50 mM HEPES (pH 7.5), 150 mM NaCl, 25 mM β-glycerophosphate, 25 mM NaF, 5 mM EGTA, 1 mM EDTA, 0.1% NP40, 15 mM pyrophosphate, 2 mM sodium orthovanadate, 10 mM sodium molybdate, leupeptin (10 μg/mL), aprotinin (10 μg/mL) and 1 mM PMSF (1 mL extraction volume per 45 mg tumour). After homogenisation by Polytron, lysates were adjusted to 1% NP40 and incubated on ice for 20 min. Lysates were clarified by centrifugation and frozen at −80° C.

Tumour cell line extraction: Cells were washed with ice-cold PBS containing 1 mM PMSF and with ice-cold lysis buffer (see above) without NP40. Cells were extracted in the same lysis buffer containing 1% NP40. After homogenisation, lysates were clarified by centrifugation and frozen at −80° C.

Immunoblotting/Western Blotting

Immunoblotting was performed using 20 µg of total protein per lane. Protein concentration was determined with the BCA Protein Assay (Pierce). Protein was separated on a 12.5% SDS-gel and transferred to a PVDF membrane using Semidry Blotting (90 min, 50 mA/gel). The primary antibodies used for immunoblotting were as follows:

Stathmin Ab. No 1: (available from Epitomics, reference number 1972-1) origin: rabbit, monoclonal, dilution 1:10,000, buffer conditions: 3% BSA in PBS/0.1% Tween Stathmin Ab. No 2: (available from Abcam, reference number ab47468) origin: rabbit, polyclonal, dilution 1:1000, buffer conditions: 3% BSA in PBS/0.1% Tween Actin: (available from Chemicon, reference number MAB1501) origin: mouse, monoclonal, dilution 1:5000, buffer conditions: 3% BSA in PBS/0.1% A Tween The secondary antibodies used for immunoblotting were peroxidase-conjugated goat anti-rabbit or goat anti-mouse (available from Jackson ImmunoResearch Laboratories INC: reference number 111-035-144 JIR and 115-035-146 JIR), dilution 1:5000, buffer conditions: 0.5% milk in PBS/0.1% Tween. Labelled bands were revealed using a Raytest Stella 3200 High Performance Imaging System.

Immunohistochemistry

Fixation of patient-derived tumour xenografts (maintained in nude mice) was performed in 10% neutral-buffered formalin containing 4% formaldehyde for 20-28 hours at room temperature. Fixed specimens were kept in a solution of 70% ethanol for a maximum of one week prior to dehydration and paraffin embedding according to a standard procedure, using the conditions listed below:

| Sequential Treatment | time (hours) |
|---|---|
| 70% EtOH | 1 |
| 80% EtOH | 2 |
| 99% EtOH | 1 |
| 100% Isopropanol | 0.5 |
| 100% Isopropanol | 1 |
| Xylol | 0.5 |
| Xylol | 1 |
| Xylol | 1 |
| Paraffin | 1 |
| Paraffin | 2 |
| Paraffin | 2 |

Paraffin sections of approximately 2 µm were cut and processed by using the automated immunostainer Benchmark XT® (Roche) running the standard processing steps. The visualisation of the specific antibody staining was done with DAB (3,3-diaminobenzidine) as chromogenic substrate at a concentration of 5 mg/ml. The following primary antibody and processing conditions were used for staining:

| Antibody | Processing |
|---|---|
| Anti-Stathmin(all isoforms), Cell Signaling Technology, Inc., #3352, rabbit polyclonal | Cell conditioning 1 buffer from Roche for 30 minutes, antibody incubation at 37° C. for 32 minutes at a dilution of 1:50000 |

ELISA Analysis of Serum

Mouse serum was prepared by collecting blood from isoflurane narcotised mice in a Microtainer SST tube (BD Transduction Laboratories, reference number 365968) and then processed according to the manufacturer's protocol. This included an incubation time of 30 minutes at room temperature, followed by centrifugation at 6000-15000 g for 1.5 minutes. Human serum was prepared by collecting blood from healthy human volunteers in a S-Monovette tube (Sarstedt, reference 02.1063), followed by centrifugation at 1250 g for 20 minutes. Serum supernatants were stored at −80° C. ELISA plate (Nunc, maxisorp) wells were coated with Stathmin rabbit monoclonal antibody (Epitomics, reference number 1972-1, 1:1000) in carbonate buffer pH 9.6 overnight at 4° C. After blocking the ELISA plate wells with PBS/1% BSA, serum samples were added pre-diluted in PBS and incubated overnight at 4° C. Stathmin was detected using a Stathmin mouse monoclonal antibody (available from Santa Cruz, reference number 55531, dilution 1:100) followed by a goat-anti-mouse HRP-labelled antibody (Jackson Immuno Research, 1:5000). Colour development using "SureBlue TMB Microwell Peroxidase Substrate" (TMB=3,3',5,5'-tetramethylbenzidine; KPL) was stopped after 5-10 minutes using TMB stop solution (KPL). Absorbance was measured at 450 nm in a SpectraMax 250 plate reader (Molecular Devices).

Stathmin protein concentration was calculated, after subtraction of the appropriate serum negative controls, from a standard curve derived from human recombinant stathmin (Calbiochem, reference number 569390), using GraphPad Prism software.

For experiments where human serum was 'spiked' with stathmin, human recombinant stathmin (Calbiochem, reference number 569390) was used. For the testing of serum derived from tumour-bearing mice, tumours were grown subcutaneously in nude mice until a size of 400-800 mm$^3$. Mice were sacrificed and serum prepared as defined above.

Quantitative Real-Time PCR

HeLa cervical cancer, A549 NSCLC and H460 NSCLC (ATCC reference number HTB-177) cells were grown in 10 cm-dishes until they reached 80% confluency, followed by trypsinisation, pelleting and resuspension in 1 ml Trizol reagent (Invitrogen). Total RNA was isolated according to manufacturer's instructions. Real-time PCR was performed using the TaqMan RNA-to-Ct 1-step kit (Applied Biosystems, reference number 4392938) and gene expression assays (Applied Biosystems) with 100 ng RNA per reaction using the ABI Prism 7000 Sequence Detection System. The following gene expression assays were used: Assay ID HS01027515_gH for quantification of stathmin or Assay ID HS99999901_s1 for quantification of 18S-RNA. All samples were analysed in triplicate. Data analysis was performed using SDS software (Applied Biosystems). Stathmin expression levels were normalised to 18S-RNA.

DETAILED EXAMPLES

Example 1

A Distinct Mitotic Phenotype Induced by Compounds of General Formula I

Figure 2:
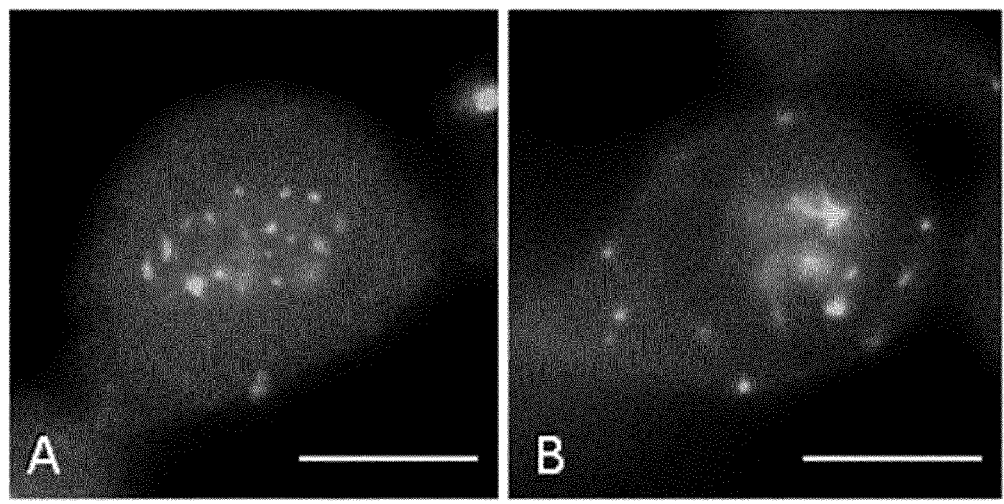
FIG. 2: Shows the treatment of A549 NSCLC cells with the Compounds B and C. The microtubules of mitotic or G2/M arrested A549 NSCLC cells were stained after 24 hours treatment with 80 nM or 20 nM of Compounds B and C, respectively. The white scale bar represents 10 micrometers.
Figure 3:
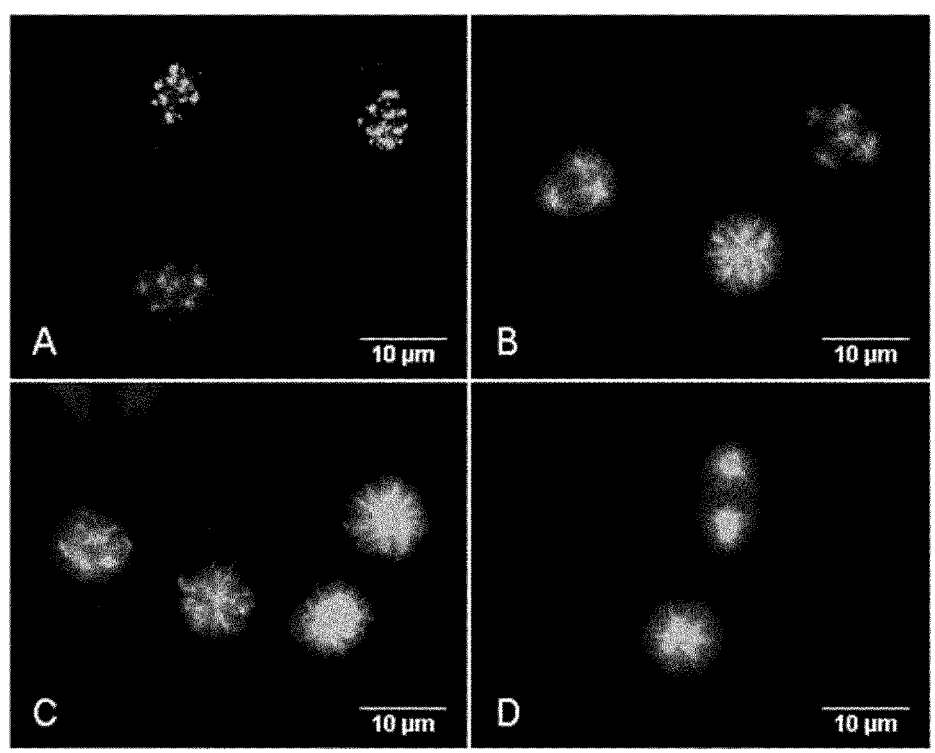
FIG. 3: Shows a comparison of treatment of cells with BAL27862 compared to conventional microtubule targeting agents. Microtubules of mitotic or G2/M arrested A549 NSCLC cells were stained after 24 hours of treatment with 50 nM of A: BAL27862; B: vinblastine; C: colchicine; D: paclitaxel. Stacks of images taken every 1 μm were processed by using ImageJ software.
Figure 4:
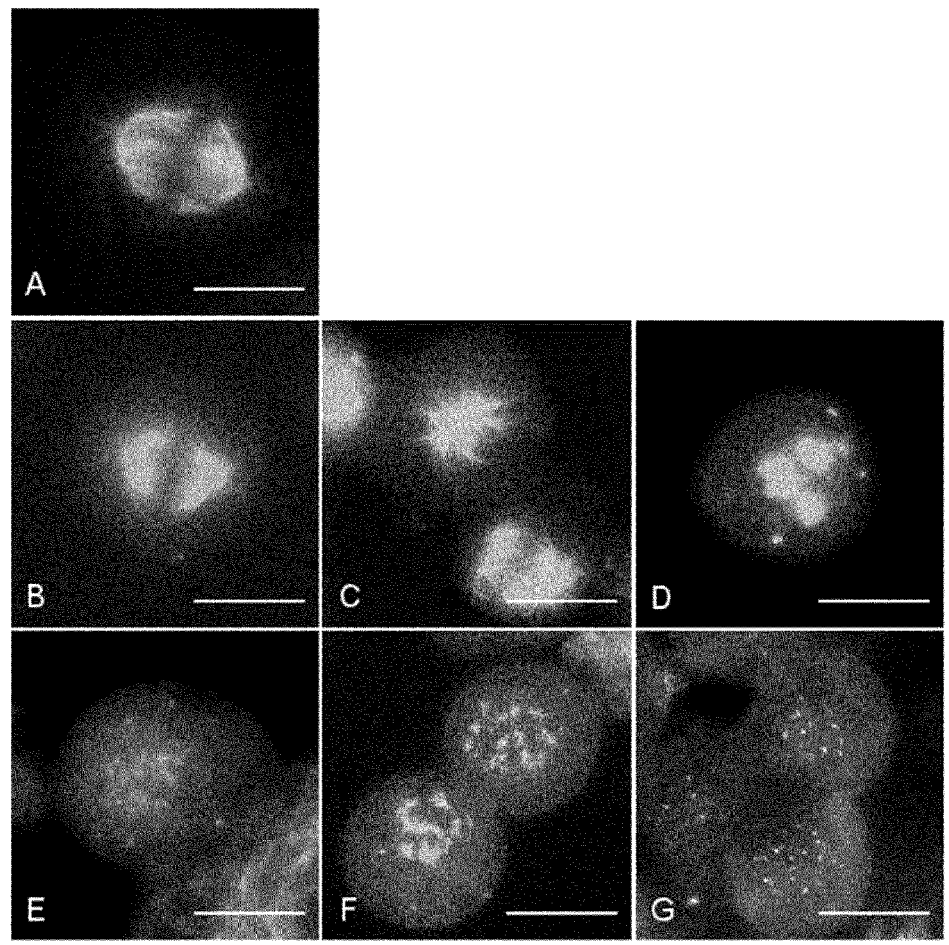
FIG. 4: Shows a comparison of treatment of A549 NSCLC cells with BAL27862 compared to nocodazole. Microtubules of mitotic or G2/M arrested cells were stained after 24 h of treatment with various concentrations of nocodazole (B, C & D) and BAL27862 (E, F & G). A: control, B: Nocodazole 50 nM, C: Nocodazole 100 nM, D: Nocodazole 200 nM, E: BAL27862 20 nM; F: BAL27862 30 nM and G: BAL27862 50 nM. The white scale bar represents 10 micrometers. Representative images of the microtubule phenotypes observed are shown.

Treatment with compound A (BAL27862) or with compound B, or compound C induced a highly reproducible and distinct microtubule phenotype in all tumour cell lines tested (shown for BAL27862 in A549, HeLa and SKBR3 cells in FIG. 1, and for compound C and compound B in A549 cells in FIG. 2). In dividing cells an apparent fragmentation of the mitotic spindle occurred, resulting in the formation of dot-like structures (FIG. 1). This phenotype was shown to be distinct from that observed with conventional microtubule targeting agents, such as the microtubule stabiliser paclitaxel and the microtubule destabilisers vinblastine and colchicine (FIG. 3) and nocodazole (FIG. 4).

Example 2

Figure 5:
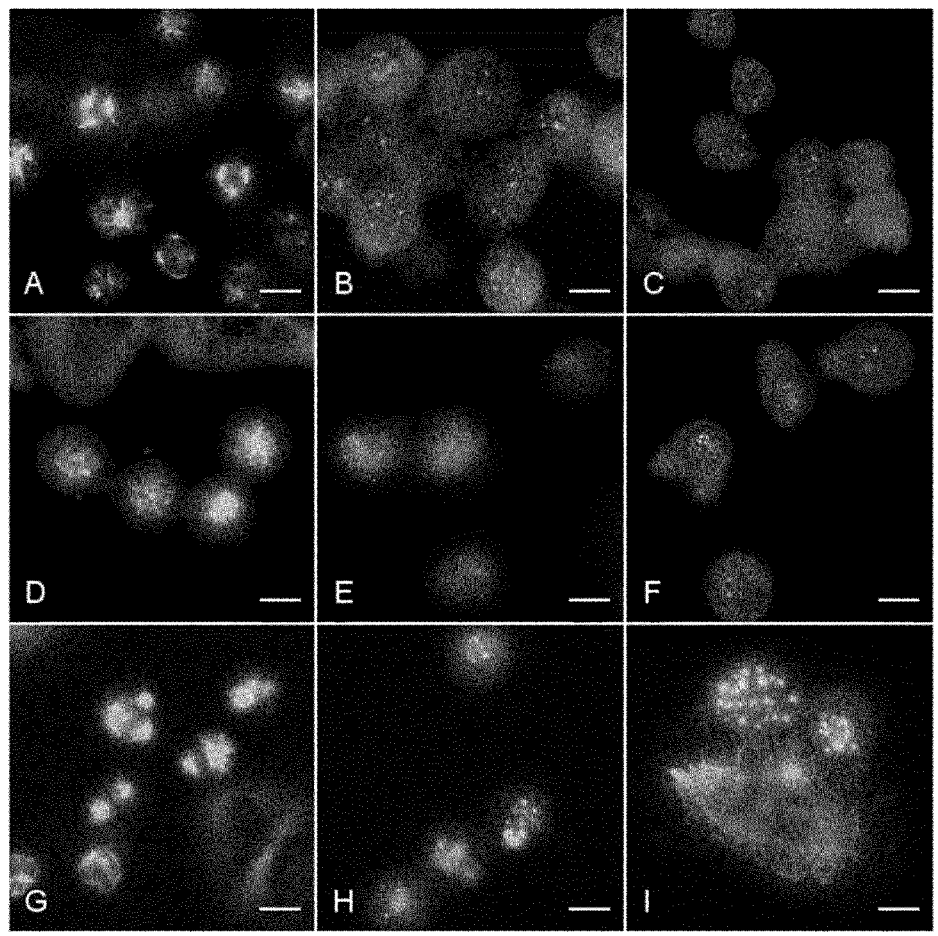
FIG. 5: Shows a combination of treatment with BAL27862 and conventional microtubule-targeting agents. Microtubules of mitotic or G2/M arrested A549 NSCLC cells were stained after treatment for the times indicated below. 50 nM BAL27862, 50 nM vinblastine, 50 nM colchicine and 25 nM paclitaxel were used. The white scale bar represents 10 micrometers.
Figure 6:
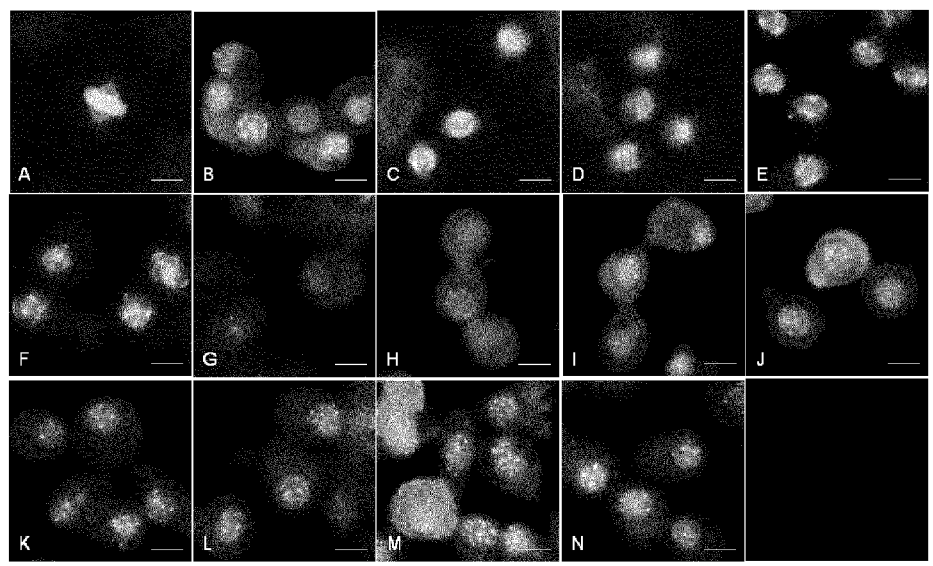
FIG. 6: Shows a combination of treatment with BAL27862 and nocodazole. Microtubules of mitotic or G2/M arrested A549 NSCLC cells were stained after treatment for the times indicated below. 25 nM BAL27862 and nocodazole at the concentrations indicated below were used. The white scale bar represents 10 micrometers.

BAL27862 Overcomes Microtubule Phenotype Induced by Conventional Microtubule-Targeting Drugs in a Dominant Fashion In order to show the uniqueness of its activity on microtubules, BAL27862 was tested in combination with vinblastine, colchicine and paclitaxel (FIG. 5) and nocodazole (FIG. 6) using A549 cells. Treatment with vinblastine, colchicine, paclitaxel or nocodazole alone induced the mitotic microtubule phenotypes characteristic of these agents. However, combination treatment with BAL27862 for the last 4 hours resulted in disruption of the microtubule structures; creating a phenotype consistent with treatment of BAL27862 alone, despite the continued presence of vinblastine, colchicine, paclitaxel or nocodazole. In contrast, treating first with BAL27862 and subsequently for 4 hours in combination with vinblastine, colchicine, paclitaxel or nocodazole had no impact on the observed microtubule phenotype that was consistent with treatment with BAL27862.

These data demonstrate that compounds of formula I affect microtubule biology consistently, but in a different manner than conventional microtubule targeting agents.

DETAILED EXAMPLES ACCORDING TO THE INVENTION

Example 3

Association of High Stathmin Expression Levels with Patient-Derived Tumour Cells Highly Resistant to BAL27862 Treatment Based on colony outgrowth assays, using tumour cells derived from patient-derived tumours maintained as xenografts in mice, BAL27862-sensitive or highly resistant tumour cells were identified from melanoma and gastric and lung cancer (see Table 1). Concentrations at which 70% growth inhibition was observed versus controls ($IC_{70}$) are shown in Table 1. In this table, BAL27862-sensitive tumour cells were those that had $IC_{70}$ values in the low nanomolar range, while BAL27862-resistant tumour cells had $IC_{70}$ values >600 nanomolar. Paclitaxel and vinblastine data, using the same ex vivo assay, was available for 6 of the 7 tumour models. Of these 6 models, all were resistant to treatment with paclitaxel, while 5 were sensitive to treatment with vinblastine.

TABLE 1

| Cancer type | name | Response to BAL27862 | $IC_{70}$ BAL27862 [microM] | Response to paclitaxel | Response to vinblastine |
| --- | --- | --- | --- | --- | --- |
| Gastric | GXF 251 | sensitive | 0.485 | resistant | sensitive |
| Gastric | GXF 97 | resistant | >3.5 | resistant | sensitive |
| Lung | LXFE211 | sensitive | 0.021 | esistant | sensitive |
| Lung | LXFE397 | resistant | >3.5 | Not known | Not known |
| melanoma | MEXF 1341 | sensitive | 0.025 | resistant | sensitive |
| melanoma | MEXF 276 | resistant model 1 | >3.5 | resistant | sensitive |
| melanoma | MEXF 989 | resistant model 2 | >3.5 | resistant | resistant |

Figure 7:
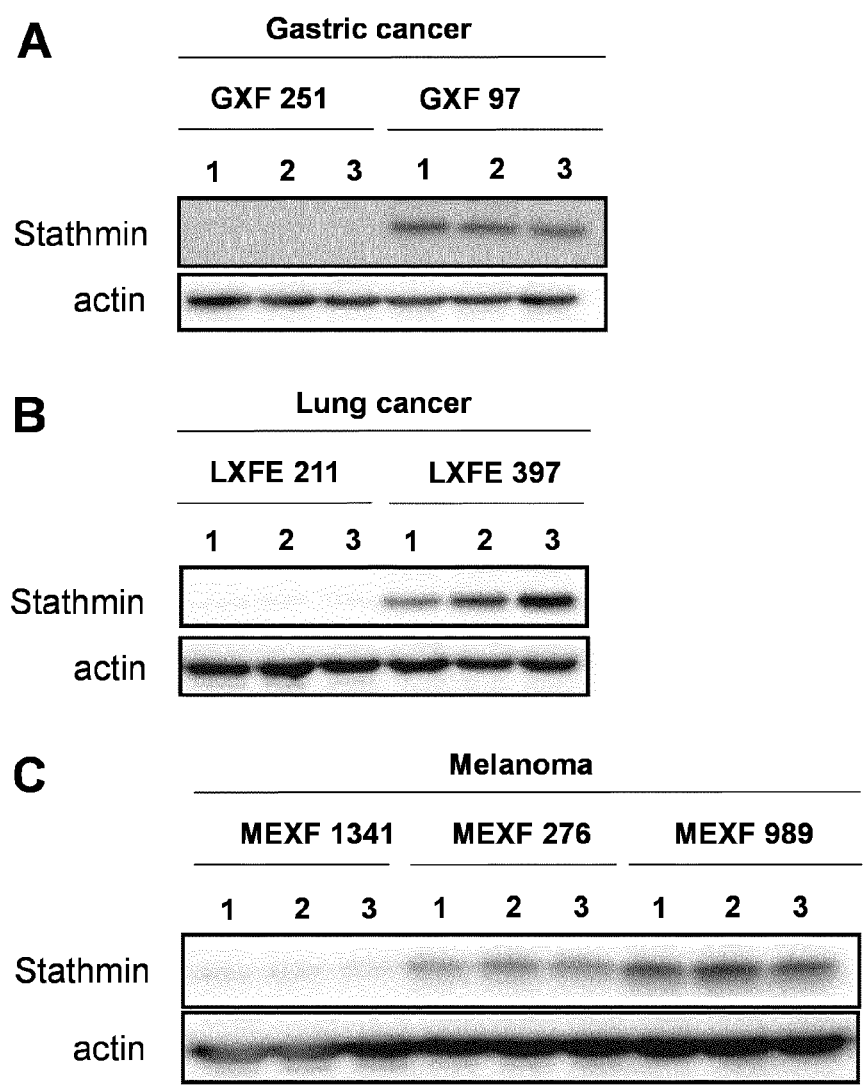
FIG. 7: Protein extracts were prepared from patient-derived gastric cancer (FIG. 7A) and lung cancer (FIG. 7B) and melanoma (FIG. 7C) tumours obtained from subcutaneously xenografted mice, and analysed by immunoblotting for stathmin expression, with actin included as a loading control. Three independent tumours were analysed in each case (1-3). BAL27862, paclitaxel and vinblastine resistance and sensitivity is as defined in Table 1.

Immunoblotting analysis was then performed in order to measure stathmin levels in the same tumours maintained as xenografts, using two antibodies (shown in FIG. 7 with the antibody obtained from Abcam). The actin levels were included on the immunoblot as a loading control.

Analysis of stathmin levels indicated that stathmin protein expression varied dramatically across all the tumours measured (FIG. 7).

Based on the colony outgrowth assay and the same $IC_{70}$ criteria, there was no association between paclitaxel or vinblastine resistance and high stathmin expression levels. This lack of correlation can, for example, be seen with the gastric model. Although GXF 251 and GXF 97 were both resistant to paclitaxel, for GXF 251 the stathmin levels were virtually undetectable, while for GXF 97 the levels were comparably higher. The same lack of association was true for the vinca alkaloid, vinblastine, in the gastric models, since both these tumours were sensitive to vinblastine. Thus stathmin levels were shown to be unsuitable as a reliable biomarker of resistance to the conventional microtubule agents paclitaxel and vinblastine in patient-derived tumour models.

Surprisingly, in contrast, when the BAL27862 resistance data, as defined by the colony outgrowth assay, was compared with the stathmin level, stathmin expression was shown to be higher only in the resistant tumours and not in the sensitive tumours derived from the same tumour histotype. Increased expression levels were therefore consistently indicative of resistance to BAL27862. Thus stathmin levels were shown to be a biomarker of resistance for the compound according to the invention, BAL27862.

Example 4

Immunohistochemical Analysis of Gastric Tumour Xenografts

Figure 8:
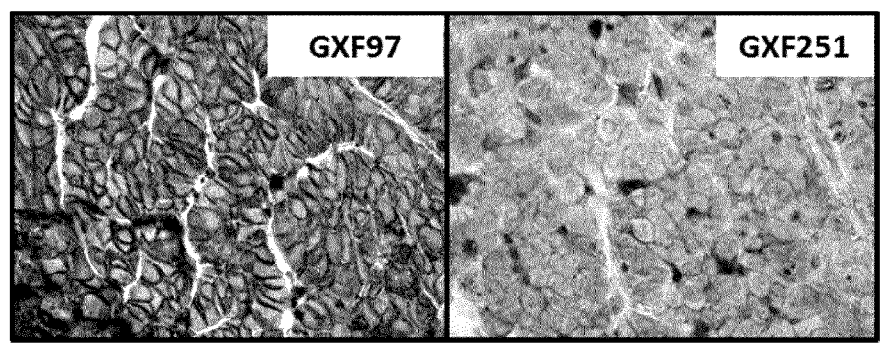
FIG. 8: Immunohistochemical analysis of stathmin levels in a patient-derived xenografted gastric tumour. GXF 251: BAL27862 sensitive; GXF 97: BAL27862 resistant. BAL27862, paclitaxel and vinblastine resistance and sensitivity is defined in Table 1.

Immunohistochemical analysis was performed on the gastric tumour xenografts (FIG. 8), revealing a high expression of stathmin in the tumour model GXF 97. Again a clear correlation was seen between high expression levels of stathmin and resistance to BAL27862 (tumour model GXF 97 was BAL27862-resistant, while tumour model GXF 251 was BAL27862-sensitive; as defined by the colony outgrowth assay). Thus stathmin protein expression levels were again shown to be a biomarker of resistance for the compound according to the invention, BAL27862.

Example 5

Detection of Stathmin in Serum

Figure 9:
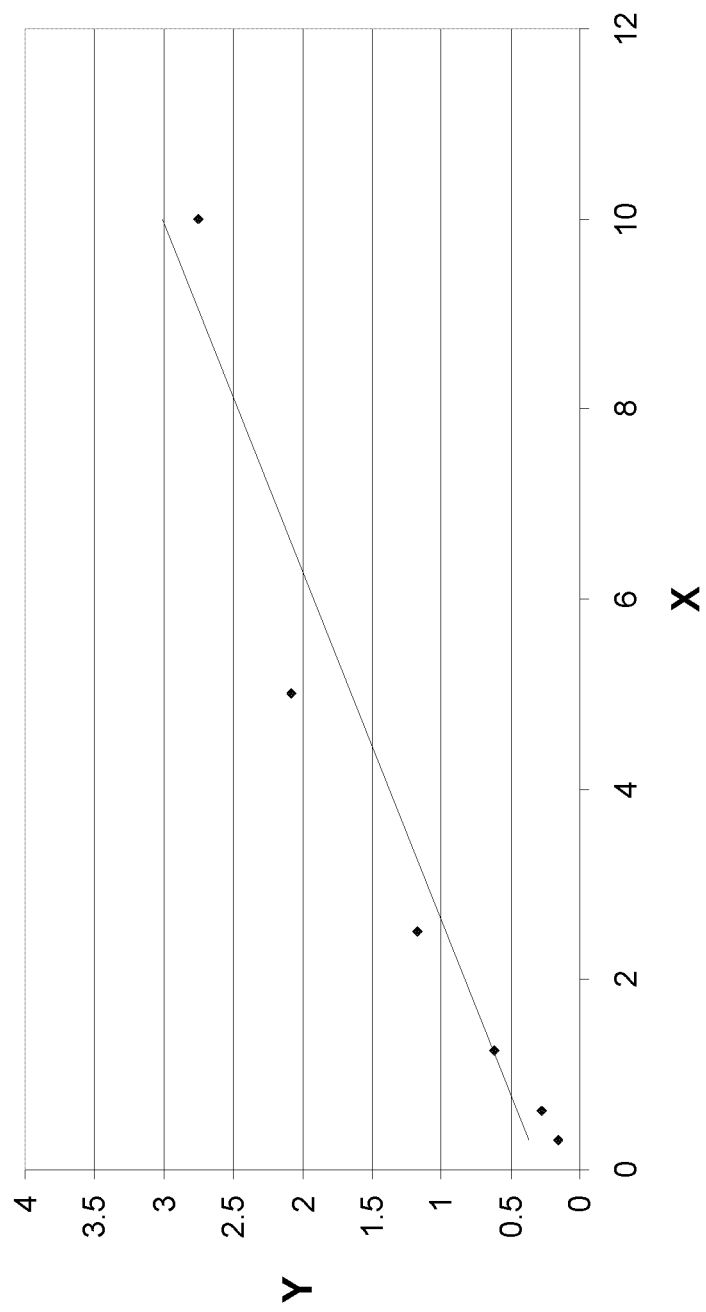
FIG. 9: Standard curve for ELISA quantification of stathmin in human serum spiked with recombinant stathmin. (See FIG. 10). Y axis=Optical Density at 450 nm, X axis=stathmin concentration (ng/mL). y=0.2723x+0.2806, $R^2$=0.9314.
Figure 10:
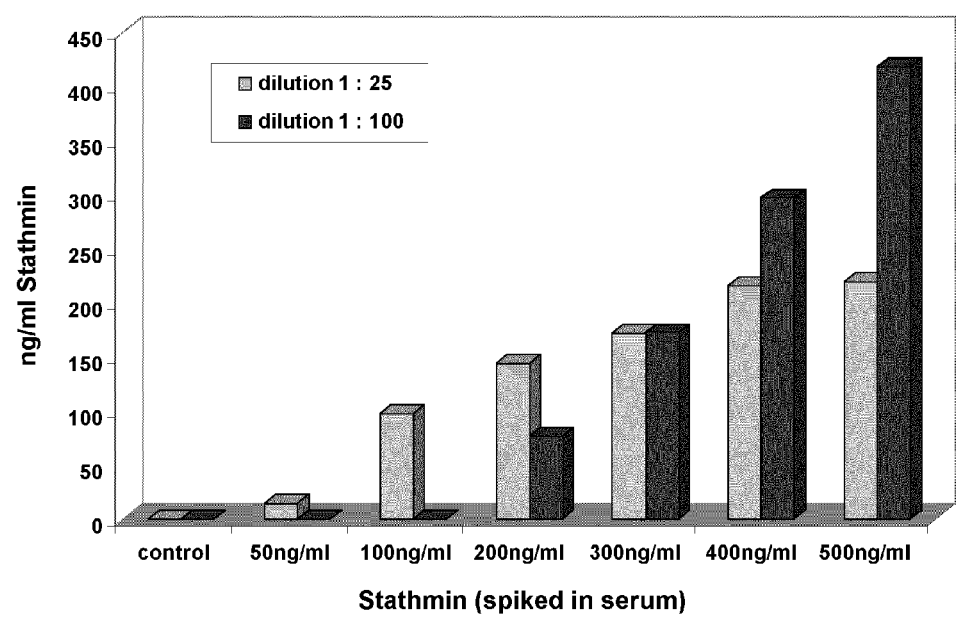
FIG. 10: ELISA analysis of stathmin-spiked human serum. Actual concentrations measured (y axis) were calculated based on the standard curve in FIG. 9.

Serum prepared from healthy human volunteer blood was spiked with known amounts of recombinant stathmin, followed by ELISA analysis at a dilution of 1:25 and 1:100. Based on a standard curve produced at the same time (FIG. 9), stathmin concentrations were calculated as presented in FIG. 10. The data show that, although there is a general underestimation of the spiked stathmin concentration, a 1:25 dilution is required to resolve lower stathmin concentrations <300 ng/ml, whereas a 1:100 dilution is required to resolve higher concentrations >300 ng/ml. Strikingly, when serum was prepared from mice bearing the tumours listed in Table 1 (2 mice per tumour type were used), and analysed at a dilution of 1:25, only mice bearing tumours derived from resistant cells had evidence of elevated serum stathmin levels (Table 2).

TABLE 2

| Cancer type | name | Sensitivity or resistance to BAL27862 | mouse | Serum stathmin conc. ng/ml |
|---|---|---|---|---|
| Gastric | GXF 251 | sensitive | 1 | 0 |
|  |  |  | 2 | 0 |
| Gastric | GXF 97 | resistant | 1 | 8 |
|  |  |  | 2 | 0 |
| Lung | LXFE211 | sensitive | 1 | 0 |
|  |  |  | 2 | 0 |
| Lung | LXFE397 | resistant | 1 | 3 |
|  |  |  | 2 | 0 |
| melanoma | MEXF 1341 | sensitive | 1 | 0 |
|  |  |  | 2 | 0 |
| melanoma | MEXF 276 | resistant model 1 | 1 | 33 |
|  |  |  | 2 | 0 |
| melanoma | MEXF 989 | resistant model 2 | 1 | 0 |
|  |  |  | 2 | 0 |

Example 6

Stathmin RNA Expression Levels Versus Protein Expression Levels

Figure 11:
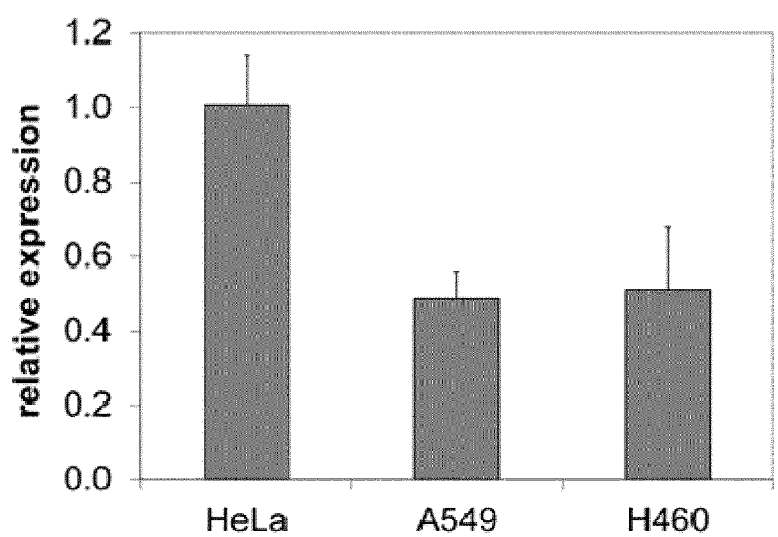
FIG. 11: Shows that for stathmin, protein levels in tumour cells are reflected by its RNA expression levels.
Figure 11:
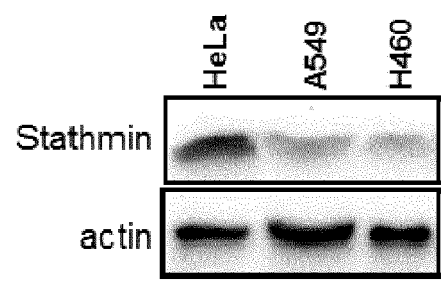

In order to show that stathmin RNA expression levels reflect protein expression levels, and hence that RNA expression levels can be used in the prediction of resistance to BAL27862, stathmin expression levels were measured on both the RNA and protein levels as follows. Whole cell protein extracts were prepared from HeLa, H460 and A549 cell lines and analysed by immunoblot for stathmin protein expression (FIG. 11B). RNA samples were prepared from the same cell passage, and quantitative RT-PCR was performed. (FIG. 11A). Comparison of the immunoblot data (FIG. 11B) and the RT-PCR data (FIG. 11A), indicated that there was a good correlation between protein and RNA expression levels for stathmin in these lines.

LIST OF ABBREVIATIONS

A549 human non-small cell lung cancer cell line
AnnexinV phosphatidylserine-binding protein
BCA bicinchoninic acid
Bcl-2 B-cell lymphoma 2 protein
BRCA1 breast cancer type 1 susceptibility protein
BrdU bromodeoxyuridine
BSA bovine serum albumin
CA-125 cancer antigen 125
cDNA complementary deoxyribonucleic acid
$CO_2$ carbon dioxide
CREST limited scleroderma syndrome
DAB 3,3-diaminobenzidine
DMSO dimethylsulphoxide
DNA deoxyribonucleic acid
dUTP 2'-Deoxyuridine 5'-Triphosphate
EDTA Ethylenediaminetetraacetic acid
EGTA Ethyleneglycol-bis(β-aminoethyl)-N,N,N',N'-tetraacetic acid
ELISA enzyme-linked immunosorbent assay
ErbB-2 human epidermal growth factor receptor
EtOH Ethanol
FACS fluorescence activated cell scan/sorting
FCS/FBS foetal calf/foetal bovine serum
G2/M transition from G2 to the mitotic phase in the cell cycle
GXF251 patient-derived gastric tumour
GXF97 patient-derived gastric tumour
HeLa human squamous cell cancer cell line
HEPES 4-(2-Hydroxyethyl)piperazine-1-ethanesulphonic acid
Hoe33342 2'-(4'-Ethoxyphenyl)-5-(4-methylpiperazin-1-yl)-2,5'-bis-1H-benzimidazole trihydrochloride trihydrate
Horseradish peroxydase
HRPH460 human non-small cell lung cancer cell line
IgG immunoglobulin G
ih Immunohistochemistry
LXFE211 Patient-derived lung cancer
LXFE397 Patient-derived lung cancer
MALDI matrix-assisted-laser-desorption/ionisation mass-spectrometry
MALDI-TOF matrix-assisted-laser-desorption/ionisation—time-of-flight-mass-spectrometry
MEXF1341 patient-derived melanoma
MEXF276 patient-derived melanoma
MEXF969 patient-derived melanoma
mRNA messenger ribonucleic acid
MTS 3-(4,5-dimethylthiazol-2-yl)-5-(3-carboxymethoxyphenyl)-2-(4-sulphophenyl)-2H-tetrazolium
NaCl Sodium chloride
NaF Sodium fluoride
NCBI National center for Biotechnology Information
NSCLC non-small cell lung cancer
NP40 Nonidet P40
PBS phosphate buffered saline
PCR polymerase chain reaction
P-gp P-glycoprotein
PMSF phenylmethylsulphonyl fluoride
PSA prostate-specific antigen
PVDF polyvinylidene fluoride
RANO response assessment for high-grade gliomas
READS restriction enzyme amplification of digested cDNAs
RECIST response evaluation criteria in solid tumours
RNA ribonucleic acid
RPMI-1640 cell culture medium used for culturing transformed and non-transformed eukaryotic cells and cell lines
RT-PCR real-time polymerase chain reaction
SAGE serial analysis of gene expression
SELDI surface-enhanced laser desorption/ionisation
SELDI-TOF surface-enhanced laser desorption/ionisation time-of-flight-mass-spectrometry
SDS sodium dodecyl sulphate
SEQ. ID No. sequence identification number
siRNA small inhibitory ribonucleic acid
SKBR3 human mammary carcinoma cell line
TMP 3,3',5,5' tetramethylbenzidine
TUNEL terminal deoxynucleotidyl transferase dUTP nick end labeling
Tween-20 Detergent, polyoxyethylene sorbitan monolaurate
TX-100 Triton-X100
YO-PRO fluorescent, monomeric cyanine, nucleic acid stain

The invention claimed is:

1. A method for predicting the response to treatment of a neoplastic disease selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes; or of an autoimmune disease selected from the group consisting of systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis, polymyositis, autoimmune hemolytic anemia, thrompocytopenic purpura, neutropenia, type I diabetes mellitus, thyroiditis (including Hashimoto's and Grave's disease), Addison's disease, polyglandular syndrome, pemphigus, (vulgois, foliaceus, subaceous and vegetaus) bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ucerose and morbus Crohn), Behcet's disease, Celic-Sprue disease, autoimmune uveitis, autoimmune myocarditis, granulomatous orchitis, aspermatogenesis without orchitis, idiopathic and secondary pulmonary fibrosis, inflammatory diseases with a possibility of autoimmune pathogensesis, such as pyoderma gangrensosum, lichen ruber, sarcoidosis, (including Lofgren and cutaneous subcutaneous type) granuloma anulare, allergic type I and type IV immunological reaction, asthma bronchiale, pollinosis, atopic, contact and airborne dermatitis, large vessel vasculitis, (Wegener's granulomatosis, Churg Strauss syndrome, microscopic polangiitis, HenochSchoenlein purpura, essential cryoglobulinemic vasculitis, cutaneous leukoklastic angiitis), (grant cell and Takayase artheritis), medium sized vessel vasculitis (polyarteritis nodosa, Kawasaki disease), small vessel vasculitis, hypersensitivity syndromes, toxic epidermal necrolysis (Stephens-Johnson syndrome, erythese multiform), diseases due to drug side effects, all forms of cutaneous, organ-specific and systemic effects due to type 1-vu (Coombs classification) immunologic forms of reaction and transplantation related pathologies, including acute and chronic graft verses host and host versus graft disease and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genitourinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e.g. stem cells); in a patient subject by administration of a compound of general formula I

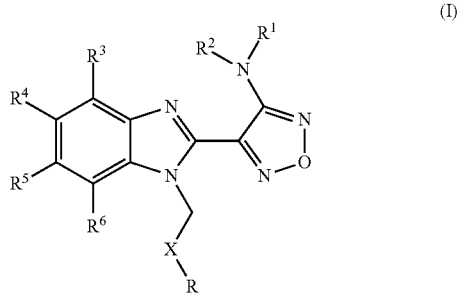

(I)

wherein
   R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy- lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y,
wherein Y is oxygen or nitrogen substituted by hydroxy or lower alkoxy;
or when R is optionally substituted phenyl or optionally substituted pyridinyl, X is additionally oxygen;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
or pharmaceutically acceptable derivatives thereof,
and wherein said prefix lower denotes a radical having up to 7 carbon atoms,
said method comprising the steps of:
a) measuring the level of the stathmin proteins or stathmin nucleic acids in a sample obtained from a patient to obtain a value or values representing this level; and
b) comparing the value or values of the levels from step a) with a standard value or a set of standard values which comparison is predictive of responsiveness to compounds of formula I.

2. The method of claim 1, wherein said patient is an animal or human being and the level of stathmin proteins or stathmin nucleic acids is measured ex vivo in the sample taken from said animal or human being.

3. The method according to claim 2, wherein the sample is derived from normal tissue, tumor tissue, circulating tumor cells, plasma, serum or whole blood.

4. The method of claim 3 wherein a higher level of stathmin proteins or stathmin nucleic acids in the sample relative to a standard value or a set of standard values predicts resistance to treating said disease with said compound of formula I-or pharmaceutical acceptable derivatives thereof.

5. The method of claim 4, wherein the determination of a higher level of stathmin proteins or stathmin nucleic acids in said sample obtained from the animal or human being is carried out by comparing the measured stathmin protein level or stathmin nucleic acid level in said sample
   i) relative to a standard value or a set of standard values of levels of stathmin proteins or stathmin nucleic acids from samples from other subjects having the same tumour histotype as said animal or human being; or
   ii) relative to a standard value or a set of standard values of levels of stathmin proteins or stathmin nucleic acids from a sample or samples of levels of stathmin from normal tissue; or
   iii) relative to a standard value or a set of standard values of levels of stathmin proteins or stathmin nucleic acids from a sample or samples obtained from the same patient before initiation of treatment with the compound of formula I or pharmaceutically acceptable derivatives thereof.

6. The method of claim 1, wherein the protein sequence of stathmin proteins is selected from the groups consisting of SEQ ID No. 1, SEQ ID 2 and homologues, mutant forms, allelic variants, isoforms, splice variants and proteins with sequences having at least 75% identity to SEQ ID 1 or SEQ ID 2.

7. method of claim 1, wherein the compound is a compound of general formula I wherein
   R represents phenyl or pyridinyl
      wherein phenyl is optionally substituted by one or two substituents independently selected from lower alkyl, lower alkoxy, amino, acetylamino, halogen and nitro; and wherein pyridinyl is optionally substituted by amino or halogen;
   X represents a group C=O;
   $R^1$ represents hydrogen or cyano-lower alkyl;
   $R^2$, $R^3$, $R^4$, $R^5$ and $R^6$ represent hydrogen;
   or pharmaceutically acceptable derivatives thereof,
   and wherein said prefix lower denotes a radical having up to and including a maximum of 7 carbon atoms.

8. The method according to claim 7, wherein said patient is an animal or human being and the level of stathmin proteins or stathmin nucleic acids is measured ex vivo in a sample taken from the animal or human being's body.

9. The method according to claim 8, wherein the sample is derived from normal tissue, tumor tissue, circulating tumor cells, plasma, serum or whole blood.

10. The method of claim 9, wherein a higher level of stathmin proteins or stathmin nucleic acids in a sample obtained from said animal or human being relative to a standard value or a set of standard values predicts resistance to a therapy with compounds of formula I or pharmaceutically acceptable derivatives thereof.

11. The method of claim 10, wherein the determination of a higher level of stathmin in said sample obtained from the animal or human being is carried out by comparing the measured stathmin protein level or stathmin nucleic acid level in said sample i) relative to a standard value or a set of standard values of levels of stathmin proteins or stathmin nucleic acids from samples from other subjects having the same tumour histotype as said animal or human being;

ii) relative to a standard value or a set of standard values of levels of stathmin proteins or stathmin nucleic acids from a sample or samples of levels of stathmin from normal tissue; or iii) relative to a standard value or a set of standard values of levels of stathmin proteins or stathmin nucleic acids from a sample or samples obtained from the same patient before initiation of treatment with the compound of formula I or pharmaceutically acceptable derivatives thereof.

12. The method of claim 1, wherein the stathmin proteins or stathmin nucleic acids are used as biomarker to select subjects suffering or predisposed to suffering from a disease for treatment with a compound of general formula I or pharmaceutically acceptable derivatives thereof.

13. The method of claim 1, wherein the stathmin proteins or stathmin nucleic acids are used as biomarker to select subjects suffering or predisposed to suffering from cancer for treatment with a compound of general formula I or pharmaceutically acceptable derivatives thereof.

14. The method of claim 7, wherein the stathmin proteins or stathmin nucleic acids are used as biomarker to select subjects suffering or predisposed to suffering from a disease for treatment with a compound of general formula I or pharmaceutically acceptable derivatives thereof.

15. The method of claim 14, wherein the stathmin proteins or stathmin nucleic acids are used as biomarker to select subjects suffering or predisposed to suffering from cancer for treatment with a compound of general formula I or pharmaceutically acceptable derivatives thereof.

16. The method of claim 1, wherein the compound is represented by the following formula wherein R Y and Ri are defined as follows:

| R | Y | R¹ |
|---|---|---|
| 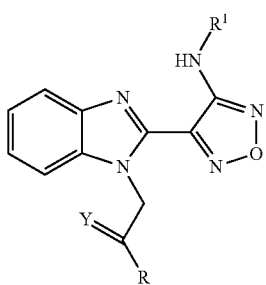 | O | CH₂CH₂CN |

-continued

| R | Y | R¹ |
|---|---|---|
| H₂N–⟨phenyl⟩– | O | H |
| H₂N–⟨pyridyl⟩– | O | CH₂CH₂CN | or pharmaceutically acceptable derivatives thereof.

17. The method of claim 1, wherein the compound is

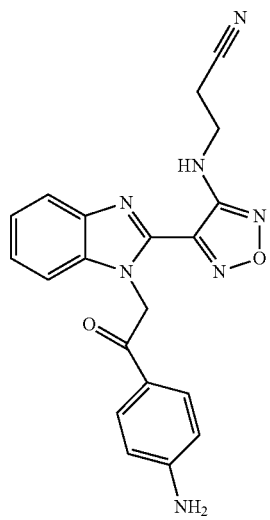 [SMILES: N#CCCNc1nonc1-c1nc2ccccc2n1CC(=O)c1ccc(N)cc1]

or pharmaceutically acceptable derivatives thereof.

18. The method of claim 1, wherein a pharmaceutically acceptable derivative is selected from the group consisting of a salt, solvate, pro-drug, salt of a pro-drug, polymorph and isomer of the compound of general formula I.

19. The method of claim 18, wherein the pharmaceutically acceptable pro-drug is an amide formed from an amino group present within the R group of the compound of formula I as defined in claim 1 and the carboxy group of glycine, alanine or lysine.

20. The method of claim 7 wherein a pharmaceutically acceptable derivative is selected from the group consisting of a salt, solvate, pro-drug, salt of a pro-drug, polymorph and isomer of the compound of general formula I as defined in claim 17.

21. The method of claim 20, wherein the pharmaceutically acceptable pro-drug is an amide formed from an amino group present within the R group of the compound of formula I as defined in claim 1 and the carboxy group of glycine, alanine or lysine.

22. The method of claim 1, wherein the compound is

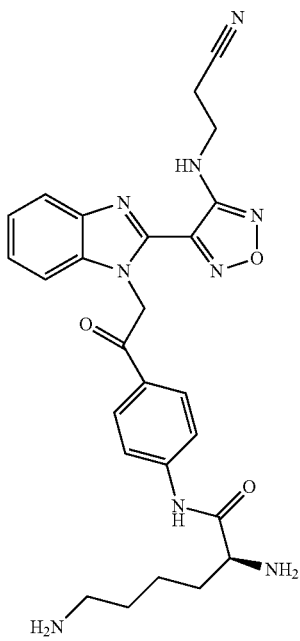 [SMILES: N#CCCNc1nonc1-c1nc2ccccc2n1CC(=O)c1ccc(NC(=O)[C@@H](N)CCCCN)cc1]

or a pharmaceutically acceptable salt thereof.

23. The method of claim 1, wherein the neoplastic disease is a cancer selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, myeloma and sarcomas.

24. The method of claim 23, wherein the neoplastic_disease is selected from the group consisting of gastric cancer, lung cancer and melanoma.

25. A method of treating a neoplastic disease selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes, in a patient in need thereof, said method comprising
  a) obtaining a sample of biologic material from the body of said patient;
  b) determining the level of the stathmin proteins or stathimn nucleic acids in said sample; and
  c) then treating the patient with a compound of formula T as described above or a pharmaceutically acceptable derivative thereof, if the level of stathmin proteins or stathmin nucleic acids in said sample is not higher than a standard value or set of standard values for the level of stathmin proteins-or stathmin nucleic acids.

26. The method of claim 25, wherein the standard values of stathmin protein or stathmin nucleic acids are determined,
  1) from samples of other subjects having the same tumour histotype as said animal or human being;
  ii) from a sample or samples of normal tissue; or
  iii) from a sample or samples obtained from the same patient before initiation treatment with the compound of formula I or pharmaceutically acceptable derivatives thereof.

27. A method of treating an autoimmune disease, wherein said autoimmune disease is systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis/polymyositis, autoimmune hemolytic anemia, thrombocytopenic purpura, neutropenia, type I diabetes mellitus, thyroiditis (including Hashimoto's and Grave's disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogensesis, such as pyoderma gangrensosum, lichen ruber, sarcoidosis (including Lofgren and cutaneous/subcutaneous type), granuloma anulare, allergic type I and type IV immunological reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, HenochSchoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type 1-vu (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oro-pharynx, esophageus, stomach, small intestine, colon, and rectum, including parts of above mentioned organs down to single cell level and substructures, e. g. stem cells).

28. The method of claim 1, wherein the autoimmune disease is thyroiditis selected from the group consisting of Hashimoto's disease and Grave's disease.

29. The method of claim 1, wherein the autoimmune disease is pemphigus selected from the group consisting of pemphigus vulgaris, pemphigus foliaceus, pemphigus sebaceous and pemphigus vegetans.

30. The method of claim 1, wherein the autoimmune disease is inflammatory bowel disease selected from the group consisting of colitis ulcerosa and morbus Crohn.

31. The method of claim 1, wherein the autoimmune disease is sarcoidosis selected from the group consisting of Lofgren sarcoidosis, cutaneous sarcoidosis and subcutaneous sarcoidosis.

32. The method of claim 1, wherein the autoimmune disease is large vessel vasculitis selected from the group consisting of giant cell vasculitis and Takayasu's arteritis.

33. The method of claim 1, wherein the autoimmune disease is medium sized vessel vasculitis selected from the group consisting of polyarteritis nodosa, and Kawasaki disease.

34. The method of claim 1, wherein the autoimmune disease is small vessel vasculitis selected from the group consisting of Wegener's granulomatosis, Churg Strauss syndrome, microscopic polangiitis, HenochSchoenlein purpura, essential cryoglobulinemic vasculitis and cutaneous leukoklastic angiitis.

35. The method of claim 1, wherein the autoimmune disease is toxic epidermal necrolysis selected from the group consisting of Stevens-Johnson syndrome and erythema multiforme.

36. The method of claim 1, wherein the autoimmune disease is transplantation related pathologies selected from the group consisting of acute and chronic graft versus host and host versus graft disease.

37. The method of claim 1, wherein step a) comprises measuring the level of the stathmin proteins.

38. The method of claim 1, wherein the nucleic acid sequence representing stathmin nucleic acids is selected from the group consisting of SEQ ID No. 3, SEQ ID No. 4, SEQ ID No. 5, and SEQ ID No. 6 and sequences having at least about 75% identity to SEQ ID No. 3, SEQ ID No. 4, SEQ ID No. 5, and SEQ ID No. 6.

39. A kit for predicting the response to a compound of general formula I or a pharmaceutically acceptable derivative thereof, as defined in claim 1 comprising reagents necessary for measuring the level of stathmin proteins or stathmin nucleic acids in a sample of further comprising a comparator module which comprises a standard value or set of standard valuse to which the level of stathmin proteins or stathmin nucleic acids in the sample is compared.

40. The kit according to claim 39, wherein the reagents comprise:
  a) a capture reagent comprising a detector for stathmin proteins and
  b) a detection reagent.

41. The kit according to claim 40, wherein said capture reagent is an antibody.

42. The kit according to claim 39, wherein the kit comprises a compound of the following formula or a pharmaceutically acceptable salt thereof,

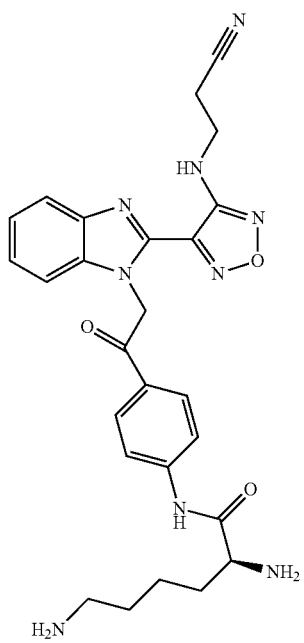 [SMILES: N#CCCNc1nonc1-c1nc2ccccc2n1CC(=O)c1ccc(NC(=O)[C@@H](N)CCCCN)cc1]

43. The kit of claim 42 wherein said salt is a hydrochloride salt.

44. The kit of claim 41 comprising reagents necessary for measuring the level of stathmin proteins in a sample and further comprising a comparator module which comprises a standard value or set of standard values to which the level of stathmin proteins in the sample is compared.

45. The kit according to claim 44, wherein the reagents comprise a labelled probe or primers for hybridisation to stathmin nucleic acid in the sample.

46. The method according to claim 2, wherein the sample is derived from serum.

47. The method of claim 25 wherein the neoplastic disease is selected from the group consisting of breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis.

48. The method of claim 1 wherein the neoplastic disease is a cancer selected from the group consisting of breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis.

49. The method of claim 23, wherein the neoplastic disease is a cancer selected from the group consisting of breast cancer, cervical cancer, gastric cancer, lung cancer and melanoma.

50. The method of claim 49, wherein the neoplastic disease is a cancer selected from the group consisting of gastric cancer, lung cancer and melanoma.

51. The method of treating a neoplastic disease of claim 25, wherein the neoplastic disease is a cancer selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

52. The method of claim 51, wherein the neoplastic disease is a cancer selected from the group consisting of breast cancer, cervical cancer, gastric cancer, lung cancer and melanoma.

53. The method of claim 52, wherein the neoplastic disease is a cancer selected from the group consisting of gastric cancer, lung cancer and melanoma.

54. The method of claim 1, wherein the disease is a neoplastic disease.

55. The method of claim 25, wherein the disease is a neoplastic disease.

56. The method according to claim 1 wherein the compound is

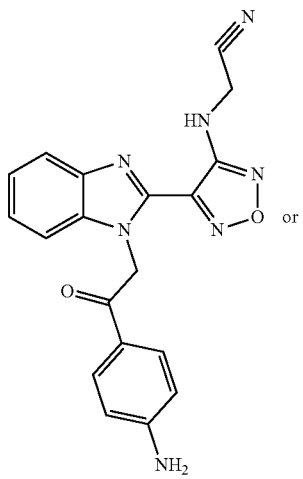 or

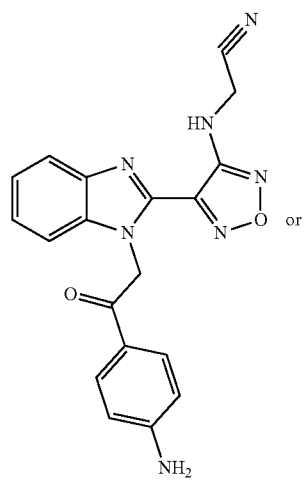 or

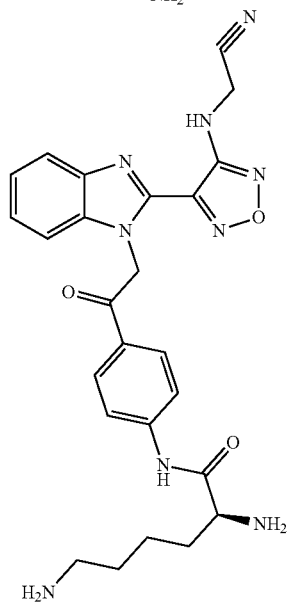

or a pharmaceutically acceptable salt thereof, and the disease is ovarian cancer.

58. The method according to claim 1 wherein the compound is

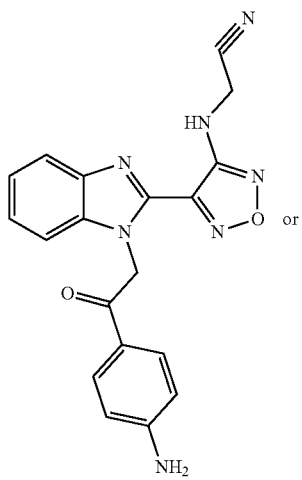 or or a pharmaceutically acceptable salt thereof, and the disease is breast cancer.

57. The method according to claim 1 wherein the compound is

-continued
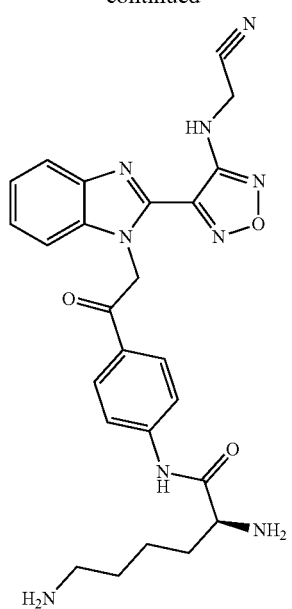
or a pharmaceutically acceptable salt thereof, and the disease is colorectal cancer.
59. The method according to claim 1 wherein the compound is
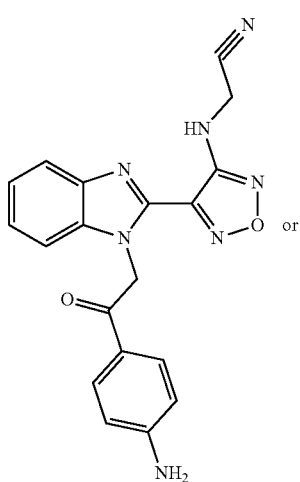
-continued
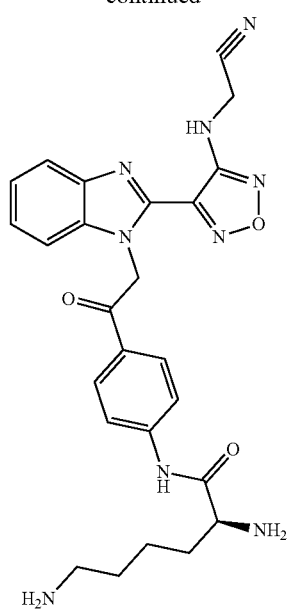
or a pharmaceutically acceptable salt thereof, and the disease is lung cancer.
60. The method according to claim 1 wherein the compound is
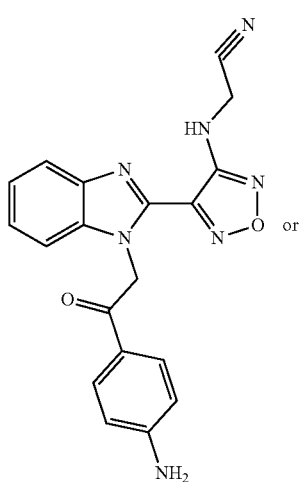
or -continued
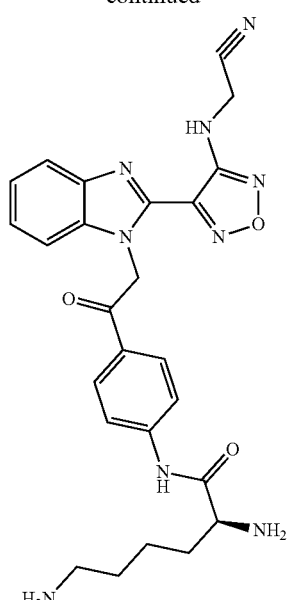
or a pharmaceutically acceptable salt thereof, and the disease is liver cancer.
61. The method according to claim 1 wherein the compound is
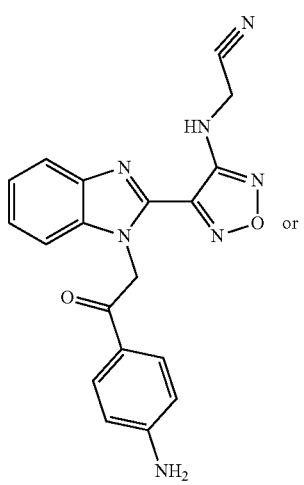
or
-continued
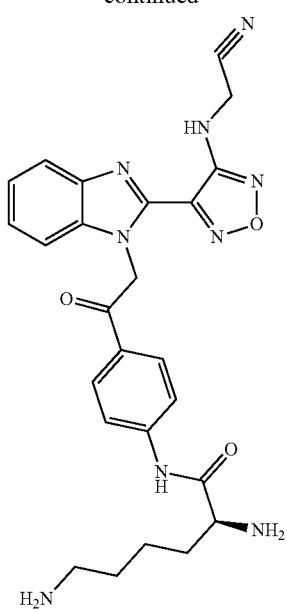
or a pharmaceutically acceptable salt thereof, and the disease is gastric cancer.
62. The method according to claim 1 wherein the compound is
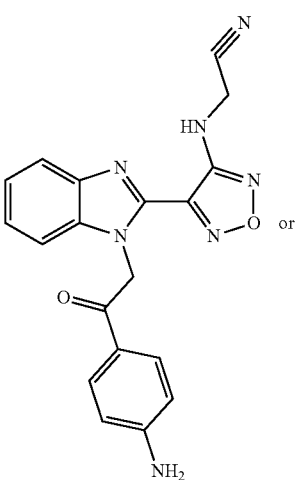
or 73
-continued
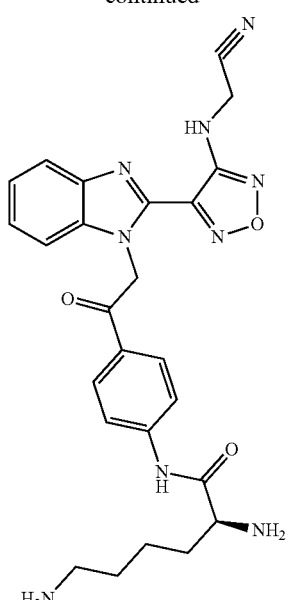
or a pharmaceutically acceptable salt thereof, and the disease is pancreatic cancer.
63. The method according to claim 1 wherein the compound is
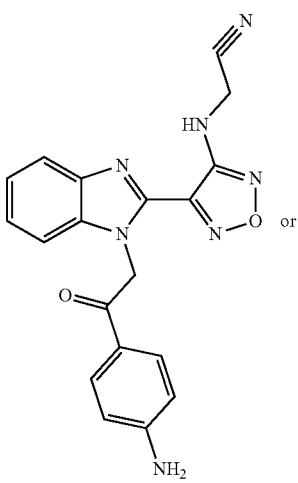 or
74
-continued
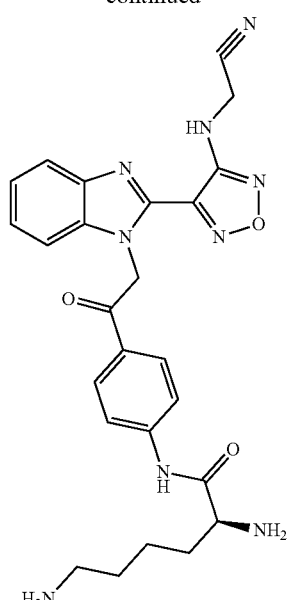
or a pharmaceutically acceptable salt thereof, and the disease is a hematological malignancy.
64. The method according to claim 1 wherein the compound is
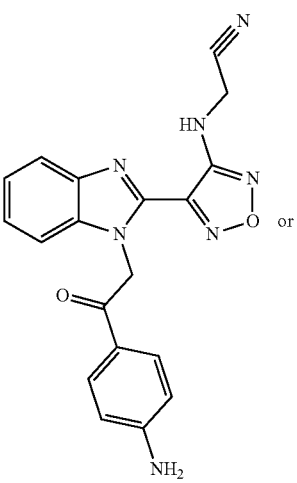 or 75
-continued
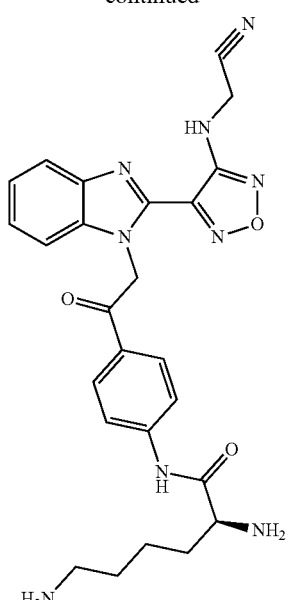
or a pharmaceutically acceptable salt thereof, and the disease is kidney cancer.
65. The method according to claim 1 wherein the compound is
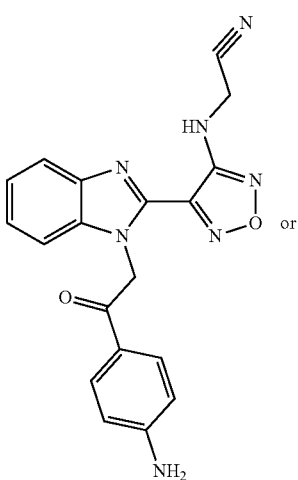
or
76
-continued
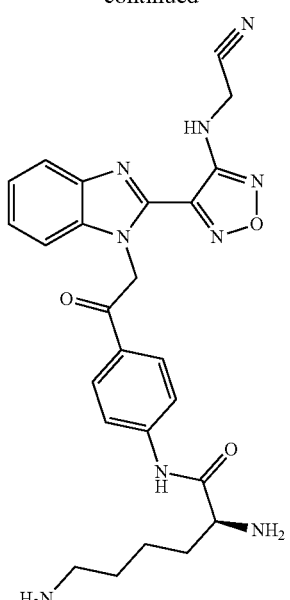
or a pharmaceutically acceptable salt thereof, and the disease is skin cancer.
66. The method according to claim 1 wherein the compound is
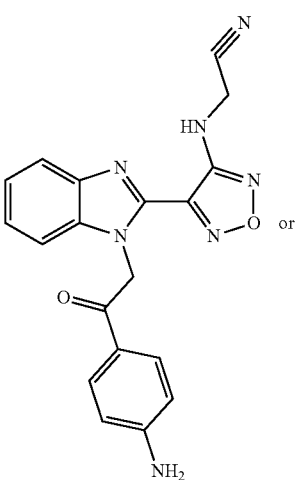
or 77
-continued
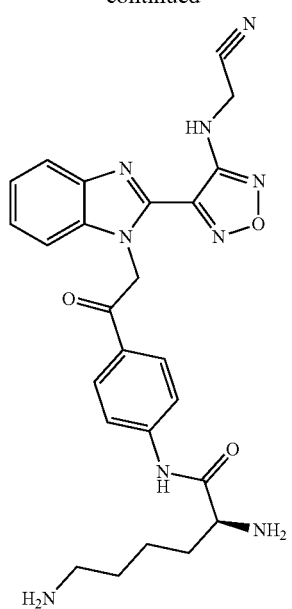
or a pharmaceutically acceptable salt thereof, and the disease is brain cancer.
67. The method according to claim 1 wherein the compound is
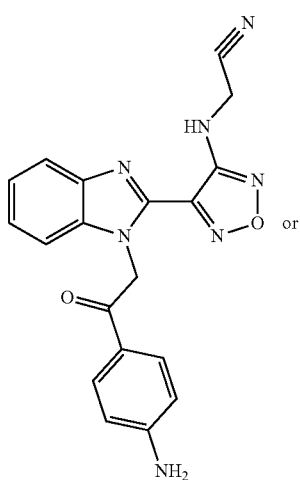
78
-continued
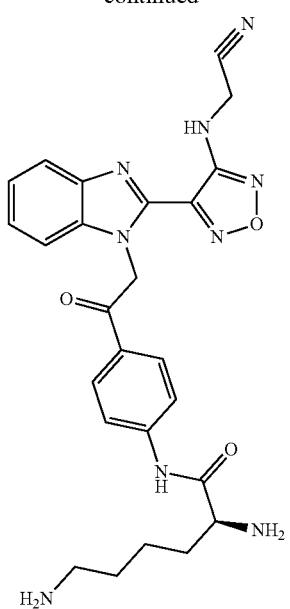
or a pharmaceutically acceptable salt thereof, and the disease is prostate cancer.
68. The method according to claim 1 wherein the compound is
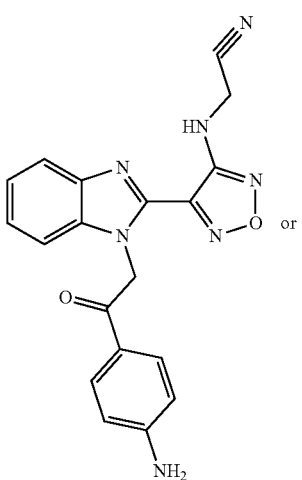
or
or

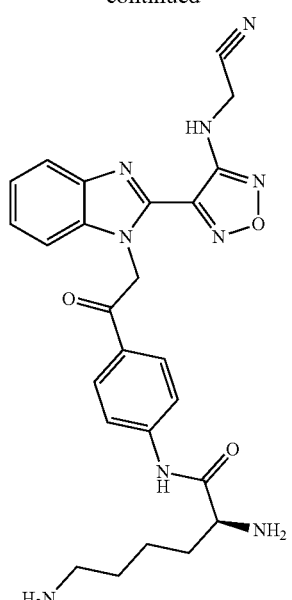
or a pharmaceutically acceptable salt thereof, and the disease is small cell lung cancer.
69. The method according to claim 1 wherein the compound is
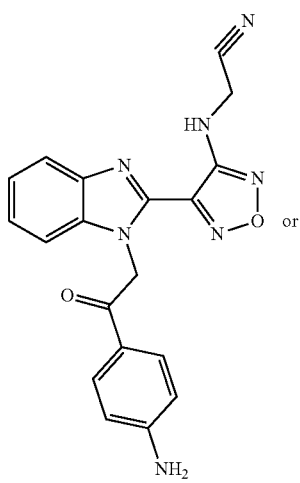
or
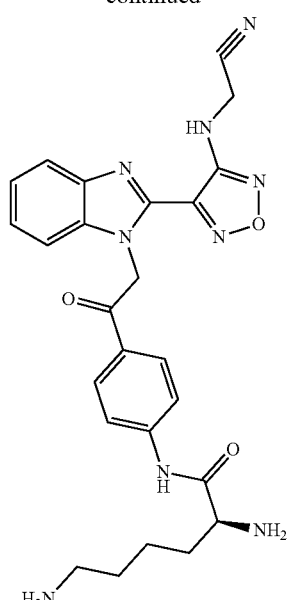
or a pharmaceutically acceptable salt thereof, and the disease is non-small cell lung cancer.
70. The method according to claim 1 wherein the compound is
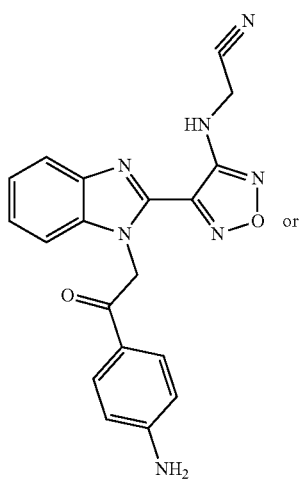
or

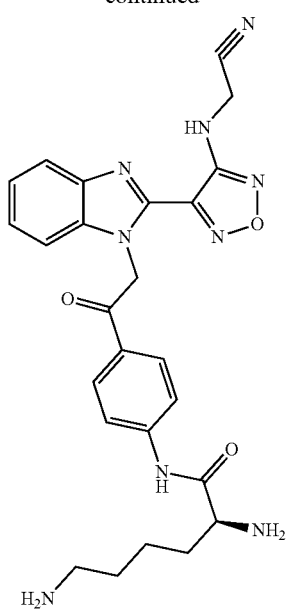
or a pharmaceutically acceptable salt thereof, and the disease is large cell lung cancer.
71. The method according to claim 1 wherein the compound is
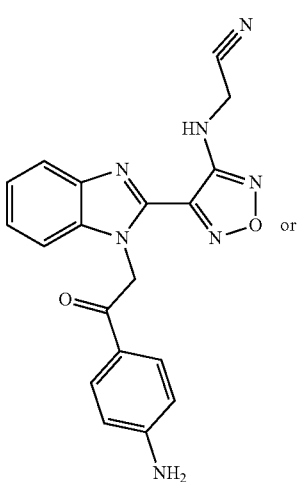
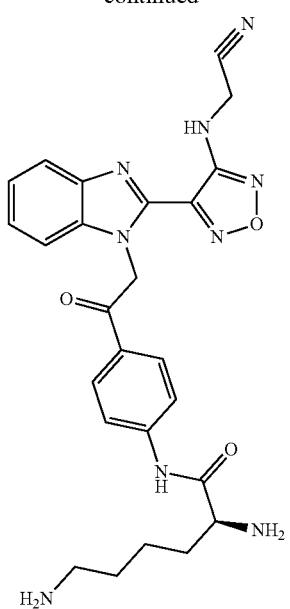
or a pharmaceutically acceptable salt thereof, and the disease is mesothelioma.
72. The method according to claim 1 wherein the compound is
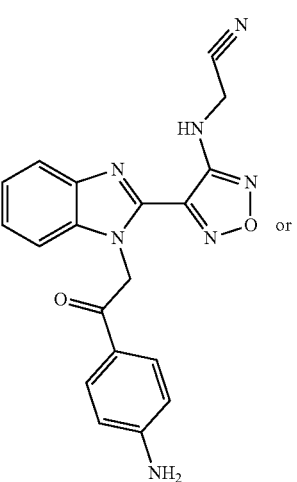

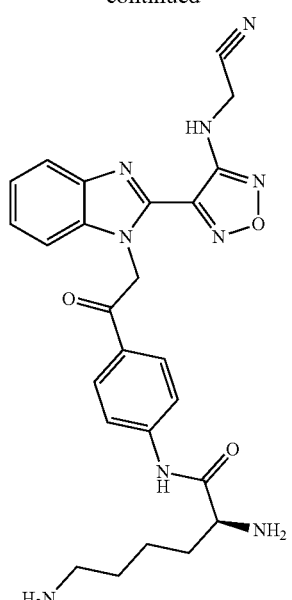
or a pharmaceutically acceptable salt thereof, and the disease is lymphoma.
73. The method according to claim 1 wherein the compound is
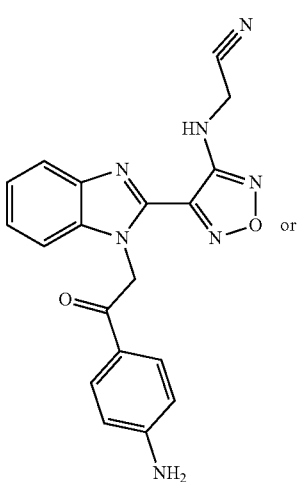
or
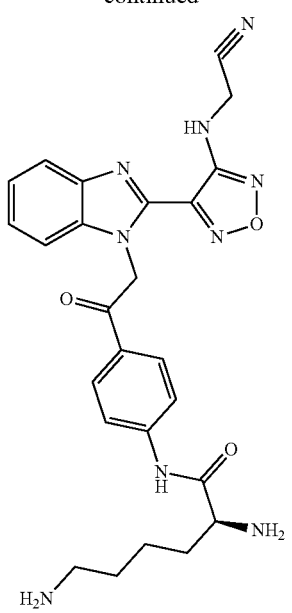
or a pharmaceutically acceptable salt thereof, and the disease is leukemia.
74. The method according to claim 1 wherein the compound is
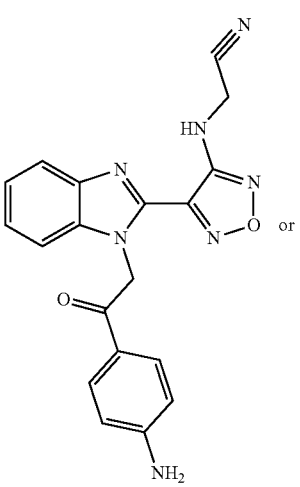
or

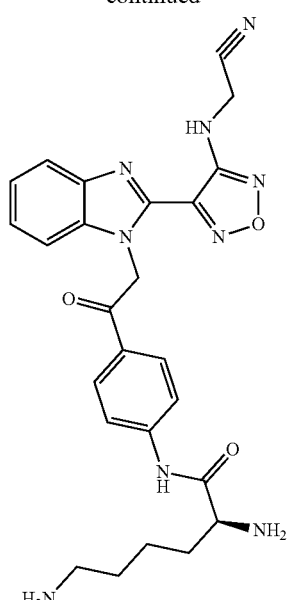
or a pharmaceutically acceptable salt thereof, and the disease is myeloma.
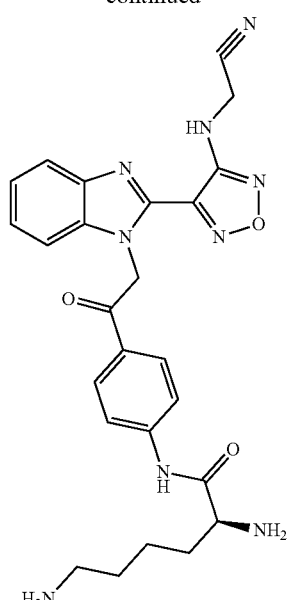
or a pharmaceutically acceptable salt thereof, and the disease is a head and neck cancer.
75. The method according to claim 1 wherein the compound is
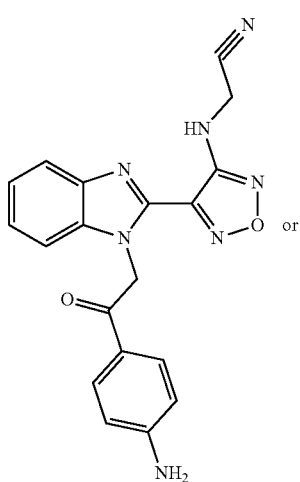
or
76. The method according to claim 1 wherein the compound is
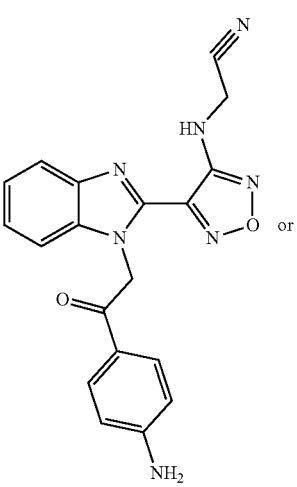
or -continued
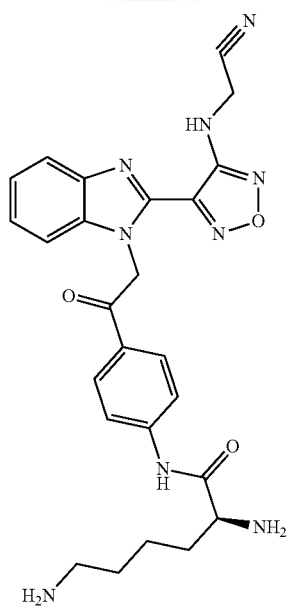
or a pharmaceutically acceptable salt thereof, and the disease is a glioma.
77. The method according to claim 25 wherein the compound is
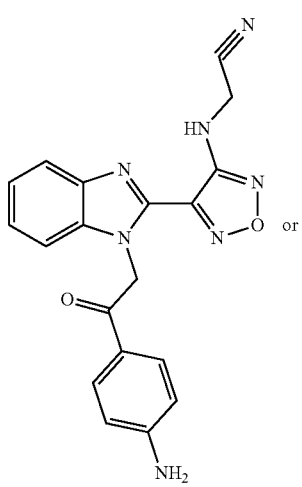
or
-continued
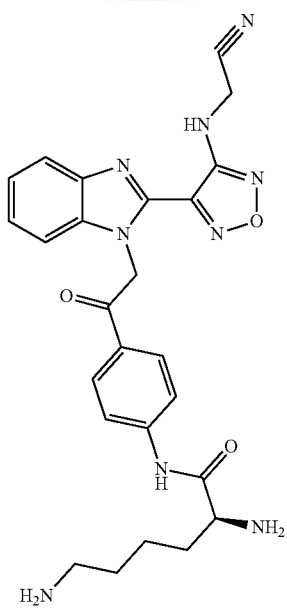
or a pharmaceutically acceptable salt thereof, and the disease is breast cancer.
78. The method according to claim 25 wherein the compound is
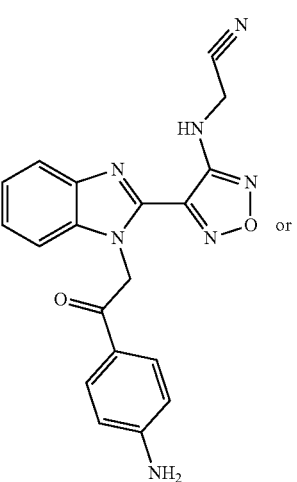
or

89
-continued
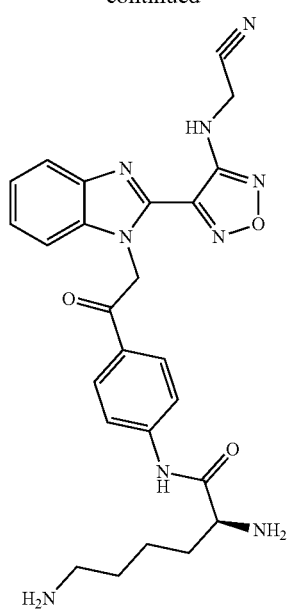
or a pharmaceutically acceptable salt thereof, and the disease is ovarian cancer.
79. The method according to claim 25 wherein the compound is
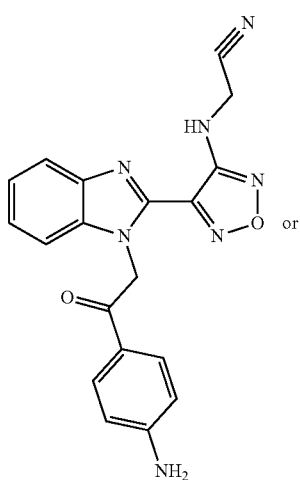
or
90
-continued
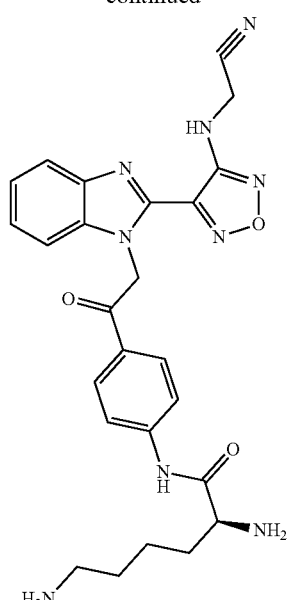
or a pharmaceutically acceptable salt thereof, and the disease is colorectal cancer.
80. The method according to claim 25 wherein the compound is
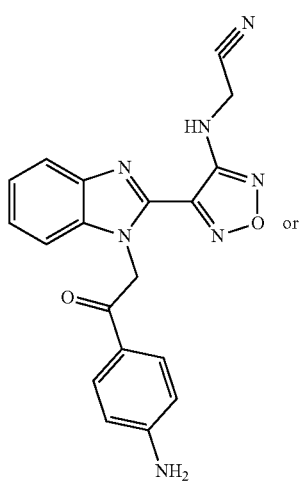
or

91
-continued
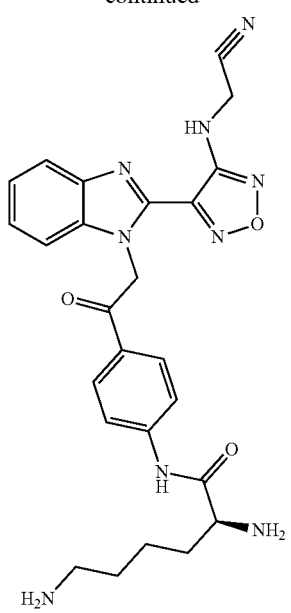
or a pharmaceutically acceptable salt thereof, and the disease is lung cancer.
81. The method according to claim 25 wherein the compound is
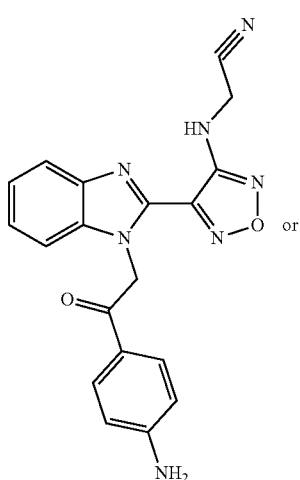
or
92
-continued
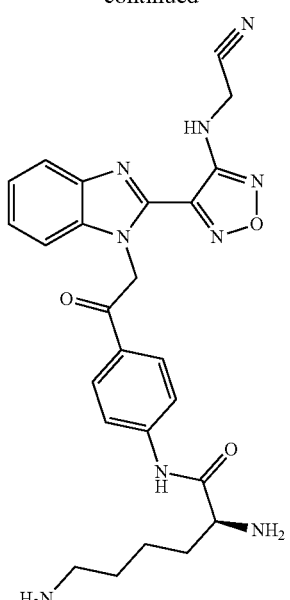
or a pharmaceutically acceptable salt thereof, and the disease is liver cancer.
82. The method according to claim 25 wherein the compound is
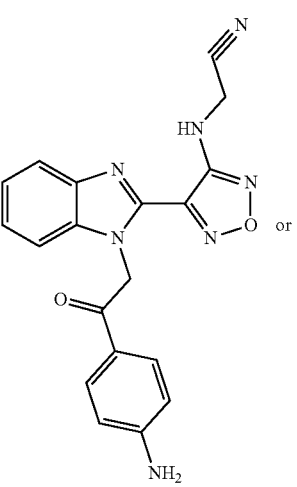
or 93
-continued
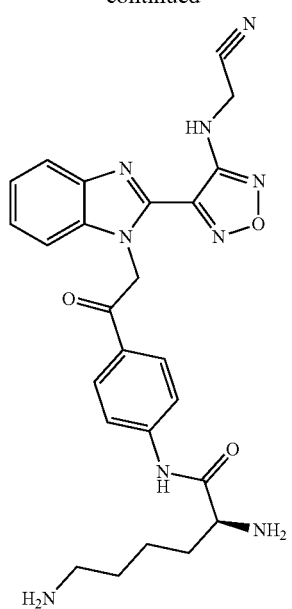
or a pharmaceutically acceptable salt thereof, and the disease is gastric cancer.
83. The method according to claim 25 wherein the compound is
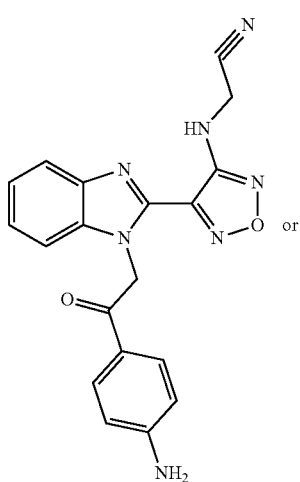
or
94
-continued
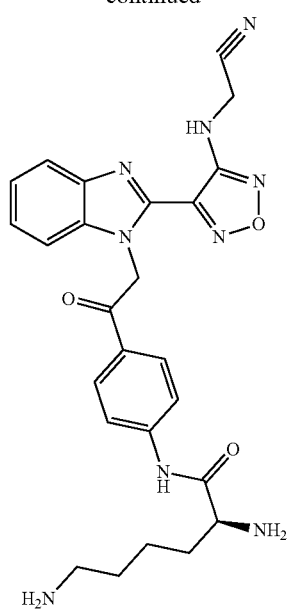
or a pharmaceutically acceptable salt thereof, and the disease is pancreatic cancer.
84. The method according to claim 25 wherein the compound is
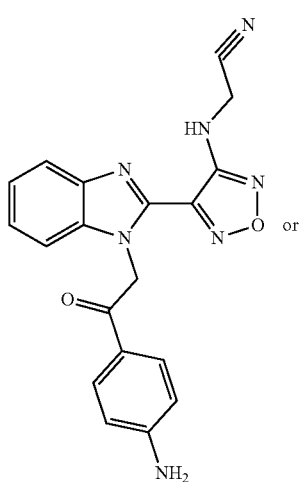
or

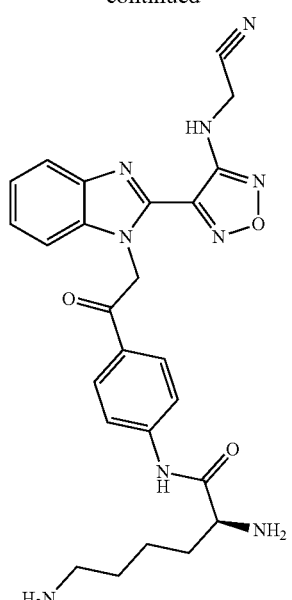
or a pharmaceutically acceptable salt thereof, and the disease is a hematological malignancy.
85. The method according to claim 25 wherein the compound is
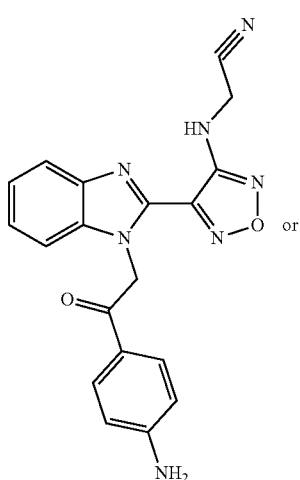 or
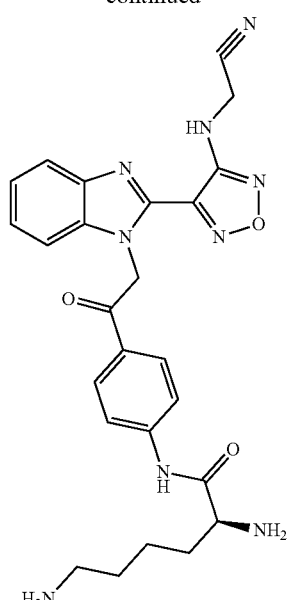
or a pharmaceutically acceptable salt thereof, and the disease is kidney cancer.
86. The method according to claim 25 wherein the compound is
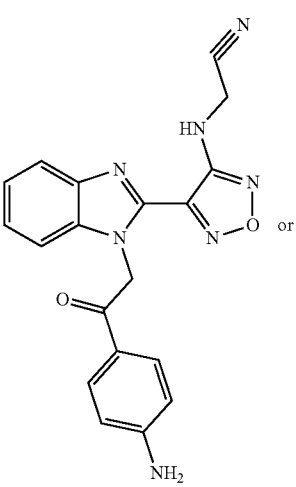 or

97
-continued
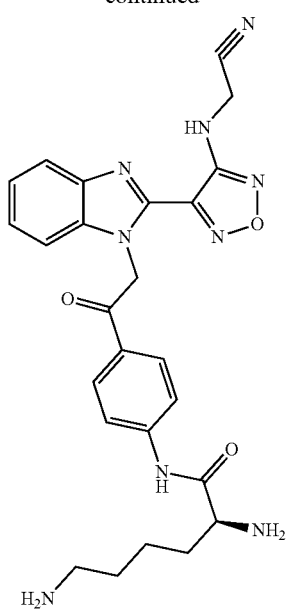
or a pharmaceutically acceptable salt thereof, and the disease is skin cancer.
87. The method according to claim 25 wherein the compound is
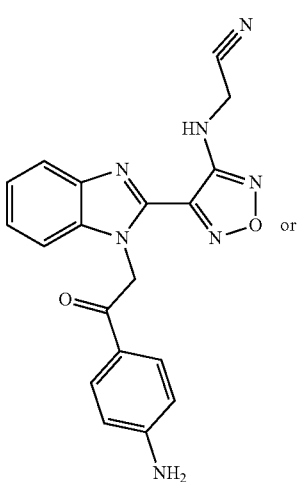
or
98
-continued
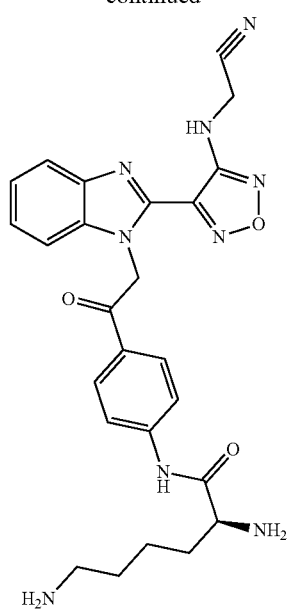
or a pharmaceutically acceptable salt thereof, and the disease is brain cancer.
88. The method according to claim 25 wherein the compound is
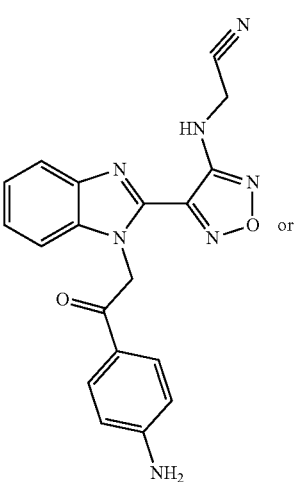
or

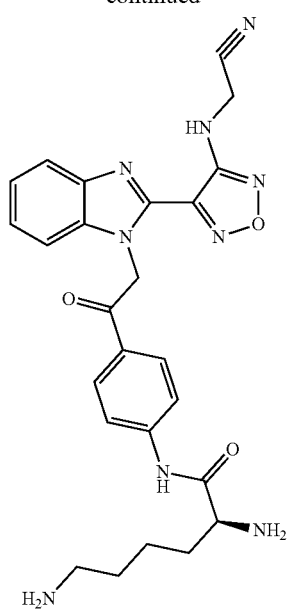
or a pharmaceutically acceptable salt thereof, and the disease is prostate cancer.
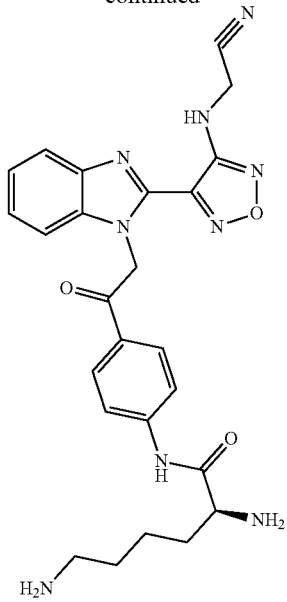
or a pharmaceutically acceptable salt thereof, and the disease is small cell lung cancer.
89. The method according to claim 25 wherein the compound is
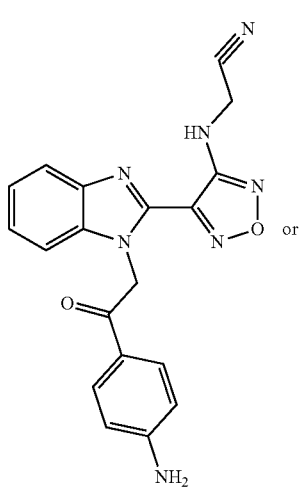
or
90. The method according to claim 25 wherein the compound is
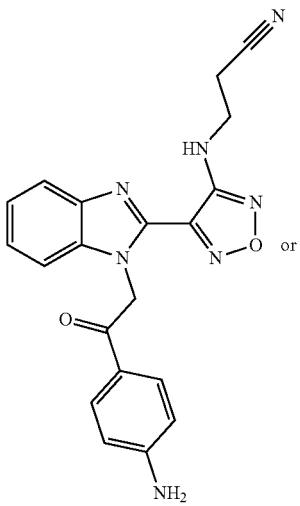
or

101
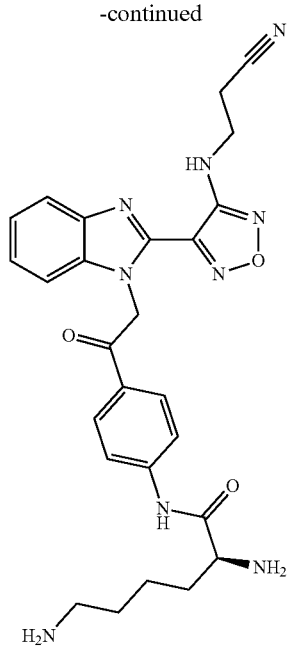
or a pharmaceutically acceptable salt thereof, and the disease is non-small cell lung cancer.
91. The method according to claim 25 wherein the compound is
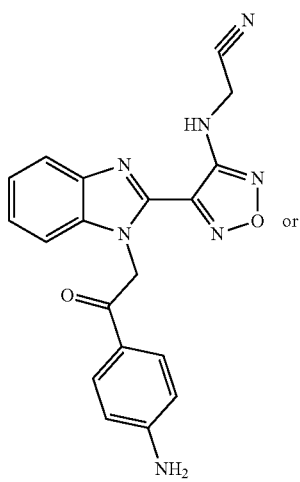
or
102
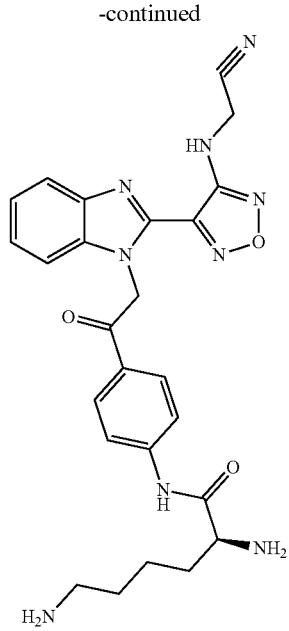
or a pharmaceutically acceptable salt thereof, and the disease is large cell lung cancer.
92. The method according to claim 25 wherein the compound is
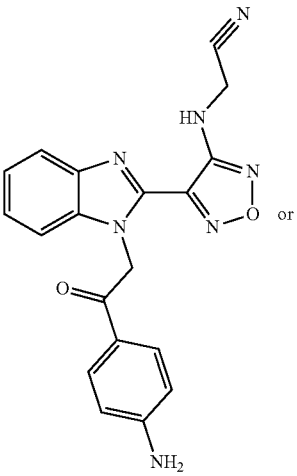
or 103
-continued
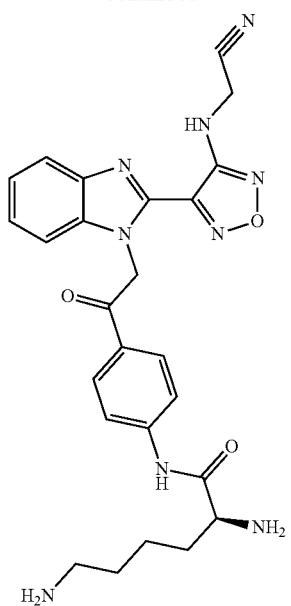
or a pharmaceutically acceptable salt thereof, and the disease is mesothelioma.
93. The method according to claim 25 wherein the compound is
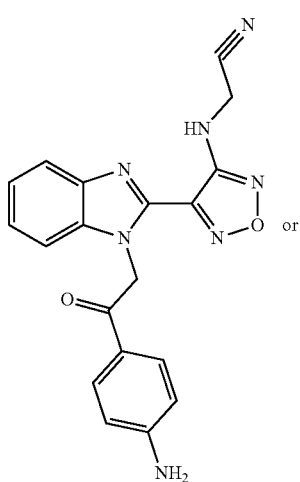
or
104
-continued
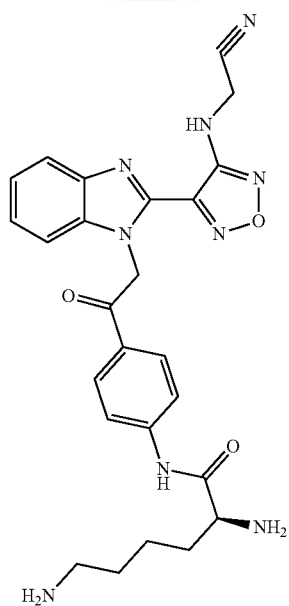
or a pharmaceutically acceptable salt thereof, and the disease is lymphoma.
94. The method according to claim 25 wherein the compound is
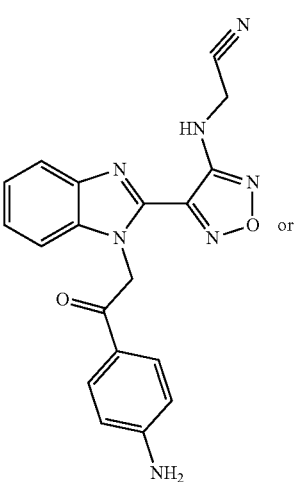
or 105
-continued
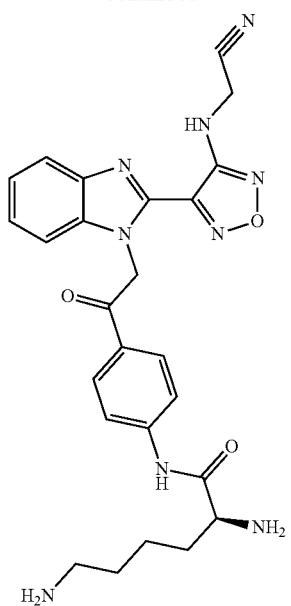
or a pharmaceutically acceptable salt thereof, and the disease is leukemia.
95. The method according to claim 25 wherein the compound is
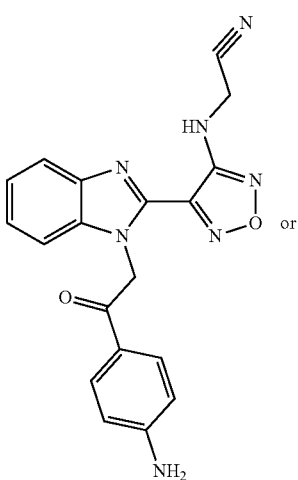
or
106
-continued
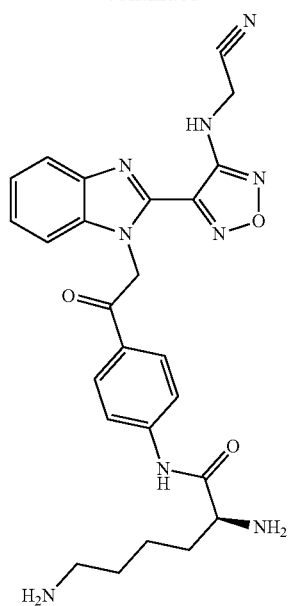
or a pharmaceutically acceptable salt thereof, and the disease is myeloma.
96. The method according to claim 25 wherein the compound is
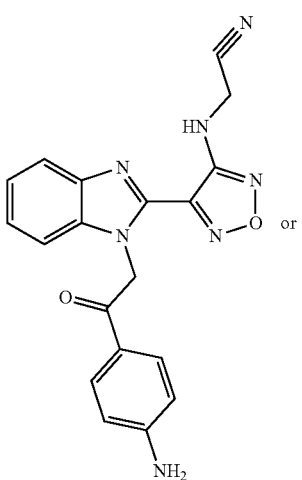
or -continued
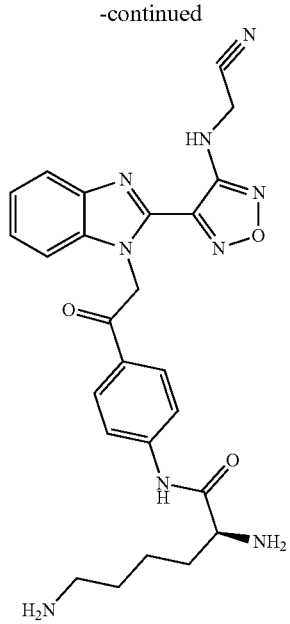
or a pharmaceutically acceptable salt thereof, and the disease is a head and neck cancer.
97. The method according to claim 25 wherein the compound is
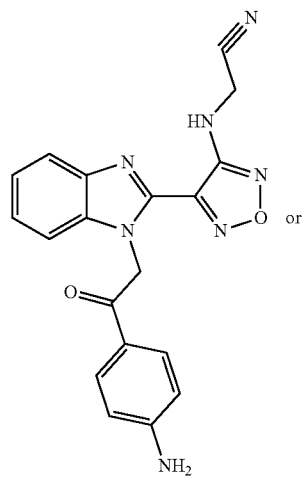 or
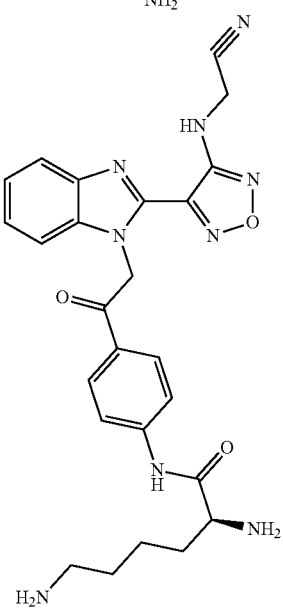
or a pharmaceutically acceptable salt thereof, and the disease is a glioma.
* * * * *

SEQUENCE LISTING

<160> NUMBER OF SEQ ID NOS: 6

<210> SEQ ID NO 1
<211> LENGTH: 149
<212> TYPE: PRT
<213> ORGANISM: Homo sapiens

<400> SEQUENCE: 1

Met Ala Ser Ser Asp Ile Gln Val Lys Glu Leu Glu Lys Arg Ala Ser
1               5                   10                  15

Gly Gln Ala Phe Glu Leu Ile Leu Ser Pro Arg Ser Lys Glu Ser Val
            20                  25                  30

Pro Glu Phe Pro Leu Ser Pro Pro Lys Lys Lys Asp Leu Ser Leu Glu
        35                  40                  45

Glu Ile Gln Lys Lys Leu Glu Ala Ala Glu Glu Arg Arg Lys Ser His
    50                  55                  60

Glu Ala Glu Val Leu Lys Gln Leu Ala Glu Lys Arg Glu His Glu Lys
65                  70                  75                  80

Glu Val Leu Gln Lys Ala Ile Glu Glu Asn Asn Asn Phe Ser Lys Met
                85                  90                  95

Ala Glu Glu Lys Leu Thr His Lys Met Glu Ala Asn Lys Glu Asn Arg
            100                 105                 110

Glu Ala Gln Met Ala Ala Lys Leu Glu Arg Leu Arg Glu Lys Asp Lys
        115                 120                 125

His Ile Glu Glu Val Arg Lys Asn Lys Glu Ser Lys Asp Pro Ala Asp
    130                 135                 140

Glu Thr Glu Ala Asp
145

<210> SEQ ID NO 2
<211> LENGTH: 174
<212> TYPE: PRT
<213> ORGANISM: Homo sapiens

<400> SEQUENCE: 2

Met Ala Ser Ser Asp Ile Gln Val Lys Glu Leu Glu Lys Arg Ala Ser
1               5                   10                  15

Gly Gln Ala Phe Glu Leu Ile Leu Ser Pro Arg Ser Lys Glu Ser Val
            20                  25                  30

Pro Glu Phe Pro Leu Ser Pro Pro Lys Lys Lys Asp Leu Ser Leu Glu
        35                  40                  45

Glu Ile Gln Lys Lys Leu Glu Ala Ala Glu Glu Arg Arg Lys Ser His
    50                  55                  60

Glu Ala Glu Val Leu Lys Gln Leu Ala Glu Lys Arg Glu His Glu Lys
65                  70                  75                  80

Glu Val Leu Gln Lys Ala Ile Glu Glu Asn Asn Asn Phe Ser Lys Met
                85                  90                  95

Ala Glu Glu Lys Leu Thr His Lys Met Glu Ala Asn Lys Glu Asn Arg
            100                 105                 110

Glu Ala Gln Met Ala Ala Lys Leu Glu Arg Leu Arg Glu Lys Met Tyr
        115                 120                 125

Phe Trp Thr His Gly Pro Gly Ala His Pro Ala Gln Ile Ser Ala Glu
    130                 135                 140

```
Gln Ser Cys Leu His Ser Val Pro Ala Leu Cys Pro Ala Leu Gly Leu
145                 150                 155                 160

Gln Ser Ala Leu Ile Thr Trp Ser Asp Leu Ser His His His
                165                 170

<210> SEQ ID NO 3
<211> LENGTH: 1542
<212> TYPE: DNA
<213> ORGANISM: Homo sapiens

<400> SEQUENCE: 3
gctctcggcc aatgcggagc cccgcgcgga ggtcacgtgc ctctgtttgg cgcttttgtg      60
cgcgcccggg tctgttggtg ctcagagtgt ggtcaggcgg ctcggactga gcaggacttt     120
ccttatccca gttgattgtg cagaatacac tgcctgtcgc ttgtcttcta ttccaccatgg    180 cttcttctga tatccaggtg aaagaactgg agaagcgtgc ctcaggccag gcttttgagc    240
tgattctcag ccctcggtca aaagaatctg ttccagaatt ccccctttcc cctccaaaga    300
agaaggatct ttccctggag gaaattcaga agaaattaga agctgcagaa gaaagacgca    360
agtcccatga agctgaggtc ttgaagcagc tggctgagaa acgagagcac gagaaagaag    420
tgcttcagaa ggcaatagaa gagaacaaca acttcagtaa aatggcagaa gagaaactga    480
cccacaaaat ggaagctaat aaagagaacc gagaggcaca aatggctgcc aaactggaac    540
gtttgcgaga aaggataag cacattgaag aagtgcggaa gaacaaagaa tccaaagacc    600
ctgctgacga gactgaagct gactaatttg ttctgagaac tgactttctc cccatcccct    660
tcctaaatat ccaaagactg tactggccag tgtcattta tttttttccct cctgacaaat    720 attttagaag ctaatgtagg actgtatagg tagatccaga tccagactgt aagatgttgt    780 tttagggct aaaggggaga aactgaaagt gttttactct ttttctaaag tgttggtctt    840
tctaatgtag ctatttttct tgttgcatct tttctacttc agtacacttg gtgtactggg    900
ttaatggcta gtactgtatt ggctctgtga aaacatattt gtgaaaagag tatgtagtgg    960
cttcttttga actgttagat gctgaatatc tgttcacttt tcaatcccaa ttctgtccca   1020
atcttaccag atgctactgg acttgaatgg ttaataaaac tgcacagtgc tgttggtggc   1080
agtgacttct tttgagttag gttaataaat caagccatag agcccctcct ggttgatact   1140
tgttccagat ggggcctttg gggctggtag aaatacccaa cgcacaaatg accgcacgtt   1200
ctctgccccg tttcttgccc cagtgtggtt tgcattgtct ccttccacaa tgactgcttt   1260
gtttggatgc ctcagcccag gtcagctgtt actttctttc agatgtttat ttgcaaacaa   1320 ccatttttg ttctgtgtcc cttttaaaag gcagattaaa agcacaagcg tgtttctaga   1380
gaacagttga gagagaatct caagattcta cttggtggtt tgcttgctct acgttacagg   1440
tggggcatgt cctcatcctt tcctgccata aaagctatga cacgagaatc agaatattaa   1500
taaaacttta tgtactgctg tagcaaaaaa aaaaaaaaaa aa                       1542

<210> SEQ ID NO 4
<211> LENGTH: 1518
<212> TYPE: DNA
<213> ORGANISM: Homo sapiens

<400> SEQUENCE: 4
aggggcactg ctctgtccga gtgctgccct tggggcgagg cgggcatgtg gctctacaag      60
gtggagtcca ggcggccaaa gtttggaaag gactttcctt atcccagttg attgtgcaga    120
atacactgcc tgtcgcttgt cttctattca ccatggcttc ttctgatatc caggtgaaag    180
```

```
aactggagaa gcgtgcctca ggccaggctt ttgagctgat tctcagccct cggtcaaaag      240
aatctgttcc agaattcccc ctttcccctc caaagaagaa ggatctttcc ctggaggaaa      300
ttcagaagaa attagaagct gcagaagaaa gacgcaagtc ccatgaagct gaggtcttga      360
agcagctggc tgagaaacga gagcacgaga agaagtgct tcagaaggca atagaagaga      420
acaacaactt cagtaaaatg gcagaagaga aactgaccca caaaatggaa gctaataaag      480
agaaccgaga ggcacaaatg gctgccaaac tggaacgttt gcgagagaag gataagcaca      540
ttgaagaagt gcggaagaac aaagaatcca agaccctgc tgacgagact gaagctgact      600
aatttgttct gagaactgac tttctcccca tccccttcct aaatatccaa agactgtact      660
ggccagtgtc atttattttt ttccctcctg acaaatattt tagaagctaa tgtaggactg      720
tataggtaga tccagatcca gactgtaaga tgttgtttta ggggctaaag gggagaaact      780
gaaagtgttt tactcttttt ctaaagtgtt ggtctttcta atgtagctat ttttcttgtt      840
gcatcttttc tacttcagta cacttggtgt actgggttaa tggctagtac tgtattggct      900
ctgtgaaaac atatttgtga aaagagtatg tagtggcttc ttttgaactg ttagatgctg      960
aatatctgtt cacttttcaa tcccaattct gtcccaatct taccagatgc tactggactt     1020
gaatggttaa taaaactgca cagtgctgtt ggtggcagtg acttcttttg agttaggtta     1080
ataaatcaag ccatagagcc cctcctggtt gatacttgtt ccagatgggg cctttggggc     1140
tggtagaaat acccaacgca caaatgaccg cacgttctct gccccgtttc ttgcccagt      1200 gtggtttgca ttgtctcctt ccacaatgac tgctttgttt ggatgcctca gcccaggtca     1260
gctgttactt tctttcagat gtttatttgc aaacaaccat ttttgttct gtgtcccttt      1320 taaaaggcag attaaaagca caagcgtgtt tctagagaac agttgagaga gaatctcaag     1380
attctacttg gtggtttgct tgctctacgt tacaggtggg gcatgtcctc atcctttcct     1440
gccataaaag ctatgacacg agaatcagaa tattaataaa actttatgta ctgctgtagc     1500
aaaaaaaaaa aaaaaaaa                                                   1518

<210> SEQ ID NO 5
<211> LENGTH: 1730
<212> TYPE: DNA
<213> ORGANISM: Homo sapiens

<400> SEQUENCE: 5
atcaccgggc gtccgctccg gggtgccgtc gaggagacaa taggggggcgt gggccctcgt       60 ttacctccct ccctcctcc cttccctgcg ggccccgccg ggttccccat tgtctgaagg      120
gacggggcgg tgccccaggg accagcggct ttaggaccaa actgcgggca gccagggccg      180
cgaccctccc tgcgaccgtc ccctggcgac cgcagctggt gattgagggg cggcgctccc      240
gggccccacg agggttcttc tgtcttcgcg gccggacgcg cggacagcgt gggtggcggc      300
aggactttcc ttatcccagt tgattgtgca gaatacactg cctgtcgctt gtcttctatt      360
caccatggct tcttctgata tccaggtgaa agaactggag aagcgtgcct caggccaggc      420
ttttgagctg attctcagcc ctcggtcaaa agaatctgtt ccagaattcc ccctttcccc      480
tccaaagaag aaggatcttt ccctggagga aattcagaag aaattagaag ctgcagaaga      540
aagacgcaag tcccatgaag ctgaggtctt gaagcagctg gctgagaaac gagagcacga      600 gaagaagtg cttcagaagg caatagaaga gaacaacaac ttcagtaaaa tggcagaaga      660
gaaactgacc cacaaaatgg aagctaataa agagaaccga gaggcacaaa tggctgccaa      720
actggaacgt ttgcgagaga aggataagca cattgaagaa gtgcggaaga acaaagaatc      780
```

```
caaagaccct gctgacgaga ctgaagctga ctaatttgtt ctgagaactg actttctccc    840
catccccttc ctaaatatcc aaagactgta ctggccagtg tcattttatt ttttccctcc    900
tgacaaatat tttagaagct aatgtaggac tgtataggta gatccagatc cagactgtaa    960
gatgttgttt tagggctaa aggggagaaa ctgaaagtgt tttactcttt ttctaaagtg   1020
ttggtctttc taatgtagct attttcttg ttgcatcttt tctacttcag tacacttggt   1080
gtactgggtt aatggctagt actgtattgg ctctgtgaaa acatatttgt gaaaagagta   1140
tgtagtggct tcttttgaac tgttagatgc tgaatatctg ttcacttttc aatcccaatt   1200
ctgtcccaat cttaccagat gctactggac ttgaatggtt aataaaactg cacagtgctg   1260
ttggtggcag tgacttcttt tgagttaggt taataaatca agccatagag cccctcctgg   1320
ttgatacttg ttccagatgg ggcctttggg gctggtagaa atacccaacg cacaaatgac   1380
cgcacgttct ctgccccgtt tcttgcccca gtgtggtttg cattgtctcc ttccacaatg   1440
actgctttgt ttggatgcct cagcccaggt cagctgttac tttctttcag atgtttattt   1500
gcaaacaacc attttttgtt ctgtgtccct tttaaaaggc agattaaaag cacaagcgtg   1560
tttctagaga acagttgaga gagaatctca agattctact tggtggtttg cttgctctac   1620
gttacaggtg gggcatgtcc tcatcctttc ctgccataaa agctatgaca cgagaatcag   1680
aatattaata aaactttatg tactgctgta gcaaaaaaaa aaaaaaaaa                1730

<210> SEQ ID NO 6
<211> LENGTH: 2265
<212> TYPE: DNA
<213> ORGANISM: Homo sapiens

<400> SEQUENCE: 6
gctctcggcc aatgcggagc cccgcgcgga ggtcacgtgc ctctgtttgg cgcttttgtg     60
cgcgcccggg tctgttggtg ctcagagtgt ggtcaggcgg ctcggactga gcaggacttt    120
ccttatccca gttgattgtg cagaatacac tgcctgtcgc ttgtcttcta ttcaccatgg    180
cttcttctga tatccaggtg aaagaactgg agaagcgtgc ctcaggccag gcttttgagc    240
tgattctcag ccctcggtca aaagaatctg ttccagaatt ccccctttcc cctccaaaga    300
agaaggatct ttccctggag gaaattcaga agaaattaga agctgcagaa gaaagacgca    360
agtcccatga agctgaggtc ttgaagcagc tggctgagaa acgagagcac gagaaagaag    420
tgcttcagaa ggcaatagaa gagaacaaca acttcagtaa aatggcagaa gagaaactga    480
cccacaaaat ggaagctaat aaagagaacc gagaggcaca aatggctgcc aaactggaac    540
gtttgcgaga gaagatgtac ttctggactc acgggcctgg ggcccaccca gcacagatct    600
ctgctgagca atcttgtctc cactctgttc ctgcccttg cccagccctg gcctccaat    660 ctgcattgat tacctggtct gatctctctc accatcacta ggtacttaat aaatatttgc    720
tgttgatgat agcaatgacc ttgagactga tgaacagtct ggccaagagg atccttgatg    780
tggaagatag aaaaagcctt tggggtcagg cagacttgga ttctaatacc agccagttct    840
gcttgctgtg tctgagcctc agtttactca tctgtgaaga ggaggtagca agaatgaaaa    900
tgcctgcctt gtggtttgtt gtaaggacag acactgccaa cgtagagggc ccagcagctc    960
acagaccagt tgctctgaga gcagaccact cttgccttga tggtagggaa ctattttgt   1020 gcgtggcaag tgggacctta ggaaggaagg caactgtgag gcttctgaga aggaccctac   1080
acaagggagt ttcctcccag ggcaggtgaa tggagagggt ggcagaagcc tacgggaagg   1140
ggtcacaggg atcagctaga gagtgccacc acccttcctg gggaatgcag ggcaaggtcc   1200
```

-continued

```
ctggtgggag ttttcctggg aagccaaaga agcgcccaac aaagacagaa tcaacatttg    1260 ggtaccttttg gtacccagag gcagcaatgc caactacaac cacactggaa gaagaagacc    1320
ttctccgcat agattctctg atctcttcct ccttcatggc accagccctg gggaaccagc    1380
atggtgggga aataatgaag ctggaataca accacttaca gacttcacaa cctcctcctg    1440
tagataccaa agggatttta ggatcacatt ttatttctca cctgagcaag aaaagctaca    1500
ggagcatctc aagcagaggg caggagtctc cagaggagtt caaggggctc tgcaagaaa     1560 aatcaagggg ctgtgttcaa gaactggctc ccttggtgat tgtattacga agcccatgtg    1620
tgctggatgc tgatgaaatt gctgccaaat gcctgtgcag ccttggcaag gcccttttatt    1680 tctctgggtc tccatttctc tctctcttttt ttttttttttt tttttttttga ggcagagtct    1740 cactctgtcg cccaggctgg agggcagtgg cgtgatctcg gctcactgca agccccacct    1800
tctgagttca cgccattcta ctgcctcagc ctcccgagta gctgggacta caggcgccca    1860
ccaccacgcc cggcttattt tttgtatttt tagtagagac ggggtttcac cgcattagcc    1920
aagatggtct cgatctcctg acctcgtgat tcacccacct cagcctccca aagtgctggg    1980
attacaggca tgagccactg cgcccggcct gggtctccgt ttctctagct gtgaaatgac    2040
tgttctaaaa gagccctgcc ggactttggc agtctgtaag aagacctgag ttcttctctc    2100
agttccaagc aggaaaattg aacatacccct gagcccagag cctgcaacaa actctgggca    2160
gcctcaggaa gtcaggcagt gaagtcgaa aaatgatctc ttctgtatag ggagaaaata    2220
aaagtttaaa aatttgtaaa aaaaaaaaaa agaaaaaaaa aaaaa              2265
```